(12) United States Patent
Liang et al.

(10) Patent No.: US 7,683,057 B2
(45) Date of Patent: Mar. 23, 2010

(54) KINASE INHIBITOR COMPOUNDS

(75) Inventors: Congxin Liang, Palm Beach Gardens, FL (US); Ming Qi, Shanghai (CN); Shu Gao, Shanghai (CN); Zhigang Li, Shanghai (CN)

(73) Assignee: Tyrogenex, Inc., West Palm Beach, FL (US)

(*) Notice: Subject to any disclaimer, the term of this patent is extended or adjusted under 35 U.S.C. 154(b) by 0 days.

(21) Appl. No.: 12/005,872

(22) Filed: Dec. 28, 2007

(65) Prior Publication Data
US 2009/0076005 A1 Mar. 19, 2009

(51) Int. Cl.
*A61K 31/5377* (2006.01)
*A61K 31/404* (2006.01)
*C07D 413/14* (2006.01)
*C07D 209/34* (2006.01)

(52) U.S. Cl. .................. 514/235.2; 514/414; 544/144; 548/465

(58) Field of Classification Search ............ 514/235.2, 514/418, 323, 275, 380, 339, 414; 548/484, 548/244, 486; 546/201, 272.1; 544/331, 544/144, 129; 435/15, 184
See application file for complete search history.

(56) References Cited

U.S. PATENT DOCUMENTS

| | | | |
|---|---|---|---|
| 2003/0069297 A1* | 4/2003 | Cui et al. ............... | 514/414 |
| 2003/0125370 A1* | 7/2003 | Cui et al. ............... | 514/414 |
| 2005/0090541 A1 | 4/2005 | Arnaiz et al. | |
| 2006/0287381 A1 | 12/2006 | Liang et al. | |
| 2007/0072934 A1 | 3/2007 | Liang et al. | |
| 2008/0221132 A1* | 9/2008 | Cai et al. ............... | 514/263.24 |

FOREIGN PATENT DOCUMENTS

| | | |
|---|---|---|
| WO | WO-0160814 | 8/2001 |
| WO | WO-0202551 | 1/2002 |
| WO | WO-02055517 | 7/2002 |
| WO | WO-02066463 | 8/2002 |
| WO | WO-02096361 | 12/2002 |
| WO | WO-03031438 | 4/2003 |
| WO | WO-2005053686 | 6/2005 |
| WO | WO-2005058309 | 6/2005 |
| WO | WO-2006052936 | 5/2006 |
| WO | WO-2006127961 | 11/2006 |
| WO | WO-2007085205 | 2/2007 |
| WO | WO-2007081560 | 7/2007 |
| WO | WO-2008033743 | 3/2008 |
| WO | WO-2008033747 | 3/2008 |

OTHER PUBLICATIONS

Vippagunta et al., Crystalline solids, 2001, Advanced Drug Delivery Reviews, 48, 3-26.*

* cited by examiner

*Primary Examiner*—Kamal A Saeed
*Assistant Examiner*—Kristin Bianchi
(74) *Attorney, Agent, or Firm*—Edwards Angell Palmer & Dodge LLP; Jeffrey D. Hsi; Dwight D. Kim

(57) ABSTRACT

The invention relates to compounds, compositions comprising the compounds, and methods of using the compounds and compound compositions. The compounds, compositions, and methods described herein can be used for the therapeutic modulation of kinase-mediated processes, and treatment of disease and disease symptoms, particularly those mediated by certain kinase enzymes.

22 Claims, No Drawings

KINASE INHIBITOR COMPOUNDS

RELATED APPLICATIONS

This application claims benefit of PCT International Application No. US2007/020193 filed Sep. 14, 2007, which in turn claims the benefit of the U.S. Provisional Application No. 60/844,902 filed Sep. 15, 2006. The entire contents of each of these applications is incorporated herein by reference.

BACKGROUND

Sunitinib is a potent multi-targeted kinase inhibitor that is efficacious in the treatment of cancers, most notably renal cell carcinoma and GI stroma tumor as approved by FDA. It is also undergoing clinical trials in a number of other cancers. Its structure is an indolinone derivative characterized by a basic diethylaminoethyl side chain. Although Sunitinib is very efficacious, its application is hampered by the side effects. The most common and severe toxicity in clinic is neutropenia and fatigue.

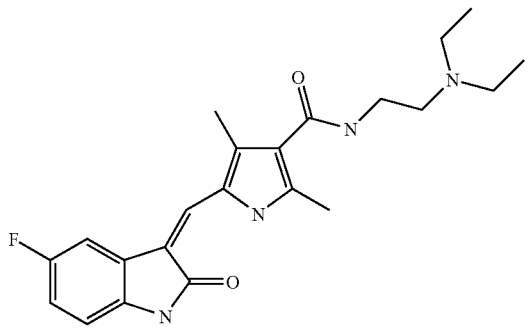

Sutent/Sunitinib/SU11248

This invention describes a novel class of Sunitinib derivatives with a cyclic side chain replacing the diethylaminoethyl side chain of Sunitinib. They are designed to overcome the fatigue problem of Sunitinib by improving its selectivity. Recently, a proteomic study of a Sunitinib analog, SU6668 found that SU6668 inhibits, among other proteins, AMPK (Godl et al, *Cancer Res* 2005, 65, 6919). Since AMPK is a key sensor of fuel and energy status in skeletal muscle (see review by Hardie and Sakamoto, *Physiology* 2006, 21, 48-60), it is hypothesized that inhibition of AMPK might be the cause of the clinically observed fatigue toxicity of Sunitinib. Thus, the cyclic derivatives of Sunitinib are designed to reduce the inhibitory activity of AMPK, thereby alleviating the fatigue problem of Sunitinib

SUMMARY

The invention relates to heterocyclic compounds, compositions comprising the compounds, and methods of using the compounds and compound compositions. The compounds and compositions comprising them are useful for treating disease or disease symptoms, including those mediated by or associated with kinase enzymes.

In one aspect is a compound of formula (I) or pharmaceutical salt, solvate or hydrate thereof:

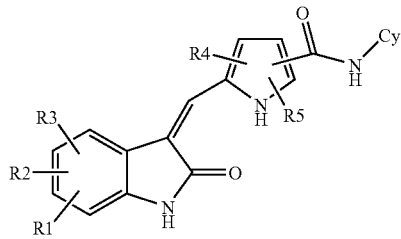

wherein Cy is a cyclic structure that can be cycloalkyl, heterocyclic, aryl, or heteroaryl, each optionally substituted with $Z_1$, $Z_2$ and $Z_3$;

$R_1$, $R_2$, $R_3$, $R_4$, and $R_5$ are each independently:
(1) hydrogen or $R_6$, where $R_6$, is alkyl, alkenyl, alkynyl, cycloalkyl, cycloalkylalkyl, cycloalkenyl, cycloalkenylalkyl, aryl, heteroaryl, aralkyl, heteroarylalkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —$C(O)_2H$, —$C(O)_qR_6$, —$C(O)NR_7R_8$, —$C(O)C(O)NR_7R_8$, or —O—$C(O)_qR_6$, where q is 1 or 2;
(5) —$SO_3H$, —$S(O)_qR_6$, or —$S(O)_qNR_7R_8$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$P(O)(OR_6)_2$;

$R_7$, $R_8$, $R_9$, $R_{10}$, $R_{11}$ and $R_{12}$ are each independently:
(1) hydrogen or $R_6$;
(2) $R_7$ and $R_8$ together with the nitrogen atom to which they are attached may be a heterocycle which is unsubstituted or substituted with $Z_1$, $Z_2$ and $Z_3$; or
(3) any two of $R_9$, $R_{10}$ and $R_{11}$ together with the nitrogen atoms to which they are attached may be a 3- to 12-membered saturated or unsaturated mono-, bi-, or tri-heterocyclic ring which is unsubstituted or substituted with $Z_1$, $Z_2$ and $Z_3$;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (13);
(2) —OH or —$OZ_{16}$;
(3) —SH or —$SZ_{16}$;
(4) —$C(O)_2H$, $C(O)_qZ_{16}$, —$C(O)NZ_{17}Z_{18}$, —$C(O)C(O)NZ_{17}Z_{18}$, or —O—$C(O)_qZ_{16}$, where q is 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—$C(O)$—$Z_{16}$;

(13) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently
(1) a single bond;
(2) —$Z_{11}$—S(O)$_q$—$Z_{12}$—;
(3) —$Z_{11}$—C(O)—$Z_{12}$—;
(4) —$Z_{11}$—O—$Z_{12}$—;
(5) —$Z_{11}$—S—$Z_{12}$—;
(6) —$Z_{11}$—O—C(O)—$Z_{12}$—; or
(7) —$Z_{11}$—C(O)—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(2) —OH or —O$Z_{21}$;
(3) —SH or —S$Z_{21}$;
(4) —C(O)$_2$H, C(O)$_q Z_{21}$, —C(O)N$Z_{17} Z_{18}$, —C(O)C(O)N$Z_{17} Z_{18}$, or —O—C(O)$_q Z_{21}$, where q is 1 or 2;
(5) —SO$_3$H, —S(O)$_q Z_{21}$, or —S(O)$_q$N$Z_{17} Z_{18}$;
(6) halo;
(7) cyano;
(8) nitro;
(9) —$Z_4$—N$Z_{17} Z_{18}$;
(10) —$Z_4$—N($Z_{18}$)—$Z_5$—N$Z_{19} Z_{20}$;
(11) oxo;
(12) —O—C(O)—$Z_{21}$;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; each $Z_{22}$ is independently is,
(2) —OH or —O$Z_{21}$;
(3) —SH or —S$Z_{21}$;
(4) —C(O)$_2$H, C(O)$_q Z_{21}$, —C(O)N$Z_{21} Z_{21}$, —C(O)C(O)N$Z_{21} Z_{21}$, or —O—C(O)$_q Z_{21}$, where q is 1 or 2;
(5) —SO$_3$H, —S(O)$_q Z_{21}$, or —S(O)$_q$N$Z_{21} Z_{21}$;
(6) halo;
(7) cyano;
(8) nitro;
(9) —$Z_4$—N$Z_{21} Z_{21}$;
(10) —$Z_4$—N($Z_{21}$)—$Z_5$—N$Z_{21} Z_{21}$;
(11) oxo;
(12) —O—C(O)—$Z_{21}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$;

provided said compound is other than a compound of formula IIa or IIb.

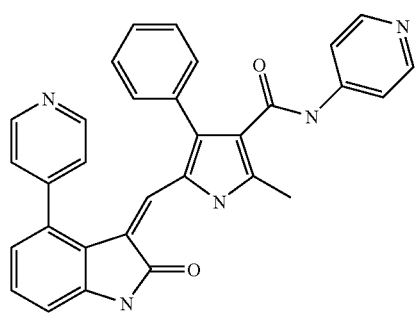

IIa

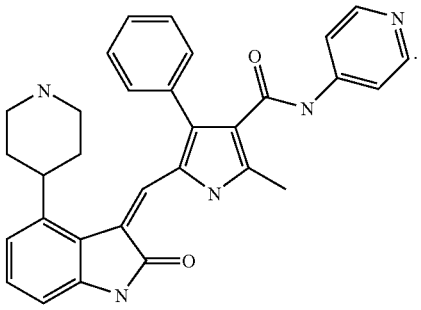

IIb

Another aspect is the compound of formula (I), or pharmaceutical salt, solvate or hydrate thereof, wherein:

$R_1$, $R_2$, $R_3$, $R_4$, and $R_5$ are each independently:
(1) hydrogen or $R_6$, where $R_6$, is alkyl, alkenyl, alkynyl, cycloalkyl, cycloalkylalkyl, cycloalkenyl, cycloalkenylalkyl, aryl, heteroaryl, aralkyl, heteroarylalkyl, heterocyclo, or heterocycloalkyl, each of which is unsubstituted or substituted with $Z_1$, $Z_2$ and one or more (preferably, one or two) groups $Z_3$;
(2) —OH or —O$R_6$;
(3) —SH or —S$R_6$;
(4) —C(O)$_2$H, —C(O)$_q R_6$, —C(O)N$R_7 R_8$, or —O—C(O)$_q R_6$, where q is 1 or 2;
(5) —SO$_3$H, —S(O)$_q R_6$, or —S(O)$_q$N$R_7 R_8$;
(6) halo;
(7) cyano;
(8) nitro;
(9) —$Z_4$—N$R_7 R_8$;
(10) —$Z_4$—N($R_9$)—$Z_5$—N$R_{10} R_{11}$;
(11) —$Z_4$—N($R_{12}$)—$Z_5$—$R_6$;
(12) —P(O)(O$R_6$)$_2$.

In one aspect is a compound of formula (I) or pharmaceutical salt, solvate or hydrate thereof:

wherein Cy is a cyclic structure that can be cycloalkyl, heterocyclic, aryl, or heteroaryl, each optionally substituted with $Z_1$, $Z_2$ and $Z_3$;

$R_1$, $R_2$, $R_3$, $R_4$, and $R_5$ are each independently:
(1) hydrogen or $R_6$, where $R_6$, is alkyl, alkenyl, alkynyl, cycloalkyl, cycloalkylalkyl, cycloalkenyl, cycloalkenylalkyl, aryl, heteroaryl, aralkyl, heteroarylalkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —C(O)$_2$H, —C(O)$_q R_6$, —C(O)NR$_7$R$_8$, or —O—C(O)$_q R_6$, where q is 1 or 2;
(5) —SO$_3$H, —S(O)$_q R_6$, or —S(O)$_q$NR$_7$R$_8$;
(6) halo;
(7) cyano;
(8) nitro;
(9) —$Z_4$—NR$_7$R$_8$;
(10) —$Z_4$—N(R$_9$)—$Z_5$—NR$_{10}$R$_{11}$;
(11) —$Z_4$—N(R$_{12}$)—$Z_5$—R$_6$;
(12) —P(O)(OR$_6$)$_2$;

$R_7$, $R_8$, $R_9$, $R_{10}$, $R_{11}$ and $R_{12}$ are each independently:
(1) hydrogen or $R_6$;
(2) $R_7$ and $R_8$ together with the nitrogen atom to which they are attached may be a heterocycle which is unsubstituted or substituted with $Z_1$, $Z_2$ and $Z_3$; or
(3) any two of $R_9$, $R_{10}$ and $R_{11}$ together with the nitrogen atoms to which they are attached may be a 3- to 12-membered saturated or unsaturated mono-, bi-, or tri-heterocyclic ring which is unsubstituted or substituted with $Z_1$, $Z_2$ and $Z_3$;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (13) of the definition of $Z_1$, $Z_2$ and $Z_3$;
(2) —OH or —$OZ_6$;
(3) —SH or —$SZ_6$;
(4) —C(O)$_2$H, C(O)$_q Z_6$, —C(O)NZ$_7$Z$_8$, or —O—C(O)$_q$ Z$_6$, where q is 1 or 2;
(5) —SO$_3$H, —S(O)$_q Z_6$, or —S(O)$_q$NZ$_7$Z$_8$;
(6) halo;
(7) cyano;
(8) nitro;
(9) —$Z_4$—NZ$_7$Z$_8$;
(10) —$Z_4$—N(Z$_8$)—$Z_5$—NZ$_9$Z$_{10}$;
(11) oxo;
(12) —O—C(O)—$Z_6$;
(13) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently
(1) a single bond;
(2) —$Z_{11}$—S(O)$_q$—$Z_{12}$—;
(3) —$Z_{11}$—C(O)—$Z_{12}$—;
(4) —$Z_{11}$—O—$Z_{12}$—;
(5) —$Z_{11}$—S—$Z_{12}$—;
(6) —$Z_{11}$—O—C(O)—$Z_{12}$—; or
(7) —$Z_{11}$—C(O)—O—$Z_{12}$;

$Z_7$, $Z_8$, $Z_9$ and $Z_{10}$ are each independently:
(1) hydrogen or $Z_6$;
(2) $Z_7$ and $Z_8$, or $Z_9$ and $Z_{10}$, together with the nitrogen atom to which they are attached may be a heterocycle which is unsubstituted or substituted with $Z_1$, $Z_2$ and $Z_3$; or
(3) any two of $Z_8$, $Z_9$ or $Z_{10}$ together with the nitrogen atoms to which they are attached may be a 3- to 12-membered saturated or unsaturated mono-, bi-, or tri-heterocyclic ring which is unsubstituted or substituted with $Z_1$, $Z_2$ and $Z_3$;

$Z_{11}$ and $Z_{12}$ are each independently
(1) a single bond;
(2) alkylene;
(3) alkenylene; or
(4) alkynylene;
provided said compound is other than a compound of formula IIa or IIb.

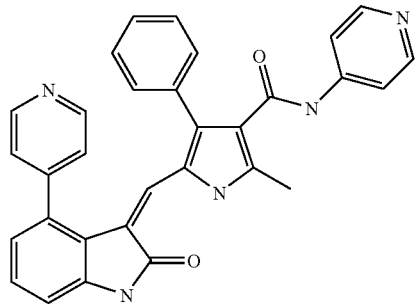

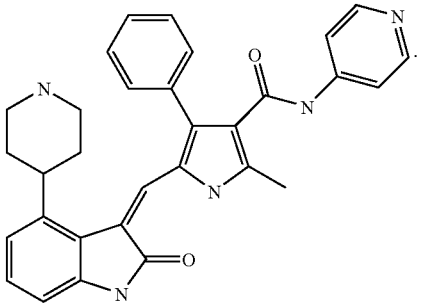

In other aspects, the compounds are those of any of the formulae herein (including any combinations thereof):
wherein Cy is a non-aromatic cycloalkyl or heterocyclic structure that is optionally substituted with $Z_1$, $Z_2$ and $Z_3$;
wherein Cy is a heterocyclic structure that is optionally substituted with $Z_1$, $Z_2$ and $Z_3$;
wherein any $R_1$, $R_2$ or $R_3$ in the 4-indolinone position is not a heterocycle or heteroaryl group;

wherein the Cy is optionally substituted cycloalkyl;
wherein the Cy is optionally substituted 5-membered ring heterocyclic;
wherein the Cy is optionally substituted 6-membered ring heterocyclic;
wherein the Cy is optionally substituted heteroaryl; and
wherein the compound of formula I is a compound delineated in any of the tables herein, or pharmaceutical salt, solvate or hydrate thereof.

Another aspect is a compound (or pharmaceutical salt, solvate or hydrate thereof) having the structure of formula III:

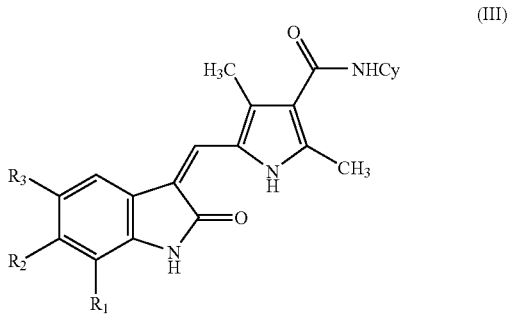

wherein $R_1$, $R_2$, $R_3$, and Cy are as defined herein, including in formula (I).

Other aspects of formula (III) are those: wherein $R_3$ is halo; wherein $R_3$ is fluoro; and wherein $R_1$ and $R_2$ are H, and $R_3$ is fluoro.

In another aspect, the invention relates to a method of treating a disease or disease symptom in a subject in need thereof including administering to the subject an effective amount of a compound of any formulae herein, or pharmaceutical salt, solvate or hydrate thereof (or composition thereof). The disease or disease symptom can be any of those modulated by a kinase enzyme (e.g., VEGFR, PDGFR, KIT, Flt-3, RET). The disease or disease symptom can be cancer, including for example renal cell carcinoma and GI stroma tumor, tumor or proliferative disorder.

In another aspect, the invention relates to a method of modulating (e.g., inhibiting, antagonism, agonism) kinase activity including contacting a kinase with a compound of any of the formulae herein or pharmaceutical salt, solvate or hydrate thereof (or composition thereof).

In another aspect, the invention relates to a method of making a compound of formula I herein, including reacting an intermediate delineated herein with a reagent to provide a compound of formula I as defined herein.

In another aspect, the invention relates to a composition including a compound of any of the formulae herein, or pharmaceutically acceptable salt, solvate or hydrate thereof, and a pharmaceutically acceptable carrier. The composition can further include an additional therapeutic agent.

In another aspect, the invention relates to a method of modulating a growth factor receptor (e.g. VEGFR, PDGFR, KIT, Flt-3, RET) activity in a subject in need thereof including administering to the subject an effective amount of a compound of any of the formulae herein, or pharmaceutical salt thereof (or composition thereof).

In other aspects, the invention relates to a composition comprising a compound of any of the formulae herein, an additional therapeutic agent, and a pharmaceutically acceptable carrier. The additional therapeutic agent can be an anticancer agent, antitumor agent, antiproliferative agent, or any other agent typically administered as a primary or adjuvant agent in cancer treatment protocols (e.g., antinausea, antianemia, etc.).

Yet another aspect of this invention relates to a method of treating a subject (e.g., mammal, human, horse, dog, cat) having a disease or disease symptom (including, but not limited to) that is or is associated with cancer, tumor(s), proliferative disorders, etc. The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Yet another aspect of this invention relates to a method of treating a subject (e.g., mammal, human, horse, dog, cat) having a kinase-mediated disease or disease symptom (including, but not limited to cancer, tumor, proliferative disorder, etc). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The methods of treatment include aspects where adverse side effects are minimized or non-existent. In one aspect the compound selectively inhibits a kinase target preferentially over inhibition of AMPK; in another aspect the compound selectively inhibits a kinase target preferentially over inhibition of AMPK with greater selectivity than Sunitinib; in another aspect the subject experiences little or no fatigue side effect.

Another aspect is a method of identifying a kinase inhibitor that selectively inhibits a kinase target preferentially over inhibition of AMPK comprising: (i) assaying a test compound for inhibition of a kinase enzyme; (ii) assaying the test compound for inhibition of AMPK; (iii) assessing whether the test compound inhibits a kinase target preferentially over inhibition of AMPK. Other aspects are the method wherein the test compound inhibits a kinase target preferentially over inhibition of AMPK with greater selectivity than Sunitinib.

Another aspect is a method of treating a disease or disease symptom in a subject in need thereof comprising administering to the subject an effective amount of a compound identified by the method above, or pharmaceutical salt, solvate or hydrate thereof.

The invention also relates to a method of making a compound described herein, the method including any reactions or reagents as delineated in the schemes or examples herein. Alternatively, the method includes taking any one of the intermediate compounds described herein and reacting it with one or more chemical reagents in one or more steps to produce a compound described herein.

Also within the scope of this invention is a packaged product. The packaged product includes a container, one of the aforementioned compounds in the container, and a legend (e.g., a label or an insert) associated with the container and indicating administration of the compound for treating a disorder associated with kinase modulation (e.g., cancer, tumor, proliferative disorder, etc.).

Another aspect of the invention is a compound of the invention for use in the treatment or prevention in a subject of a disease, disorder or symptom thereof delineated herein.

Another aspect of the invention is the use of a compound of the invention in the manufacture of a medicament for treatment or prevention in a subject of a disease, disorder or symptom thereof delineated herein.

In other embodiments, the compounds, compositions, and methods delineated herein are any of the compounds of the tables herein or methods including them.

The details of one or more embodiments of the invention are set forth in the accompanying drawings and the description below. Other features, objects, and advantages of the invention will be apparent from the description and from the claims.

DETAILED DESCRIPTION

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive). The term "arylalkyl" refers to a moiety in which an alkyl hydrogen atom is replaced by an aryl group. The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —(CH$_2$)$_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH═CH—CH═CH—, —CH$_2$—CH═CH—, —CH$_2$—CH═CH—CH$_2$—, —C(CH$_3$)$_2$CH═C— and —CH(C$_2$H$_5$)—CH═CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —CC—, —CH$_2$—CC—, —CH(CH$_3$)—CC— and —CC—CH(C$_2$H$_5$)CH$_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)R$^{17}$, NR$^{15}$C(O)R$^{17}$, S(O)R$^{17}$, S(O)$_2$R$^{17}$, R$^{16}$, oxo, C(O)R$^{16}$, C(O)(CH$_2$)nOH, (CH$_2$)nOR$^{15}$, (CH$_2$)nC(O)NR$^{15}$R$^{16}$, NR$^{15}$S(O)$_2$R$^{17}$, where n is independently 0-6 inclusive. Each R$^{15}$ is independently hydrogen, C$_1$-C$_4$ alkyl or C$_3$-C$_6$ cycloalkyl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, NH$_2$, C$_1$-C$_4$ alkylamino, C$_1$-C$_4$ dialkylamino, C$_1$-C$_2$ perfluoroalkyl, C$_1$-C$_2$ perfluoroalkoxy, or 1,2-methylenedioxy.

In one aspect, the substituents on a group are independently, hydrogen, hydroxyl, halogen, nitro, SO$_3$H, trifluoromethyl, trifluoromethoxy, alkyl(C1-C6 straight or branched), alkoxy(C1-C6 straight or branched), O-benzyl, O-phenyl, phenyl, 1,2-methylenedioxy, carboxyl, morpholinyl, piperidinyl, amino or OC(O)NR$_{15}$R$^{16}$. Each R$^{15}$ and R$^{16}$ is as described above.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound, which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg. Effective doses will also vary depending on route of administration, as well as the possibility of co-usage with other agents.
Representative compounds useful in the compositions and methods are delineated herein:
TABLE 1
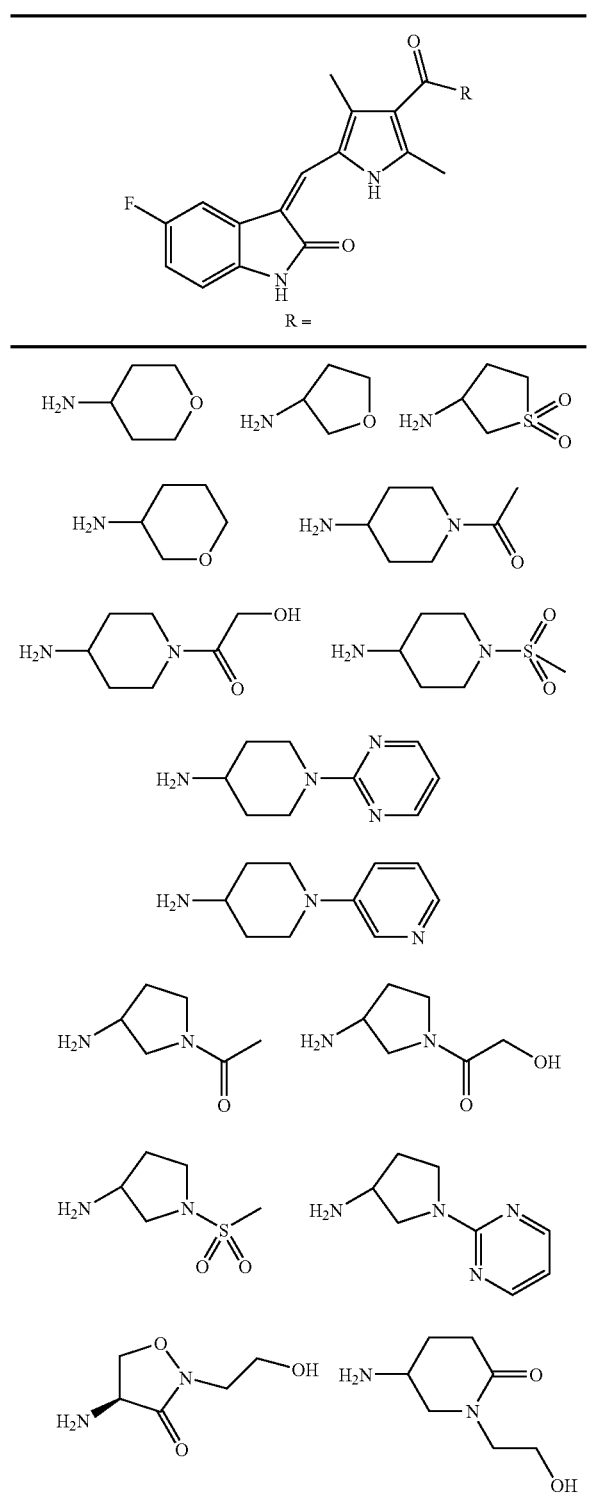
TABLE 1-continued
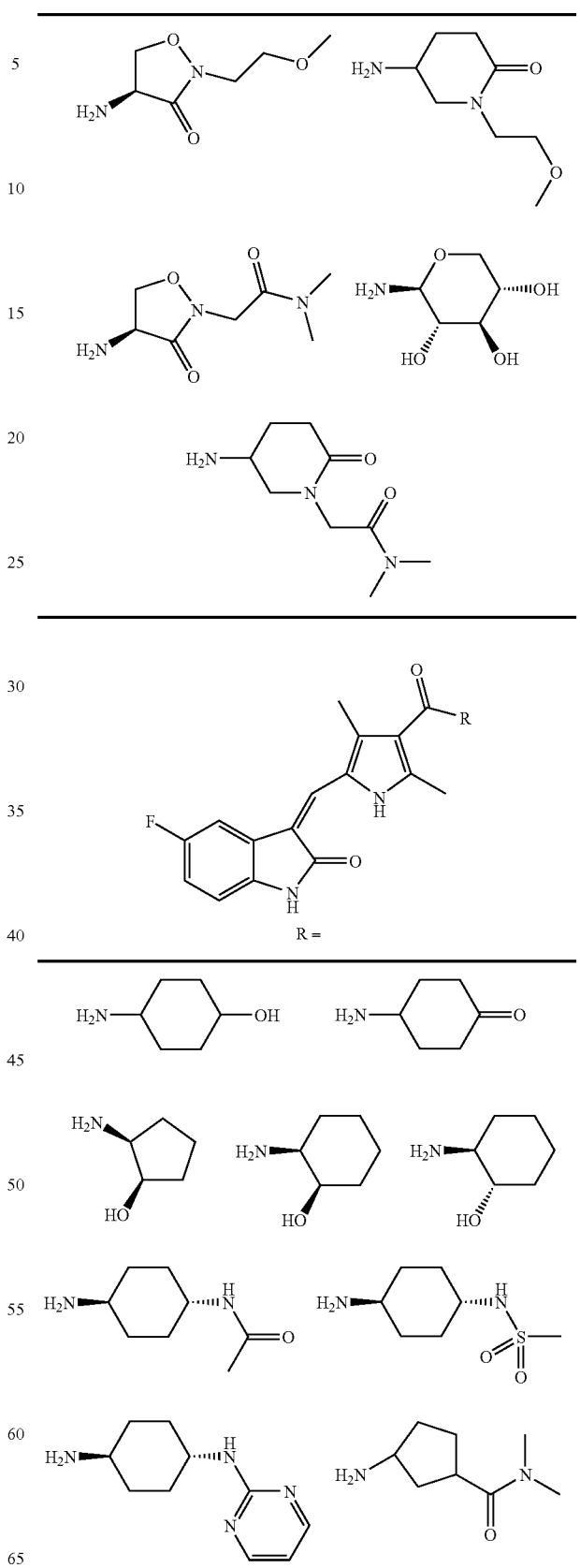

TABLE 1-continued

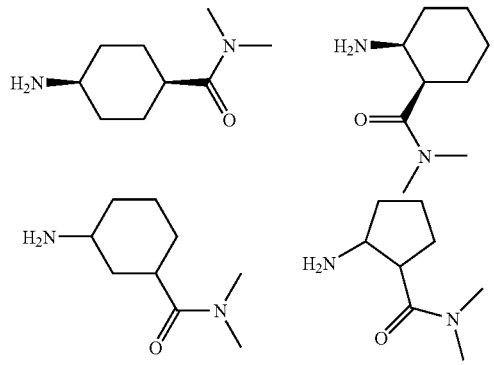

The Table 1 compounds also include the following:
5-[5-fluoro-2-oxo-1,2-dihydro-indol-(3Z)-ylidenemethyl]-2,4-dimethyl-1H-pyrrole-3-carboxylic acid (1-acetyl-piperidin-4-yl)-amide,
5-[5-fluoro-2-oxo-1,2-dihydro-indol-(3Z)-ylidenemethyl]-2,4-dimethyl-1H-pyrrole-3-carboxylic acid (1-methanesulfonyl-piperidin-4-yl)-amide,
N-(2H-3,4,5,6-tetrahydropyran-4-yl){5-[(5-fluoro-2-oxo(1H-benzo[d]azolin-3-ylidene))methyl]-2,4-dimethylpyrrol-3-yl}carboxamide,
5-[5-Fluoro-2-oxo-1,2-dihydro-indol-(3Z)-ylidenemethyl]-2,4-dimethyl-1H-pyrrole-3-carboxylic acid piperidin-4-ylamide,
5-[5-Fluoro-2-oxo-1,2-dihydro-indol-(3Z)-ylidenemethyl]-2,4-dimethyl-1H-pyrrole-3-carboxylic acid ((S)-1-acetyl-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid ((S)-1-methanesulfonyl-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid (1,1-dioxo-tetrahydro-thiophen-3-yl)-amide,
5-[5-Fluoro-2-oxo-1,2-dihydro-indol-(3Z)-ylidenemethyl]-2,4-dimethyl-1H-pyrrole-3-carboxylic acid (1-pyrimidin-2-yl-piperidin-4-yl)-amide,
5-[5-Fluoro-2-oxo-1,2-dihydro-indol-(3Z)-ylidenemethyl]-2,4-dimethyl-1H-pyrrole-3-carboxylic acid (3,4,5,6-tetrahydro-2H-[1,3']bipyridinyl-4-yl)-amide,
5-[5-Fluoro-2-oxo-1,2-dihydro-indol-(3Z)-ylidenemethyl]-2,4-dimethyl-1H-pyrrole-3-carboxylic acid (4-hydroxy-1,1-dioxo-tetrahydro-thiophen-3-yl)-amide,
5-[5-Fluoro-2-oxo-1,2-dihydro-indol-(3Z)-ylidenemethyl]-2,4-dimethyl-1H-pyrrole-3-carboxylic acid (1,1-dioxo-hexahydro-thiopyran-4-yl)-amide,
5-[5-Fluoro-2-oxo-1,2-dihydro-indol-(3Z)-ylidenemethyl]-2,4-dimethyl-1H-pyrrole-3-carboxylic acid ((S)-6-oxo-piperidin-3-yl)-amide,
5-[5-Fluoro-2-oxo-1,2-dihydro-indol-(3Z)-ylidenemethyl]-2,4-dimethyl-1H-pyrrole-3-carboxylic acid ((2S,3S,4R,5S,6S)-3,4,5-trihydroxy-6-hydroxymethyl-tetrahydro-pyran-2-yl)-amide,
5-[5-Fluoro-2-oxo-1,2-dihydro-indol-(3Z)-ylidenemethyl]-2,4-dimethyl-1H-pyrrole-3-carboxylic acid [1-(2-hydroxy-acetyl)-piperidin-4-yl]-amide,
5-[5-Fluoro-2-oxo-1,2-dihydro-indol-(3Z)-ylidenemethyl]-2,4-dimethyl-1H-pyrrole-3-carboxylic acid [(S)-1-(2-hydroxy-acetyl)-pyrrolidin-3-yl]-amide,
5-[5-Fluoro-2-oxo-1,2-dihydro-indol-(3Z)-ylidenemethyl]-2,4-dimethyl-1H-pyrrole-3-carboxylic acid (4-hydroxy-tetrahydro-furan-3-yl)-amide,
5-[5-Fluoro-2-oxo-1,2-dihydro-indol-(3Z)-ylidenemethyl]-2,4-dimethyl-1H-pyrrole-3-carboxylic acid ((S)-2-oxo-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid (1-benzyl-4-hydroxy-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid (1-acetyl-4-hydroxy-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid (1-dimethylaminooxalyl-piperidin-4-yl)-amide,
5-[5-Fluoro-2-oxo-1,2-dihydro-indol-(3Z)-ylidenemethyl]-2,4-dimethyl-1H-pyrrole-3-carboxylic acid ((S)-1-dimethylaminooxalyl-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid ((2S,3S,4R,5S)-3,4-dihydroxy-5-hydroxymethyl-tetrahydro-furan-2-yl)-amide,
5-[5-Fluoro-2-oxo-1,2-dihydro-indol-(3Z)-ylidenemethyl]-2,4-dimethyl-1H-pyrrole-3-carboxylic acid ((S)-1-carbonylmethyl-2-oxo-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid [(S)-1-(2-hydroxy-ethyl)-2-oxo-pyrrolidin-3-yl]-amide,
5-[5-Fluoro-2-oxo-1,2-dihydro-indol-(3Z)-ylidenemethyl]-2,4-dimethyl-1H-pyrrole-3-carboxylic acid [(R)-2-(2-hydroxy-ethyl)-3-oxo-isoxazolidin-4-yl]-amide,
5-[5-Fluoro-2-oxo-1,2-dihydro-indol-(3Z)-ylidenemethyl]-2,4-dimethyl-1H-pyrrole-3-carboxylic acid ((R)-2-dimethylcarbamoylmethyl-3-oxo-isoxazolidin-4-yl)-amide,
5-[5-Fluoro-2-oxo-1,2-dihydro-indol-(3Z)-ylidenemethyl]-2,4-dimethyl-1H-pyrrole-3-carboxylic acid ((R)-2-ethyl-3-oxo-isoxazolidin-4-yl)-amide,
5-[5-Fluoro-2-oxo-1,2-dihydro-indol-(3Z)-ylidenemethyl]-2,4-dimethyl-1H-pyrrole-3-carboxylic acid ((R)-2-carbamoylmethyl-3-oxo-isoxazolidin-4-yl)-amide,
5-[5-Fluoro-2-oxo-1,2-dihydro-indol-(3Z)-ylidenemethyl]-2,4-dimethyl-1H-pyrrole-3-carboxylic acid [(R)-2-(2-methoxy-ethyl)-3-oxo-isoxazolidin-4-yl]-amide,
5-[5-Fluoro-2-oxo-1,2-dihydro-indol-(3Z)-ylidenemethyl]-2,4-dimethyl-1H-pyrrole-3-carboxylic acid ((R)-3-oxo-2-pyridin-3-ylmethyl-isoxazolidin-4-yl)-amide,
5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-yl)-isoxazolidin-4-yl]-amide,
5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-3-yl)-isoxazolidin-4-yl]-amide,
5-[5-Fluoro-2-oxo-1,2-dihydro-indol-(3Z)-ylidenemethyl]-2,4-dimethyl-1H-pyrrole-3-carboxylic acid [1-(morpholine-4-carbonyl)-piperidin-4-yl]-amide,
5-[5-Fluoro-2-oxo-1,2-dihydro-indol-(3Z)-ylidenemethyl]-2,4-dimethyl-1H-pyrrole-3-carboxylic acid [(S)-1-(morpholine-4-carbonyl)-pyrrolidin-3-yl]-amide,
4-({5-[5-Fluoro-2-oxo-1,2-dihydro-indol-(3Z)-ylidenemethyl]-2,4-dimethyl-1H-pyrrole-3-carbonyl}-amino)-piperidine-1-carboxylic acid dimethylamide,
5-[5-Fluoro-2-oxo-1,2-dihydro-indol-(3Z)-ylidenemethyl]-2,4-dimethyl-1H-pyrrole-3-carboxylic acid ((S)-1-dimethylcarbamoyl-pyrrolidin-3-yl)-amide,
5-[5-Fluoro-2-oxo-1,2-dihydro-indol-(3Z)-ylidenemethyl]-2,4-dimethyl-1H-pyrrole-3-carboxylic acid [1-(2-methoxy-acetyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-acetyl)-pyrrolidin-3-yl]-amide, N-((3R)oxolan-3-yl){5-[(5-fluoro-2-oxo(1H-benzo[d]azolin-3-ylidene))methyl]-2,4-dimethylpyrrol-3-yl}carboxamide, 5-[5-Fluoro-2-oxo-1,2-dihydro-indol-(3Z)-ylidenemethyl]-2,4-dimethyl-1H-pyrrole-3-carboxylic acid [(R)-2-(2-morpholin-4-yl-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-2-oxo-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid ((S)-2-oxo-1-pyridin-4-ylmethyl-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-ylmethyl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-methoxy-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [1-(2-dimethylamino-acetyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-dimethylamino-acetyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-hydroxy-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-ethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid (6'-methyl-3,4,5,6-tetrahydro-2H-[1,3']bipyridinyl-4-yl)-amide, 5-[5-Fluoro-2-oxo-1,2-dihydro-indol-(3Z)-ylidenemethyl]-2,4-dimethyl-1H-pyrrole-3-carboxylic acid [(S)-1-(6-methyl-pyridin-3-yl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(S)-2-oxo-1-(tetrahydro-pyran-4-ylmethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-methanesulfonyl-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methanesulfonyl-ethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(R)-2-(2-methanesulfonyl-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-2-(2-methoxy-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(R)-2-(2-ethoxy-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-2,5-dioxo-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-3-ylmethyl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-2-ylmethyl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-2,5-dioxo-1-(tetrahydro-pyran-4-ylmethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(S)-2,5-dioxo-1-(tetrahydro-pyran-4-yl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid ((S)-1-dimethylcarbamoyl-2-oxo-pyrrolidin-3-yl)-amide.

The Table 1 compounds also include the following:

5-[5-fluoro-2-oxo-1,2-dihydro-indol-(3Z)-ylidenemethyl]-2,4-dimethyl-1H-pyrrole-3-carboxylic acid (4-hydroxy-cyclohexyl)-amide, 5-[5-Fluoro-2-oxo-1,2-dihydro-indol-(3Z)-ylidenemethyl]-2,4-dimethyl-1H-pyrrole-3-carboxylic acid (4-amino-cyclohexyl)-amide, 5-[5-Fluoro-2-oxo-1,2-dihydro-indol-(3Z)-ylidenemethyl]-2,4-dimethyl-1H-pyrrole-3-carboxylic acid (4-oxo-cyclohexyl)-amide, 5-[5-Fluoro-2-oxo-1,2-dihydro-indol-(3Z)-ylidenemethyl]-2,4-dimethyl-1H-pyrrole-3-carboxylic acid ((1S,2S)-2-hydroxy-cyclopentyl)-amide, 5-[5-Fluoro-2-oxo-1,2-dihydro-indol-(3Z)-ylidenemethyl]-2,4-dimethyl-1H-pyrrole-3-carboxylic acid ((1S,2R)-2-hydroxy-cyclopentyl)-amide, 5-[5-Fluoro-2-oxo-1,2-dihydro-indol-(3Z)-ylidenemethyl]-2,4-dimethyl-1H-pyrrole-3-carboxylic acid (4-acetylamino-cyclohexyl)-amide, 5-[5-Fluoro-2-oxo-1,2-dihydro-indol-(3Z)-ylidenemethyl]-2,4-dimethyl-1H-pyrrole-3-carboxylic acid (4-methanesulfonylamino-cyclohexyl)-amide, 5-[5-Fluoro-2-oxo-1,2-dihydro-indol-(3Z)-ylidenemethyl]-2,4-dimethyl-1H-pyrrole-3-carboxylic acid ((1S,2S)-2-hydroxy-cyclohexyl)-amide, 5-[5-Fluoro-2-oxo-1,2-dihydro-indol-(3Z)-ylidenemethyl]-2,4-dimethyl-1H-pyrrole-3-carboxylic acid [4-(morpholine-4-carbonyl)-cyclohexyl]-amide, 5-[5-Fluoro-2-oxo-1,2-dihydro-indol-(3Z)-ylidenemethyl]-2,4-dimethyl-1H-pyrrole-3-carboxylic acid [4-(pyrrolidine-1-carbonyl)-cyclohexyl]-amide, 5-[5-Fluoro-2-oxo-1,2-dihydro-indol-(3Z)-ylidenemethyl]-2,4-dimethyl-1H-pyrrole-3-carboxylic acid [4-(aziridine-1-carbonyl)-cyclohexyl]-amide, 5-[5-Fluoro-2-oxo-1,2-dihydro-indol-(3Z)-ylidenemethyl]-2,4-dimethyl-1H-pyrrole-3-carboxylic acid [(1R,3S)-3-(pyrrolidine-1-carbonyl)-cyclopentyl]-amide, 5-[5-Fluoro-2-oxo-1,2-dihydro-indol-(3Z)-ylidenemethyl]-2,4-dimethyl-1H-pyrrole-3-carboxylic acid [(1R,3S)-3-(morpholine-4-carbonyl)-cyclopentyl]-amide, 5-[5-Fluoro-2-oxo-1,2-dihydro-indol-(3Z)-ylidenemethyl]-2,4-dimethyl-1H-pyrrole-3-carboxylic acid [(1R,3S)-3-(aziridine-1-carbonyl)-cyclopentyl]-amide, 5-[5-Fluoro-2-oxo-1,2-dihydro-indol-(3Z)-ylidenemethyl]-2,4-dimethyl-1H-pyrrole-3-carboxylic acid [(1R,2S)-2-(pyrrolidine-1-carbonyl)-cyclopentyl]-amide, 5-[5-Fluoro-2-oxo-1,2-dihydro-indol-(3Z)-ylidenemethyl]-2,4-dimethyl-1H-pyrrole-3-carboxylic acid [(1R,2S)-2-(morpholine-4-carbonyl)-cyclopentyl]-amide, 5-[5-Fluoro-2-oxo-1,2-dihydro-indol-(3Z)-ylidenemethyl]-2,4-dimethyl-1H-pyrrole-3-carboxylic acid [(1R,2S)-2-(aziridine-1-carbonyl)-cyclopentyl]-amide.

In the structures in the table above, the attachment of the R group is via the amino nitrogen atom depicted as "NH$_2$" and thus is meant that moiety attached to the depicted carbonyl group as an "—N-cyclic group" where the cyclic group is cycloalkyl, cycloalkenyl, heterocyclo (any of which may be substituted).

Kinase-modulating compounds can be identified through both in vitro (e.g., cell and non-cell based) and in vivo methods. Representative examples of these methods are described in the Examples herein.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The compounds delineated herein can be synthesized using conventional methods, as illustrated in the schemes herein. In the schemes herein, unless expressly to the contrary, variables in chemical formulae correspond to similar positions as defined in other formulae herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof. The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

As used herein, the compounds of this invention, including the compounds of formulae described herein, and are in embodiments intended to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein. See, e.g., Alexander, J. et al. *Journal of a Medicinal Chemistry* 1988, 31, 318-322; Bundgaard, H. *Design of Prodrugs; Elsevier: Amsterdam,* 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214; Sinkula, A. A.; Yalkowsky. *Journal of Pharmaceutical Sciences* 1975, 64, 181-210; Verbiscar, A. J.; Abood, L. G *Journal of Medicinal Chemistry* 1970, 13, 1176-1179; Stella, V. J.; Himmelstein, K. J. *Journal of Medicinal Chemistry* 1980, 23, 1275-1282; Bodor, N.; Kaminski, J. *J. Annual Reports in Medicinal Chemistry* 1987, 22, 303-313.

The compounds of this invention may be modified by appending appropriate functionalities to enhance selective biological properties. Such modifications are known in the art and include those which increase biological penetration into a given biological compartment (e.g., blood, lymphatic system, nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect.

Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

The compositions delineated herein include the compounds of the formulae delineated herein, as well as additional therapeutic agents if present, in amounts effective for achieving a modulation of disease or disease symptoms, including kinase-mediated disorders or symptoms thereof. References which include examples of additional therapeutic agents are: 1) *Burger's Medicinal Chemistry & Drug Discovery* 6$^{th}$ edition, by Alfred Burger, Donald J. Abraham, ed., Volumes 1 to 6, Wiley Interscience Publication, NY, 2003. Additional therapeutic agents include but are not limited to agents for treatment of diseases, disorders or symptoms thereof including for example, anticancer agents, antiproliferative agents, antineoplastic agents, antitumor agents, antimetabolite-type/thymidilate synthase inhibitor antineoplastic agents, alkylating-type antineoplastic agents, antibiotic-type antineoplastic agents, or, any other agent typically administered as a primary or adjuvant agent in cancer treatment protocols (e.g., antinausea, antianemia, etc.), including for example, vinblastine sulfate, vincristine, vindesine, vinestramide, vinorelbine, vintriptol, vinzolidine, tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, Iressa, Avastin, OSI-774, angiogenesis inhibitors, EGF inhibitors, MEK inhibitors, VEGF inhibitors, CDK inhibitors, Her1 and Her2 inhibitors and monoclonal antibodies.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as or α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The invention will be further described in the following examples. It should be understood that these examples are for illustrative purposes only and are not to be construed as limiting this invention in any manner.

EXAMPLES

The general procedure for the preparation of many examples is shown below:

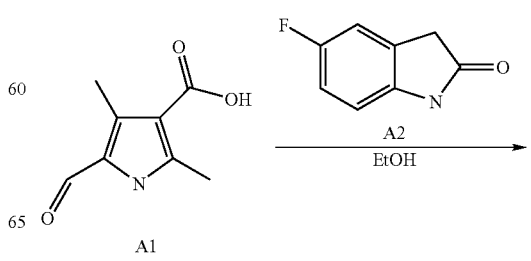

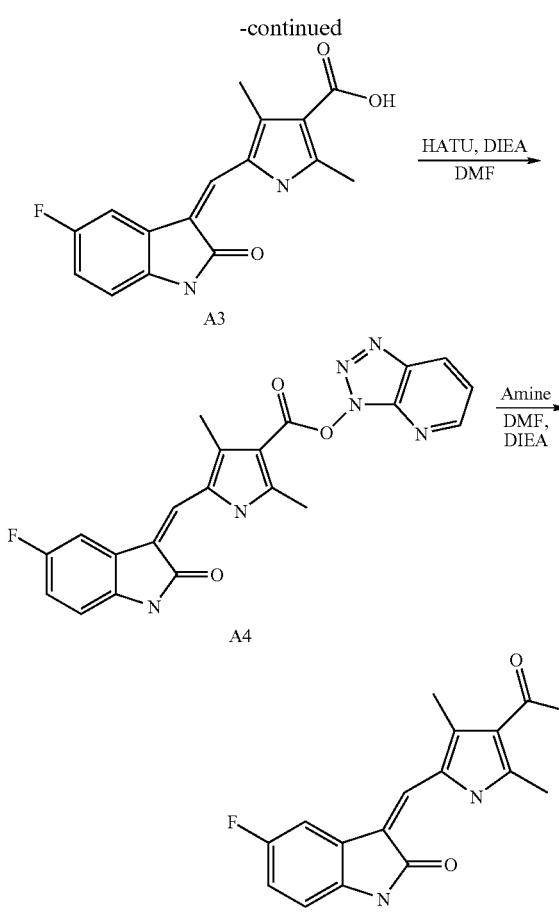

Step 1: A mixture of 5-fluoro-1,3-dihydroindol-2-one (A2) (20 g, 132 mmol), 5-formyl-2,4-dimethylpyrrole-3-carboxylic acid (A1) (21.1 g, 126 mmol), pyrrolidine (5 ml) and absolute ethanol (400 mL) were heated to reflux for 3 hours. Then the mixture was cooled to room temperature and the solid was collected by filtration, washed with ethanol (100 mL). The solid was stirred in ethanol (350 ml) at reflux for 0.5 h again. The mixture was cooled to room temperature and the solid was collected by filtration, washed with ethanol (100 ml) and dried under vacuum overnight to give (Z)-5-((5-fluoro-2-oxoindolin-3-ylidene)methyl)-2,4-dimethyl-1H-pyrrole-3-carboxylic acid (A3) (35.3 g, 93%) as orange solid. LC-MS observed [M−H]+: 299.2.

Step 2: (Z)-5-((5-fluoro-2-oxoindolin-3-ylidene)methyl)-2,4-dimethyl-1H-pyrrole-3-carboxylic acid (A3) (5 g, 16.7 mmol) was suspended in DMF (25 mL) with stirring for 5 min. DIEA (4.4 mL, 25 mmol) was then added and the mixture was stirred for 10 min. HATU (6.32 g, 16.6 mmol) was added and the reaction mixture was stirred at room temperature for several hours. LC/MS was used to detect the completion of the reaction. Most DMF was evaporated under vacuum and the residue was suspended in ACN and stirred for another 30 min. The solid was collected via filtration and washed with ACN, dried under vacuum to provide (Z)-3H-[1,2,3]triazolo[4,5-b]pyridin-3-yl-5-((5-fluoro-2-oxoindolin-3-ylidene)methyl)-2,4-dimethyl-1H-pyrrole-3-carboxylate (A4) (5.36 g, 77%). LC-ESIMS observed [M−H]+: 417.3.

Step 3: To the solution of (Z)-3H-[1,2,3]triazolo[4,5-b]pyridin-3-yl 5-((5-fluoro-2-oxoindolin-3-ylidene)methyl)-2,4-dimethyl-1H-pyrrole-3-carboxylate (A4) (1.0 eq) in DMF solution was added the appropriate amine (1.2 eq) and DIEA (2.0 eq). The reaction mixture was stirred at room temperature for several hours. LC/MS detection was applied to determine completion of the reaction. After removal of most DMF under vacuum the mixture was precipitated with 5% diethylamine/methanol (25 mL) with stirring. The solid was collected by filtration and washed with methanol (5 mL) for several times, dried under high vacuum to provide the final compound (40-85% yields).

Example 1

Preparation of 5-[5-fluoro-2-oxo-1,2-dihydro-indol-(3Z)-ylidenemethyl]-2,4-dimethyl-1H-pyrrole-3-carboxylic acid (4-hydroxy-cyclohexyl)-amide

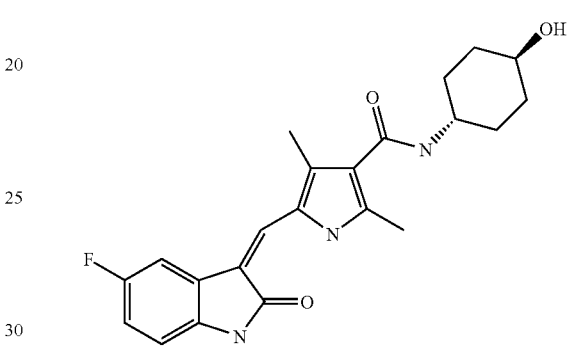

Following the general procedure, an orange solid was obtained (162 mg, 86% yield). $^1$H NMR (300 MHz, DMSO-d6): δ=13.64 (s, 1H), 10.86 (s, 1H), 7.72-7.77 (dd, 1H), 7.70 (s, 1H), 7.45-7.47 (d, 1H), 6.81-6.95 (m, 2H), 4.52-4.53 (d, 1H), 3.66-3.68 (m, 1H), 3.36-3.39 (m, 1H), 2.38-2.40 (ds, 6H), 1.82-1.86 (d, 4H), 1.23-1.34 (m, 4H). LC/MS: 398.3 [M+H]+.

Example 2

Preparation of 5-[5-fluoro-2-oxo-1,2-dihydro-indol-(3Z)-ylidenemethyl]-2,4-dimethyl-1H-pyrrole-3-carboxylic acid (1-acetyl-piperidin-4-yl)-amide

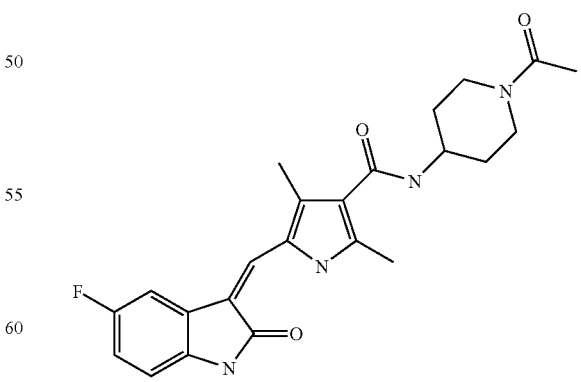

Following the general procedure, an orange solid was obtained (174 mg, 83% yield). $^1$H NMR (300 MHz, DMSO-d6): δ=13.67 (s, 1H), 10.88 (s, 1H), 7.74-7.78 (dd, 1H), 7.71 (s, 1H), 7.59-7.62 (d, 1H), 6.81-6.96 (m, 2H), 4.23-4.27 (d, 1H), 3.96-3.99 (m, 1H), 3.76-3.81 (m, 1H), 3.11-3.19 (m, 1H), 2.70-2.74 (m, 1H), 2.39-2.41 (ds, 6H), 2.00 (s, 3H), 1.77-1.89 (m, 2H), 1.31-1.47 (m, 2H). LC/MS: 423.4 [M–H]+.

Example 3

Preparation of 5-[5-fluoro-2-oxo-1,2-dihydro-indol-(3Z)-ylidenemethyl]-2,4-dimethyl-1H-pyrrole-3-carboxylic acid (1-methanesulfonyl-piperidin-4-yl)-amide

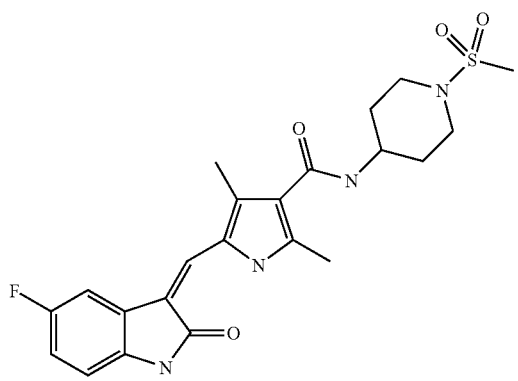

Following the general procedure, an orange solid was obtained (171 mg, 77% yield). $^1$H NMR (300 MHz, DMSO-d6): δ=13.68 (s, 1H), 10.90 (s, 1H), 7.67-7.79 (m, 3H), 6.83-6.93 (m, 2H), 3.89-3.91 (m, 1H), 3.51-3.55 (d, 2H), 2.85-2.91 (m, 5H), 2.27-2.41 (ds, 6H), 1.90-1.95 (d, 2H), 1.58-1.61 (m, 2H). LC/MS: 459.4 [M–H]+.

Example 4

Preparation of 5-[5-Fluoro-2-oxo-1,2-dihydro-indol-(3Z)-ylidenemethyl]-2,4-dimethyl-1H-pyrrole-3-carboxylic acid (4-amino-cyclohexyl)-amide

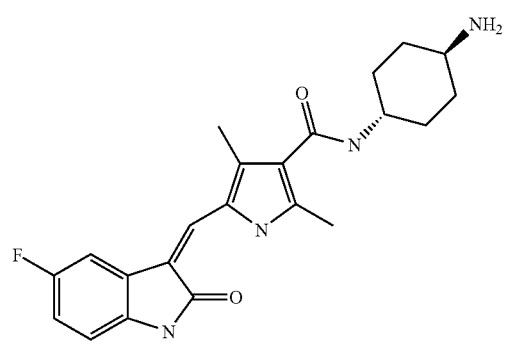

Following the general procedure, an orange solid was obtained (121 mg, 63% yield). $^1$H NMR (300 MHz, DMSO-d6): δ=13.65 (s, 1H), 7.70-7.77 (m, 2H), 7.44-7.47 (d, 1H), 6.81-6.92 (m, 2H), 3.62-3.71 (m, 1H), 2.38-2.40 (ds, 6H), 1.76-1.84 (m, 4H), 1.10-1.32 (m, 5H). LC/MS: 397.2 [M+H]+.

Example 5

Preparation of N-(2H-3,4,5,6-tetrahydropyran-4-yl){5-[(5-fluoro-2-oxo(1H-benzo[d]azolin-3-ylidene))methyl]-2,4-dimethylpyrrol-3-yl}carboxamide

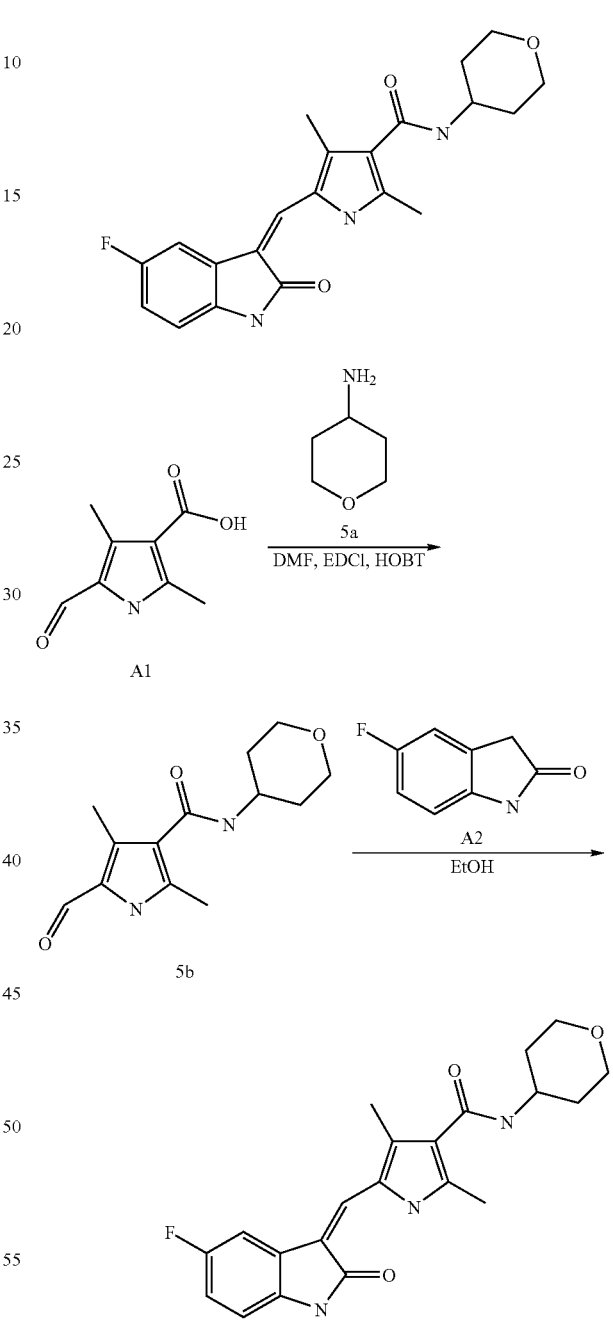

Step 1: A mixture of 5-formyl-2,4-dimethylpyrrole-3-carboxylic acid (A1) (1 g, 6.0 mmol) in 25 mL of anhydrous DMF was stirred at room temperature while HOBt (1.216 g, 9.0 mmol), EDCI (1.726 g, 9.0 mmol), TEA (3.4 mL, 24 mmol) and 2H-3,4,5,6-tetrahydropyran-4-ylamine (5a) (0.99 g, 7.2 mmol) were added. The resulting mixture was stirred for 20 h at room temperature. Then the reaction mixture was diluted with 3 mL each of H$_2$O, brine and saturated sodium bicarbonate solution. The pH was adjusted to greater than 10 with 10N aqueous NaOH solution. The mixture was extracted three times with 10 mL of DCM containing 10% methanol. The extracts were combined, dried over anhydrous MgSO$_4$ and evaporated under vacuum. The residue was triturated with mixed solvent of EA:MeOH (5:1, 10 mL). The resulting solid was filtered and dried to provide compound N-(2H-3,4,5,6-tetrahydropyran-4-yl) (5-formyl-2,4-dimethylpyrrol-3-yl)carboxamide (5b) as white solid. (475 mg, 32%). LC-MS: 249.3 [M–H]$^+$.

Step 2: A mixture of 2N-(2H-3,4,5,6-tetrahydropyran-4-yl)(5-formyl-2,4-dimethylpyrrol-3-yl)-carboxamide (5b) (200 mg, 0.8 mmol), 5-fluoroindolin-2-one (A2) (126 mg, 0.84 mmol) and pyrrolidine (two drops) in 10 mL of ethanol were heated to reflux for 3 h. The mixture was cooled to room temperature and the solid was collected by filtration and washed with ethanol. The obtained solid was stirred in ethanol (10 ml) at reflux for 0.5 h again. The mixture was cooled to room temperature and the solid was collected by filtration, washed with ethanol and dried under vacuum to give the title compound (80 mg, 26% yield) as orange solid. $^1$H NMR (300 MHz, DMSO-d6): δ=13.67 (s, 1H), 10.87 (s, 1H), 7.74-7.78 (dd, 1H), 7.71 (s, 1H), 7.60-6.63 (d, 1H), 6.82-6.96 (m, 2H), 3.83-3.98 (m, 3H), 3.38-3.42 (m, 2H), 2.40-2.42 (ds, 6H), 1.76-1.81 (dd, 1H), 1.56-1.59 (m, 2H). LC/MS: 382.4 [M–H]$^+$.

Example 6

Preparation of 5-[5-Fluoro-2-oxo-1,2-dihydro-indol-(3Z)-ylidenemethyl]-2,4-dimethyl-1H-pyrrole-3-carboxylic acid piperidin-4-ylamide

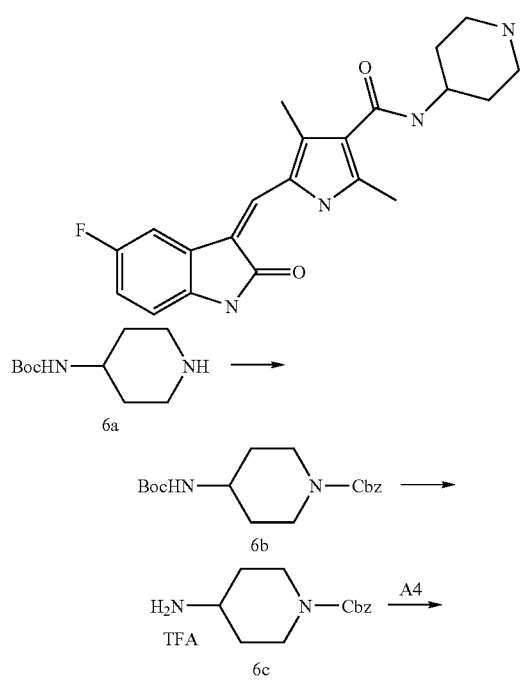

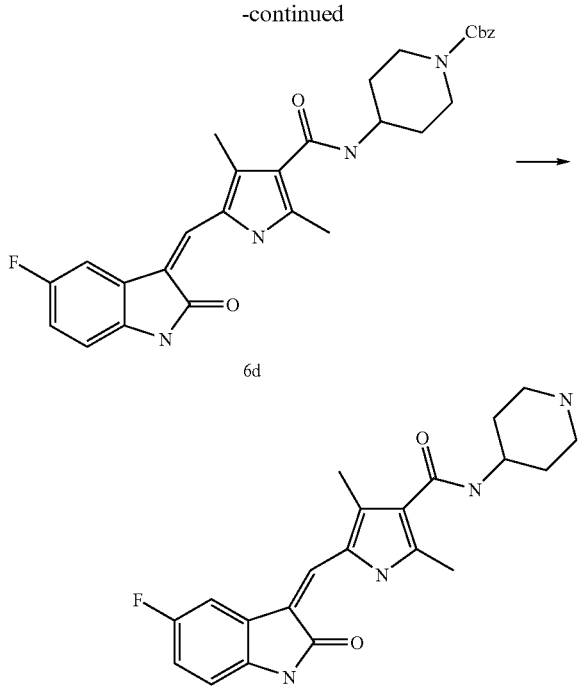

Step 1: Cbz-Cl (0.938 g, 5.5 mmol) was added to the solution of compound 6a (1 g, 5 mmol) and TEA (0.823 mL, 6 mmol) in 30 mL of DMF. The resulting mixture was stirred at room temperature for 45 min., then 30 mL of H$_2$O was added. The mixture was extracted by EA (50 mL*3). The combined organic extracts were dried over anhydrous MgSO$_4$, filtered and the filtrate was evaporated under reduced pressure to give a residue, which was purified by column chromatography (EA:PE=1:10) to provide compound 6b (1.46 g, 87%) as white solid, which was used directly to the next step.

Step 2: Compound 6b (1.46 g, 0.44 mmol) was dissolved in 50 mL of DCM and 5.76 mL of TFA was added. The resulting solution was stirred at room temperature for 2 h, evaporated to dryness to provide compound 6c (1.84 g, 99%) which was used directly in the next step.

Steps 3 & 4: To the solution of (Z)-3H-[1,2,3]triazolo[4,5-b]pyridin-3-yl 5-[(5-fluoro-2-oxoindolin-3-ylidene)methyl]-2,4-dimethyl-1H-pyrrole-3-carboxylate (A4) (0.2 g, 0.48 mmol) in 25 mL of DMF solution was added compound 6c (0.268 g, 0.58 mmol). The reaction mixture was stirred at room temperature for several hours. LC/MS detection was applied to determine completion of the reaction. 200 mg of 5% Pd/C was added to the mixture, followed by 25 mL of MeOH. The mixture was stirred under H$_2$ atmosphere for 30 min and filtered. The filtrate was evaporated under reduced pressure and the residue was triturated with 5% diethylamine/methanol (25 mL) under sonication. The solid was collected by filtration and washed with methanol (5 mL*2), dried under vacuum to provide the title compound (80 mg, 43.7% yield) as orange solid. $^1$H NMR (300 MHz, DMSO-d6): δ=13.67 (s, 1H), 10.89 (s, 1H), 7.67-7.78 (m, 3H), 6.82-6.96 (m, 2H), 3.87-3.92 (m, 1H), 3.06-3.09 (d, 2H), 2.72-2.79 (t, 2H), 2.39-2.41 (ds, 6H), 1.84-1.89 (d, 6H), 1.46-1.57 (m, 2H). LC/MS: 383.1 [M+H]$^+$.

Example 7

Preparation of 5-[5-Fluoro-2-oxo-1,2-dihydro-indol-(3Z)-ylidenemethyl]-2,4-dimethyl-1H-pyrrole-3-carboxylic acid (4-oxo-cyclohexyl)-amide

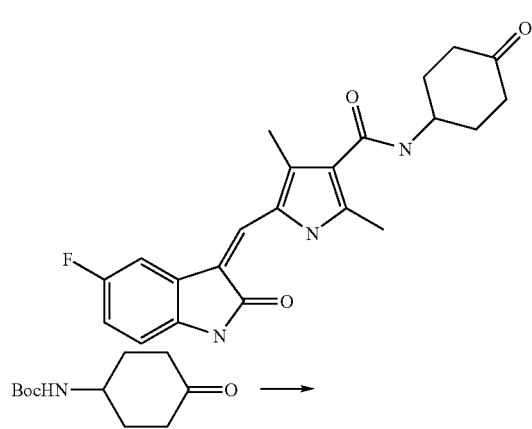

Example 8

Preparation of 5-[5-Fluoro-2-oxo-1,2-dihydro-indol-(3Z)-ylidenemethyl]-2,4-dimethyl-1H-pyrrole-3-carboxylic acid ((S)-1-acetyl-pyrrolidin-3-yl)-amide

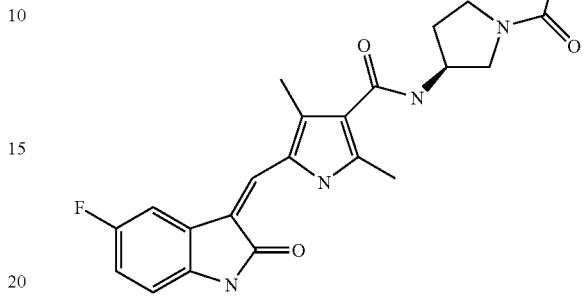

Preparation of Amines for Examples 8 and 9

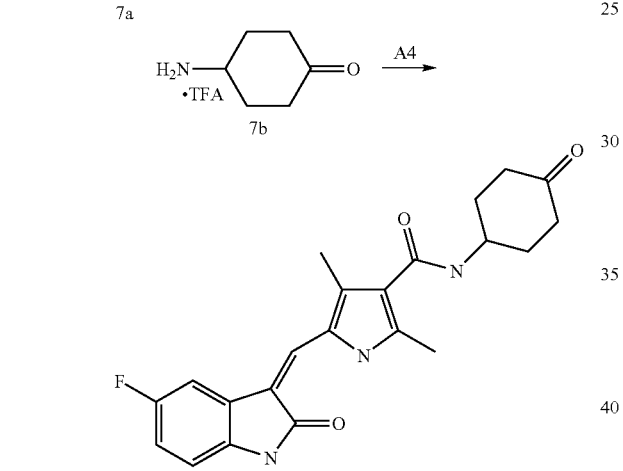

Step 1: Compound 7a (2.5 g, 11.74 mmol) was dissolved in 40 mL of DCM. 15.3 mL of TFA was added slowly. The resulting mixture was stirred at room temperature for 2 h, then evaporated to dryness under vacuum to provide crude compound 7b (2.60 g, 98%), which was used directly for the next step.

Step 2: To the solution of (Z)-3H-[1,2,3]triazolo[4,5-b]pyridin-3-yl-5-[(5-fluoro-2-oxoindolin-3-ylidene)methyl]-2,4-dimethyl-1H-pyrrole-3-carboxylate (A4) (0.2 g, 0.48 mmol) in 25 mL of DMF solution was added compound 7b (0.13 g, 0.58 mmol), the reaction mixture was stirred at room temperature for several hours. LC/MS detection was applied to determine completion of the reaction. DMF was evaporated under reduced pressure and the residue was precipitated with 5% diethylamine/methanol (25 mL) under sonication. The solid was collected by filtration and washed with methanol (5 mL*2), dried under vacuum to provide the title compound (50 mg, 26% yield) as orange solid. $^1$H NMR (300 MHz, DMSO-d6): δ=13.68 (s, 1H), 10.89 (s, 1H), 7.70-7.78 (m, 3H), 6.82-6.93 (m, 2H), 4.21-4.28 (m, 1H), 2.41-2.49 (m, 8H), 2.28-2.31 (m, 2H), 2.07-2.13 (m, 2H), 1.76-1.80 (m, 2H). LC/MS: 394.3 [M–H]$^+$.

Step 1a: Compound 8a (0.5 g, 2.7 mmol) and TEA (0.326 g, 3.2 mmol) were combined in 5 mL of DCM. Acetyl chloride (0.253 g, 3.2 mmol) was added drop-wise. The resulting mixture was stirred at room temperature for 4 h and evaporated under reduced pressure. The residue was dissolved in EA and washed with aqueous 5% NaHCO$_3$ solution and brine. The organic layer was dried over anhydrous MgSO$_4$ and evaporated to provide crude compound 8b (0.548 g, 90%), which was used directly for the next step.

Step 1b: To an ice-bath cooled solution of crude compound 8a (0.5 g, 2.7 mmol) and DIEA (1.6 g, 12.3 mmol) in 20 mL of THF was added mesyl chloride (0.54 g, 4.7 mmol) drop-wise. The mixture was then stirred at room temperature for about 1 h, poured into water and extracted with DCM. The combined organic phase was washed with 5% aq. NaHCO$_3$ solution, dried over anhydrous MgSO$_4$, filtered and the filtrate was evaporated under reduced pressure to give the crude compound 9b (0.654 g, 92%), which was used directly for the next step.

Step 2: Compound 8b or 9b (1.0 eq.) was dissolved in DCM. TFA (10 eq.) was added slowly. The resulting mixture was stirred at room temperature for 2 h, evaporated to dryness under vacuum to provide compound 8c or 9c.

Step 3: To the solution of (Z)-3H-[1,2,3]triazolo[4,5-b]pyridin-3-yl 5-((5-fluoro-2-oxoindolin-3-ylidene)methyl)-2,4-dimethyl-1H-pyrrole-3-carboxylate (A4) (1.0 eq.) and DIEA (2.0 eq.) in DMF solution was added compound 8c (1.2 eq), the reaction mixture was stirred at room temperature for several hours. LC/MS detection was applied to determine completion of the reaction. DMF was evaporated under reduced pressure and the residue was precipitated with 5% diethylamine/methanol under sonication. The solid was collected by filtration and washed with methanol twice, dried under high vacuum to provide the title compound (136 mg, 66% yield) as orange solid. $^1$H NMR (300 MHz, DMSO-d6): δ=13.68 (s, 1H), 10.89 (s, 1H), 7.72-7.92 (m, 3H), 6.82-6.96 (m, 2H), 4.34-4.48 (m, 1H), 3.25-3.75 (m, 4H), 2.39-2.42 (ds, 6H), 1.86-2.20 (m, 6H). LC/MS: 409.3 $[M-H]^+$.

Example 9

Preparation of 5-[5-Fluoro-2-oxo-1,2-dihydro-indol-(3Z)-ylidenemethyl]-2,4-dimethyl-1H-pyrrole-3-carboxylic acid ((S)-1-methanesulfonyl-pyrrolidin-3-yl)-amide

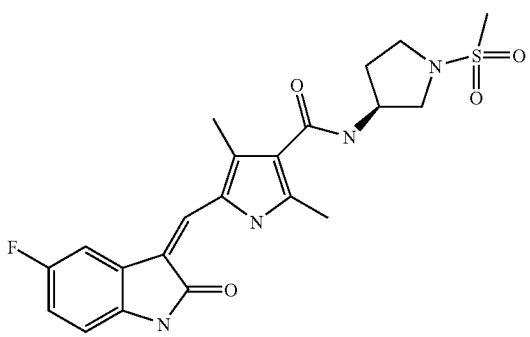

To the solution of (Z)-3H-[1,2,3]triazolo[4,5-b]pyridin-3-yl 5-((5-fluoro-2-oxoindolin-3-ylidene)methyl)-2,4-dimethyl-1H-pyrrole-3-carboxylate (A4) (1.0 eq.) and DIEA (2.0 eq.) in DMF solution was added compound 9c (1.2 eq), the reaction mixture was stirred at room temperature for several hours. LC/MS detection was applied to determine completion of the reaction. DMF was evaporated under reduced pressure and the residue was precipitated with 5% diethylamine/methanol under sonication. The solid was collected by filtration and washed with methanol twice, dried under high vacuum to provide the title compound (129 mg, 61% yield) as orange solid. $^1$H NMR (300 MHz, DMSO-d6): δ=13.70 (s, 1H), 10.90 (s, 1H), 7.72-7.90 (m, 3H), 6.82-6.96 (m, 2H), 4.42-4.48 (m, 1H), 3.53-3.58 (m, 1H), 3.36-3.42 (m, 1H), 3.13-3.18 (m, 1H), 2.93 (s, 3H), 2.41-2.43 (ds, 6H), 1.90-2.18 (m, 3H). LC/MS: 445.4 $[M-H]^+$.

Example 10

Preparation of 5-[5-Fluoro-2-oxo-1,2-dihydro-indol-(3Z)-ylidenemethyl]-2,4-dimethyl-1H-pyrrole-3-carboxylic acid (1,1-dioxo-tetrahydro-thiophen-3-yl)-amide

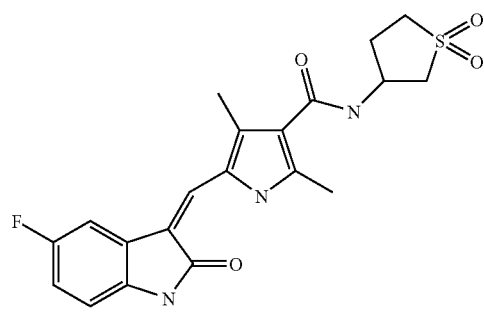

Preparation of 1,1-Dioxo-tetrahydro-thiophen-3-ylamine

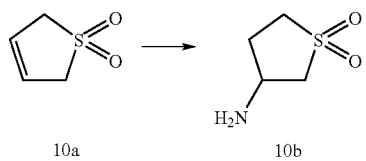

10a      10b

A solution of compound 10a (0.5 g, 4.2 mmol) in 10 mL of 26% NH$_4$OH was heated in a sealed tube at 80° C. for 4 h. The mixture was concentrated under reduced pressure to yellow oil which was dissolved in 3 mL of EtOH and treated with 1 mL of concentrated HCl. The mixture was stirred for 0.5 h and ethyl ether was added to precipitate the crystalline hydrochloride. The solid was collected by filtration, washed with ether and dried in vacuum to provide compound 10b (0.533 g, 74%).

To the solution of (Z)-3H-[1,2,3]triazolo[4,5-b]pyridin-3-yl 5-[(5-fluoro-2-oxoindolin-3-ylidene)methyl]-2,4-dimethyl-1H-pyrrole-3-carboxylate (A4) (0.207 g, 0.5 mmol) and DIEA (0.296 g, 2.0 eq.) in 25 mL of DMF solution was added compound 10b (0.162 g, 0.94 mmol), the reaction mixture was stirred at room temperature for several hours. LC/MS detection was applied to determine completion of the reaction. DMF was evaporated under reduced pressure and the residue was precipitated with 5% diethylamine/methanol (10 mL) under sonication. The solid was collected by filtration and washed with methanol (5 mL) twice, dried under vacuum to provide the title compound as orange solid (181 mg, 88% yield). $^1$H NMR (300 MHz, DMSO-d6): δ=13.72 (s, 1H), 10.91 (s, 1H), 7.97-7.80 (d, 1H), 7.73-7.70 (m, 2H), 6.82-6.97 (m, 2H), 4.63-4.65 (m, 1H), 3.44-3.51 (m, 1H), 3.18-3.29 (m, 1H), 3.03-3.10 (m, 1H), 2.42-2.50 (m, 8H), 2.16-2.23 (d, 6H). LC/MS: 416.2 $[M-H]^+$.

Example 11

Preparation of 5-[5-Fluoro-2-oxo-1,2-dihydro-indol-(3Z)-ylidenemethyl]-2,4-dimethyl-1H-pyrrole-3-carboxylic acid ((1S,2S)-2-hydroxy-cyclopentyl)-amide

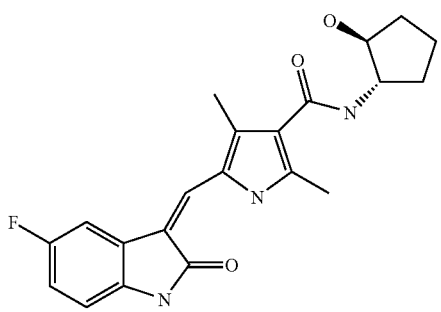

Following the general procedure, an orange solid was obtained (85 mg, 93% yield). $^1$H NMR (300 MHz, DMSO-d6): δ=13.67 (s, 1H), 10.88 (s, 1H), 7.52-7.78 (m, 3H), 6.82-6.96 (m, 2H), 4.76-4.77 (d, 1H), 3.92-3.97 (m, 2H), 2.39-2.42 (ds, 6H), 1.96-2.01 (m, 1H), 1.80-1.84 (m, 1H), 1.60-1.69 (m, 1H). LC/MS: 384.2 [M+H]$^+$.

Example 12

Preparation of 5-[5-Fluoro-2-oxo-1,2-dihydro-indol-(3Z)-ylidenemethyl]-2,4-dimethyl-1H-pyrrole-3-carboxylic acid ((1S,2R)-2-hydroxy-cyclopentyl)-amide

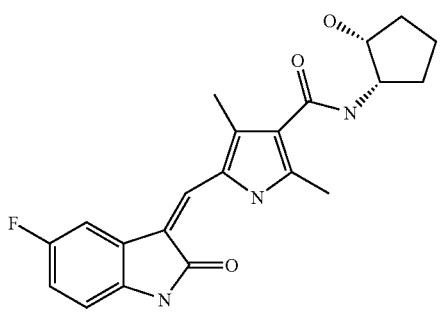

Following the general procedure, an orange solid was obtained (75 mg, 82% yield). $^1$H NMR (300 MHz, DMSO-d6): δ=13.72 (s, 1H), 10.90 (s, 1H), 7.72-7.79 (m, 2H), 6.82-7.01 (m, 3H), 4.81-4.83 (d, 1H), 4.02-4.04 (d, 2H), 2.44-2.47 (ds, 6H), 1.47-1.90 (m, 6H). LC/MS: 384.1 [M+H]$^+$.

Example 13

Preparation of 5-[5-Fluoro-2-oxo-1,2-dihydro-indol-(3Z)-ylidenemethyl]-2,4-dimethyl-1H-pyrrole-3-carboxylic acid (1-pyrimidin-2-yl-piperidin-4-yl)-amide

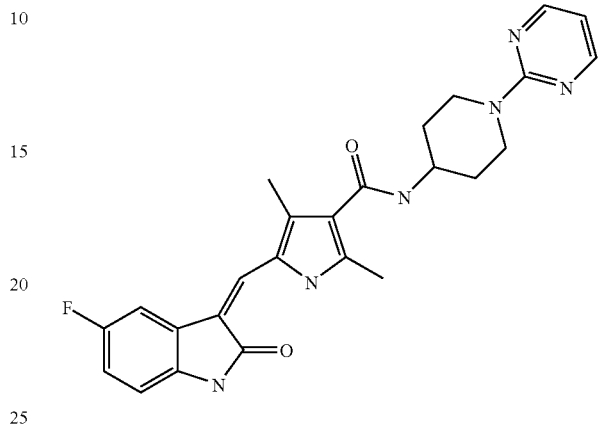

Preparation of Amine

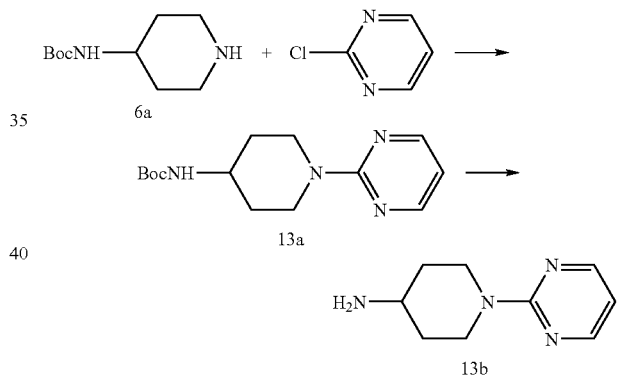

Step 1: A mixture of compound 6a (0.5 g, 2.5 mmol), 2-chloropyrimidine (0.86 g, 7.5 mmol) and K$_2$CO$_3$ (1.725 g, 12.5 mmol) in 10 mL of 1,4-dioxane was refluxed for 48 h, cooled to room temperature and filtered. The filtrate was evaporated under reduced pressure and the residue was purified by column chromatography (EA:PE=1:4) to provide compound 13a (0.61 g, 88%).

Step 2: Compound 13a (0.61 g, 2.2 mmol) was dissolved in 10 mL DCM, 3 mL TFA was added. The mixture was stirred at room temperature for 2 h and evaporated to dryness under reduced pressure to give the crude compound 13b (0.87 g, 98%).

To the solution of (Z)-3H-[1,2,3]triazolo[4,5-b]pyridin-3-yl 5-((5-fluoro-2-oxoindolin-3-ylidene)methyl)-2,4-dimethyl-1H-pyrrole-3-carboxylate (A4) (0.207 g, 0.5 mmol) and DIEA (0.15 g, 2.0 eq.) in 25 mL of DMF solution was added compound 13b (0.235 g, 0.58 mmol), the reaction mixture was stirred at room temperature for several hours. LC/MS detection was applied to determine completion of the reaction. DMF was evaporated under reduced pressure and the residue was precipitated with 5% diethylamine/methanol (10 mL) under sonication. The solid was collected by filtration and washed with methanol (5 mL*2), dried under vacuum to provide title compound (189 mg, 82%) as orange solid. $^1$H NMR (300 MHz, DMSO-d6): δ=13.66 (s, 1H), 10.87 (s, 1H), 8.34-8.36 (d, 2H), 7.71-7.77 (m, 2H), 7.56-7.59 (d, 1H), 6.82-6.95 (m, 2H), 6.58-6.61 (t, 1H), 4.56-4.60 (d, 2H), 4.04-4.10 (m, 1H), 3.06-3.13 (m, 2H), 2.40-2.42 (ds, 6H), 1.86-1.91 (d, 2H), 1.40-1.52 (m, 2H). LC/MS: 459.4 [M−H]$^+$.

Example 14

Preparation of 5-[5-Fluoro-2-oxo-1,2-dihydro-indol-(3Z)-ylidenemethyl]-2,4-dimethyl-1H-pyrrole-3-carboxylic acid (3,4,5,6-tetrahydro-2H-[1,3']bipyridinyl-4-yl)-amide

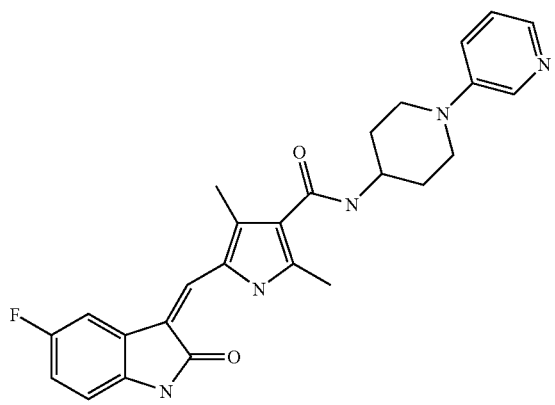

Preparation of Amine

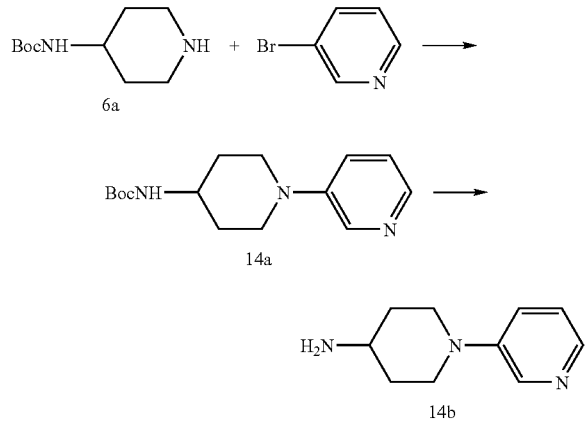

Step 1: Pd(dba)3 (0.046 g, 0.05 mmol), Xantphos (0.087 g, 0.15 mmol) and Cs$_2$CO$_3$ (1.1 g, 3.37 mmol) were added to 20 mL of 1,4-dioxane under N$_2$, compound 6a (0.5 g, 2.5 mmol) and 3-bromopyridine (0.513 g, 3.2 mmol) were added to this mixture. The resulting mixture was heated to 100° C. for 24 h and cooled to room temperature which was taken up in EA (50 mL), washed with brine and water. The organic phase was dried with anhydrous MgSO$_4$ and concentrated under reduced pressure to give a residue which was purified by column chromatography (PE:EA=1:2) to provide compound 14a (0.51 g, 73.6%).

Step 2: Compound 14a (0.51 g, 1.84 mmol) was dissolved in 10 mL of DCM and 3 mL of TFA was added. The mixture was stirred at room temperature for 2 h and evaporated to dryness under reduced pressure to give the crude compound 14b (0.74 g, 99%).

To the solution of (Z)-3H-[1,2,3]triazolo[4,5-b]pyridin-3-yl 5-((5-fluoro-2-oxoindolin-3-ylidene) methyl)-2,4-dimethyl-1H-pyrrole-3-carboxylate (A4) (0.1 g, 0.24 mmol) and DIEA (0.074 g, 2.4 eq.) in 10 mL of DMF solution was added crude 14b (0.12 g, 0.29 mmol). The reaction mixture was stirred at room temperature for several hours. LC/MS detection was applied to determine completion of the reaction. DMF was evaporated under reduced pressure and the residue was precipitated with 5% diethylamine/methanol (10 mL) under sonication. The solid was collected by filtration and washed with methanol (5 mL) twice, dried under vacuum to provide title compound (90 mg, 82% yield) as orange solid. $^1$H NMR (300 MHz, DMSO-d6): δ=13.68 (s, 1H), 10.89 (s, 1H), 8.32-8.33 (d, 1H), 7.95-7.97 (dd, 1H), 7.74-7.78 (dd, 1H), 7.62-7.64 (d, 1H), 7.32-7.36 (m, 1H), 7.18-7.22 (m, 1H), 6.82-6.96 (m, 2H), 3.95-3.97 (m, 1H), 3.74-3.78 (m, 2H), 2.86-2.90 (t, 2H), 2.40-2.42 (ds, 6H), 1.89-1.93 (d, 2H), 1.59-1.68 (m, 2H). LC/MS: 460.1 [M+H]$^+$.

Example 15

Preparation of 5-[5-Fluoro-2-oxo-1,2-dihydro-indol-(3Z)-ylidenemethyl]-2,4-dimethyl-1H-pyrrole-3-carboxylic acid (4-acetylamino-cyclohexyl)-amide

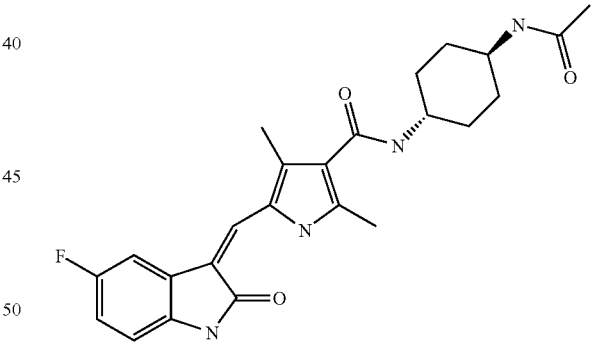

To the solution of Example 4 (1.0 eq.) and DIEA (2.0 eq.) in DMF solution was added compound acetyl chloride (1.2 eq), the reaction mixture was stirred at room temperature for several hours. LC/MS detection was applied to determine completion of the reaction. DMF was evaporated under reduced pressure and the residue was precipitated with 5% diethylamine/methanol under sonication. The solid was collected by filtration and washed with methanol twice, dried under high vacuum to provide title compound (10 mg, 27% yield) as orange solid. $^1$H NMR (300 MHz, DMSO-d6): δ=13.66 (s, 1H), 10.90 (s, 1H), 7.71-7.78 (m, 2H), 7.54-7.60 (m, 1H), 6.84-6.95 (m, 2H), 3.67-3.71 ((m, 1H), 3.45-3.51 (m, 2H), 3.31 (s, 3H), 2.38-2.40 (ds, 6H), 1.84-2.00 (m, 4H), 1.29-1.44 (t, 6H). LC/MS: 437.4 [M−H]$^+$.

Example 16

Preparation of 5-[5-Fluoro-2-oxo-1,2-dihydro-indol-(3Z)-ylidenemethyl]-2,4-dimethyl-1H-pyrrole-3-carboxylic acid (4-methanesulfonylamino-cyclohexyl)-amide

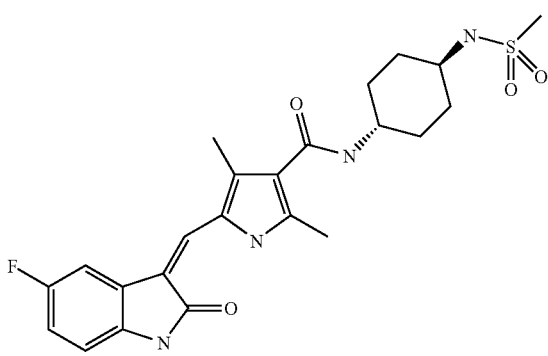

Follow the procedure of Example 15, the title compound was obtained (21 mg, 84% yield). $^1$H NMR (300 MHz, DMSO-d6): δ=13.66 (s, 1H), 10.87 (s, 1H), 7.71-7.77 (m, 2H), 7.52-7.56 (m, 1H), 6.82-7.02 (m, 3H), 3.63-3.66 (m, 1H), 3.07-3.12 (m, 1H), 2.92 (s, 3H), 2.36-2.38 (ds, 6H), 1.87-2.01 (m, 4H), 1.24-1.44 (m, 4H). LC/MS: 473.3 [M–H]$^+$.

Example 17

Preparation of 5-[5-Fluoro-2-oxo-1,2-dihydro-indol-(3Z)-ylidenemethyl]-2,4-dimethyl-1H-pyrrole-3-carboxylic acid (4-hydroxy-1,1-dioxo-tetrahydro-thiophen-3-yl)-amide

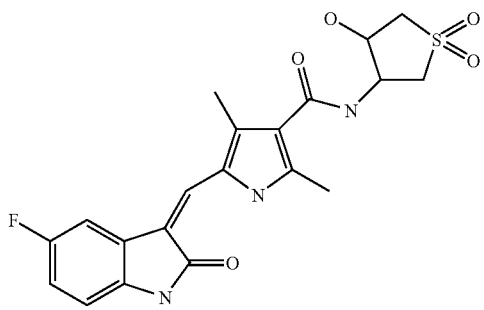

Preparation of 4-Amino-1,1-dioxo-tetrahydro-thiophen-3-ol

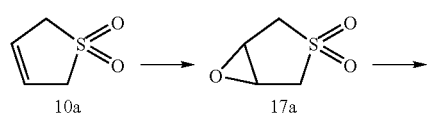

-continued

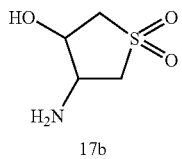

17b

Step 1: To a cooled solution of compound 10a (2 g, 16.9 mmol) in 11 mL of 88% formic acid was added 30% hydrogen peroxide (3 mL) dropwise. After addition, is the mixture was stirred for two days at r.t. Excess iron (II) sulfate heptahydrate (10 g) was added to consume the remaining hydrogen peroxide. The mixture was then evaporated under reduced pressure to remove most of the solvent. The resulting solid was collected by filtration, rinsed with water and dried in reduced pressure to provide compound 17a (0.6 g, 26%) as needles.

Step 2: Compound 17a (0.60 g, 4.48 mmol) was added to 26% aqueous ammonia hydroxide (15 mL) and the resulting mixture was allowed to stir overnight at r.t. A small amount of solid was filtered off and the filtrate was evaporated to dryness. The residue was triturated with ether, acetone and ethyl acetate, dried to provide compound 17b as white solid (205 mg, 30%).

Step 3: To the solution of A4 (150 mg, 0.36 mmol) in 20 mL of DMF, were added compound 17b (110 mg, 0.73 mmol) and DIEA (96 mg, 0.73 mmol), the reaction mixture was stirred at r.t. for several hours. LC/MS was applied to determine completion of the reaction. The reaction mixture was evaporated under reduced pressure and the residue was triturated with 5% diethylamine/methanol (25 mL) under sonication. The solid was collected by filtration and washed with methanol, dried under vacuum to provide title compound (110 mg, 71%) as orange solid. $^1$H NMR (300 MHz, DMSO-d6): δ=13.74 (s, 1H), 10.92 (s, 1H), 7.76-7.79 (m, 2H), 7.57-7.59 (d, 1H), 6.82-6.97 (m, 2H), 5.99-6.00 (d, 1H), 4.67-4.72 (m, 1H), 4.55 (s, 1H), 3.42-3.52 (m, 2H), 3.25-3.33 (m, 2H), 2.45-2.48 (ds, 6H). LC/MS: 432.0 [M–H]$^+$.

Example 18

Preparation of 5-[5-Fluoro-2-oxo-1,2-dihydro-indol-(3Z)-ylidenemethyl]-2,4-dimethyl-1H-pyrrole-3-carboxylic acid (1,1-dioxo-hexahydro-thiopyran-4-yl)-amide

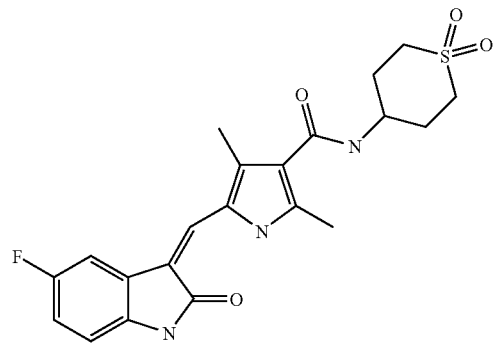

Preparation of 1,1-Dioxo-hexahydro-thiopyran-4-ylamine

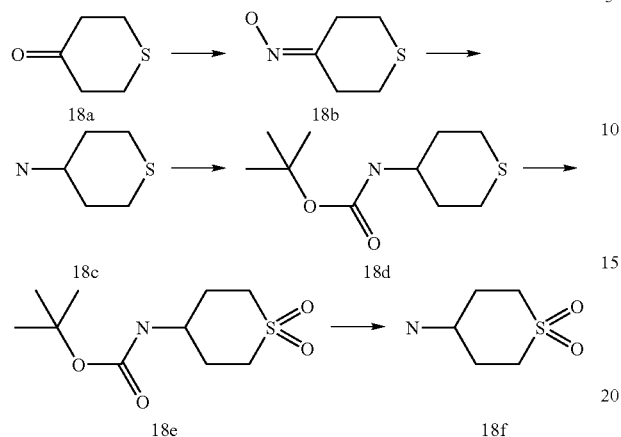

Step 1: To a solution of 18a (2.96 g, 25.5 mmol) in 23 mL of ethanol was added NH2OH.HCl (3.64 g, 51 mmol). The mixture was cooled to 0° C. in ice bath and was added a solution of NaOH (2.08 g) in 8 mL of H2O. With the addition of NaOH solution, precipitate was formed. The reaction mixture was warmed to r.t. and stirred for an additional 2 h, evaporated to remove ethanol. The aqueous solution was extracted with ether. The ether layer was washed with water and brine, dried over anhydrous Na2SO4. The organic layer was evaporated to dryness and the residue was recrystallized from hexane/ether to give compound 18b (1.81 g, 54%).

Step 2: To a mixture of LAH (2.84 g, 75 mmol) in 215 mL of THF was added a solution of compound 18b (1.81 g, 13.8 mmol) in 15 mL of THF with stirring under ice cooling. The resulting mixture was heated to reflux overnight. After cooling, the reaction mixture was added 9 mL of 2N aq.NaOH. The precipitate was filtered off and rinsed with THF for several times. The filtrate was concentrated to half volume and (Boc)2O (3.8 g, 17.4 mmol) was added drop-wise with stirring under ice cooling. The mixture was stirred at r.t. for 2 h, concentrated, diluted with ethyl acetate and washed with water. The organic layer was dried over anhydrous MgSO4 and evaporated to dryness. The solid residue was re-crystallized from hexane/ether to give compound 18d as white solid (2.45 g, 81%).

Step 3: To a solution of compound 18d (509 mg, 2.34 mmol) in 5 mL of THF was added 85% mCPBA (1.25 g, 6.15 mmol) with stirring under ice cooling. The resulting mixture was diluted with ethyl acetate and washed successively with saturated aq. NaHCO3, water and brine. The organic layer was dried over anhydrous MgSO4 and evaporated to dryness. The residue was re-crystallized from EA/hexane to give compound 18e as white solid (0.551 g, 94%). To a solution of 18e in DCM (15 mL) was added TFA (2.5 mL). The mixture was stirred for 0.5 h at r.t. and evaporated to give crude compound 18f (1.12 g) as yellow oil which was used in the next step without further purification.

Step 4: To the solution of A4 (107 mg, 0.256 mmol) in 10 mL of DMF solution, was added compound 18f (238 mg) and DIEA (133 mg, 1.03 mmol), the reaction mixture was stirred at r.t. for several hours. LC/MS was applied to determine completion of the reaction. DMF was evaporated under reduced pressure and the residue was precipitated with 5% diethylamine/methanol (25 mL) under sonication. The solid was collected by filtration and washed with methanol, dried under vacuum to provide title compound (102 mg, 92%) as orange solid. $^1$H NMR (300 MHz, DMSO-d6): δ=13.68 (s, 1H), 10.89 (s, 1H), 7.72-7.78 (m, 3H), 6.82-6.96 (m, 2H), 4.13-4.15 (m, 1H), 3.08-3.12 (d, 2H), 2.40-2.42 (ds, 6H), 1.97-2.16 (m, 4H). LC/MS: 430.3 [M−H]$^+$.

Example 19

Preparation of 5-[5-Fluoro-2-oxo-1,2-dihydro-indol-(3Z)-ylidenemethyl]-2,4-dimethyl-1H-pyrrole-3-carboxylic acid ((1S,2S)-2-hydroxy-cyclohexyl)-amide

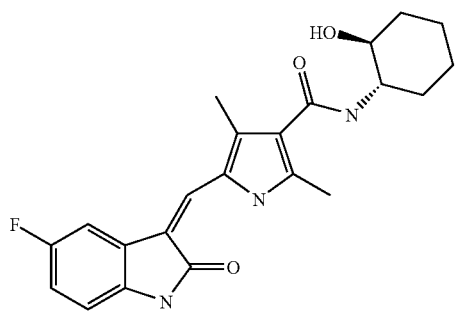

To the solution of A4 (100 mg, 0.24 mmol) and DIEA (140 mg, 0.96 mmol) in 10 mL of DMF, was added (1S,2S)-2-Amino-cyclohexanol (45 mg, 0.29 mmol). The reaction mixture was stirred at room temperature for several hours. LC/MS was applied to determine completion of the reaction. DMF was evaporated under reduced pressure and the residue was precipitated with 5% diethylamine/methanol (25 mL) under sonication. The solid was collected by filtration and washed with methanol), dried under vacuum to provide to provide title compound (70 mg, 74% yield) as orange solid. $^1$H NMR (300 MHz, DMSO-d6): δ=13.62 (s, 1H), 10.88 (s, 1H), 7.71-7.77 (m, 2H), 7.36-7.39 (d, 1H), 6.81-6.95 (m, 2H), 4.58-4.60 (d, 1H), 3.48-3.60 (m, 1H), 3.30-3.35 (m, 1H), 2.41-2.44 (ds, 6H), 1.88-1.90 (t, 2H), 1.62 (S, 2 h), 1.23 (s, 4H). LC/MS: 398.1 [M+H]$^+$.

Example 20

Preparation of 5-[5-Fluoro-2-oxo-1,2-dihydro-indol-(3Z)-ylidenemethyl]-2,4-dimethyl-1H-pyrrole-3-carboxylic acid ((S)-6-oxo-piperidin-3-yl)-amide

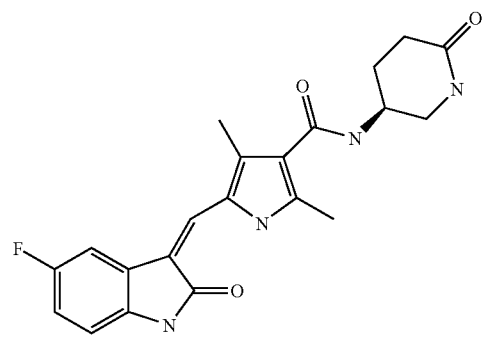

The synthesis of the title compound is similar to that of Example 19 (19.1% yield): ¹H NMR (300 MHz, DMSO-d6): δ=13.71 (s, 1H), 10.92 (s, 1H), 7.95-7.98 (d, 1H), 7.72-7.79 (m, 2H), 6.82-6.96 (m, 2H), 4.92-4.96 (q, 1H), 4.53-4.89 (t, 1H), 3.96-4.02 (q, 1H), 2.39-2.43 (ds, 6H), 1.88-1.90 (t, 2H), 1.62 (S, 2 h), 1.23 (s, 4H). LC/MS: 383.2 $[M-H]^+$.

Example 21

Preparation of 5-[5-Fluoro-2-oxo-1,2-dihydro-indol-(3Z)-ylidenemethyl]-2,4-dimethyl-1H-pyrrole-3-carboxylic acid ((2S,3S,4R,5S,6S)-3,4,5-trihydroxy-6-hydroxymethyl-tetrahydro-pyran-2-yl)-amide

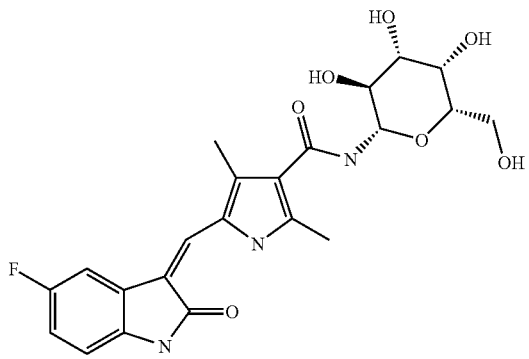

The synthesis of the title compound is similar to that of Example 19 (36.7% yield): ¹H NMR (300 MHz, DMSO-d6): δ=13.68 (s, 1H), 10.88 (s, 1H), 7.95-7.97 (d, 1H), 7.71-7.78 (m, 2H), 6.82-6.96 (m, 2H), 4.84-4.90 (t, 1H), 4.70-4.75 (m, 2H), 4.56-4.57 (m, 1H), 4.38-4.39 (d, 1H), 3.71-3.73 (t, 1H), 3.29-3.55 (m, 5H), 2.44-2.47 (ds, 6H). LC/MS: 462.1 $[M+H]^+$.

Example 22

Preparation of 5-[5-Fluoro-2-oxo-1,2-dihydro-indol-(3Z)-ylidenemethyl]-2,4-dimethyl-1H-pyrrole-3-carboxylic acid [1-(2-hydroxy-acetyl)-piperidin-4-yl]-amide

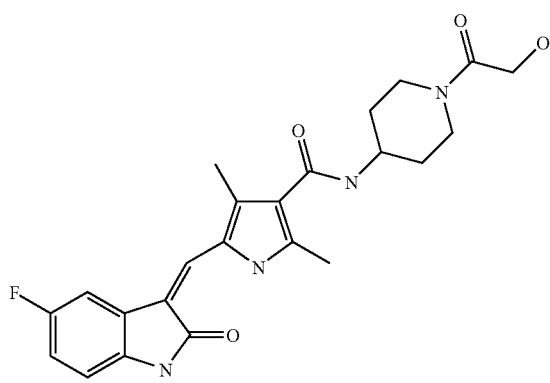

Preparation of 1-(4-Amino-piperidin-1-yl)-2-hydroxy-ethanone

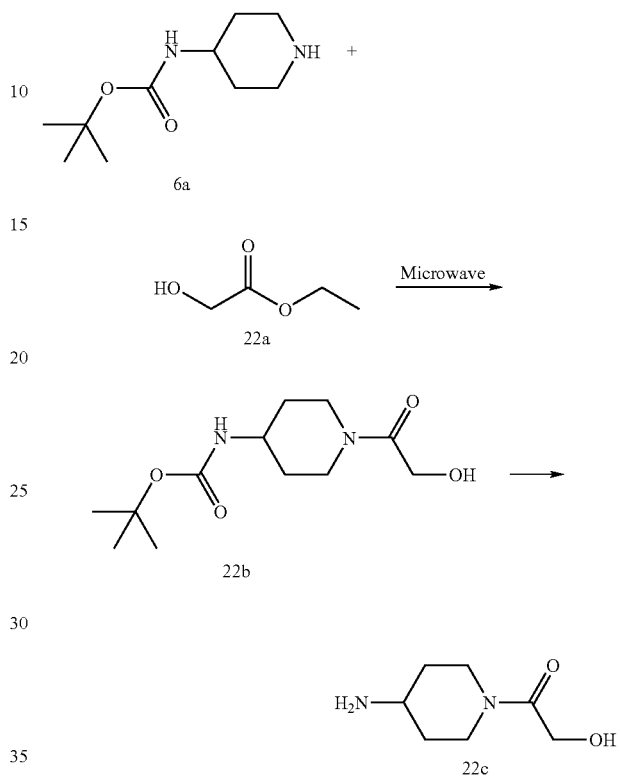

Step 1: Compound 6a (2.12 g, 10.6 mmol) and compound 22a (1.0 g) were placed into a microwave reactor. The resulting mixture was reacted at 160° C. for 30 min. The mixture was evaporated and purified by column chromatography (EA: PE=1:1) to provide compound 22b (1.3 g).

Step 2: To a solution of compound 22b (1.3 g, 5 mmol) in DCM (20 mL), was added TFA (6 mL). The resulting mixture was stirred at r.t. for about 1 h and evaporated which was used for the next step without further purification.

Step 3: To the solution of A4 (200 mg, 0.478 mmol) and DIEA (0.2 mL, 1.15 mmol) in 25 mL of DMF, was added compound 22c (91 mg, 0.57 mmol). The reaction mixture was stirred at room temperature for several hours. LC/MS detection was applied to determine completion of the reaction. DMF was evaporated under reduced pressure and the residue was precipitated with 5% diethylamine/methanol (10 mL) under sonication. The solid was collected by filtration and washed with methanol, dried under vacuum to provide title compound (180 mg, 86.9%). ¹H NMR (300 MHz, DMSO-d6): δ=13.68 (s, 1H), 10.88 (s, 1H), 7.62-7.78 (m, 3H), 6.82-6.96 (m, 2H), 4.48-4.52 (t, 1H), 4.22-4.23 (d, 1H), 3.97-4.10 (m, 3H), 3.65-3.69 (d, 1H), 3.03-3.12 (t, 1H), 2.49-2.51 (t, 1H), 2.37-2.40 (ds, 6H), 1.80-1.83 (t, 2H), 1.36-1.46 (m, 2H). LC/MS: 439.3 $[M-H]^+$.

Example 23

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-acetyl)-pyrrolidin-3-yl]-amide

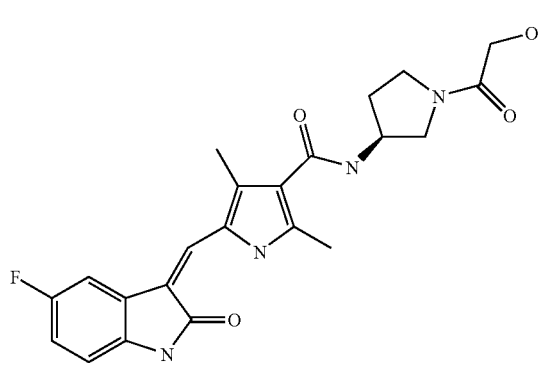

Preparation of 1-((S)-3-Amino-pyrrolidin-1-yl)-2-hydroxy-ethanone

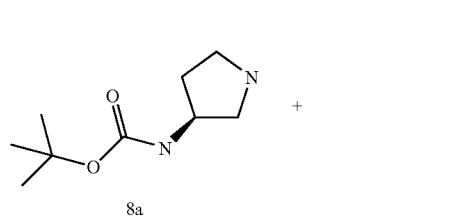

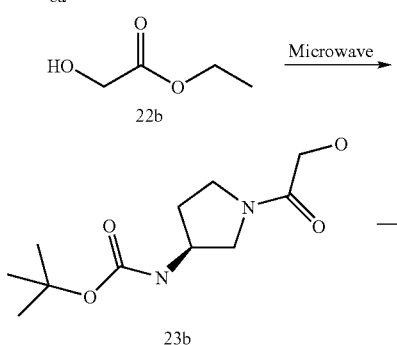

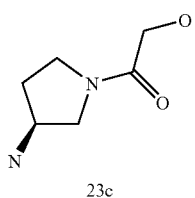

Follow the preparation of Compound 22c, Compound 23c was prepared. The title compound was prepared following Example 22 (85.4% yield): $^1$H NMR (300 MHz, DMSO-d6): δ=13.66 (s, 1H), 10.86 (s, 1H), 7.70-7.89 (m, 3H), 6.80-6.94 (m, 2H), 4.37-4.54 (m, 2H), 3.95-4.00 (t, 2H), 3.57-3.63 (m, 1H), 3.35-3.50 (m, 1H), 2.13-2.14 (ds, 6H), 1.86-1.93 (m, 4H). LC/MS: 425.4 [M−H]$^+$.

Example 24

Preparation of 5-[5-Fluoro-2-oxo-1,2-dihydro-indol-(3Z)-ylidenemethyl]-2,4-dimethyl-1H-pyrrole-3-carboxylic acid (4-hydroxy-tetrahydro-furan-3-yl)-amide

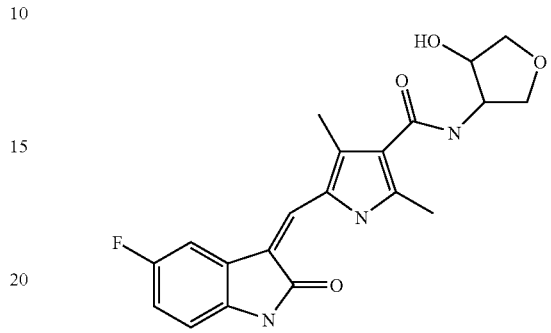

Preparation of 4-Amino-tetrahydro-furan-3-ol

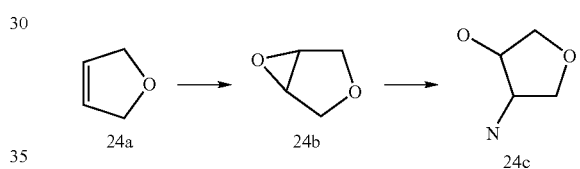

Step 1: To the solution of 24a (5.04 g, 0.072 mol) in 150 mL of DCM was added 85% mCPBA (18.86 g, 0.093 mol) at 0° C. using ice-water bath. The mixture was stirred over weekend at r.t. and the precipitate was filtered off. The filtrated was washed successfully with saturated aqueous NaHCO3, water and brine. The organic layer was dried over anhydrous Na2SO4 and concentrated to give a mixture of white solid and yellow oil (5.24 g, 84.6%).

Step 2: A mixture of crude 24b (300 mg, 3.49 mmol) obtained from last step, i-PrOH (3 mL) and 26% NH4OH (10 mL) was heated at a sealed tube at 80° C. for 18 hs. A small amount of solid was filtered off and the filtrate was evaporated to give the crude 24c (0.348 g, 96.8%).

Step 3: To the solution of A4 (199 mg, 0.476 mmol) in 20 mL of DMF was added compound 24c (0.348 g, 3.378 mmol), the reaction mixture was stirred at room temperature for several hours. LC/MS detection was applied to determine completion of the reaction. DMF was evaporated under reduced pressure and the residue was precipitated with 5% diethylamine/methanol (10 mL). The slurry was then placed in a refrigerator overnight and concentrated to remove most of the solvents. The resulting yellow slurry was added ethanol and concentrated to remove most of the solvent. The resulting yellow slurry was then placed into a refrigerator for an hour and the precipitate was collected by filtration, washed with ethanol and dried in vacuum to give title compound as an orange solid (170 mg, 93% yield). ¹H NMR (300 MHz, DMSO-d6): δ=13.67 (s, 1H), 10.88 (s, 1H), 7.71-7.78 (m, 3H), 6.82-6.96 (m, 2H), 5.25-5.27 (d, 1H), 4.14-4.19 (r, 2H), 3.96-4.00 (q, 1H), 3.86-3.90 (q, 1H), 3.52-3.63 (m, 2H), 2.39-2.41 (ds, 6H). LC/MS: 384.3 [M+H]⁺.

Example 25

Preparation of 5-[5-Fluoro-2-oxo-1,2-dihydro-indol-(3Z)-ylidenemethyl]-2,4-dimethyl-1H-pyrrole-3-carboxylic acid ((S)-2-oxo-pyrrolidin-3-yl)-amide

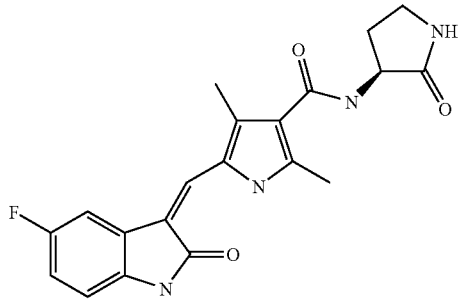

Preparation of (S)-3-Amino-pyrrolidin-2-one

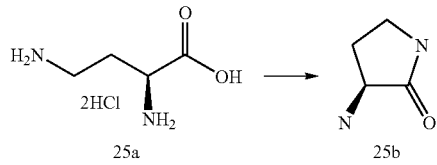

Step 1: HMDS (67 mL, 0.32 mmol) in ACN (50 mL) was added dropwise to a solution of 25a (5 g, 32 mmol) in ACN (50 mL) at room temperature. The resulting mixture was heated to reflux for 48 h under the protection of N2. When the reaction was complete, the mixture was cooled, poured into cold methanol (50 mL) and stirred for 30 min. The obtained mixture was evaporated to dryness and the residue was extracted with chloroform (150 mL*3) under reflux. The combined chloroform solution was evaporated to provide crude 25b (3.1 g, 96%).

Step 2: To the solution of A4 (334 mg, 0.8 mmol) and DIEA (1 mL) in 20 mL of DMF was added 25b (120 mg, 1.28 mmol). The reaction mixture was stirred at room temperature for several hours. LC/MS was applied to determine completion of the reaction. DMF was evaporated under reduced pressure and the residue was precipitated with 5% diethylamine/methanol (10 mL). The precipitate was collected by filtration, washed with ethanol and dried in vacuum to give title compound as an orange solid (83 mg, 27% yield). ¹H NMR (300 MHz, DMSO-d6): δ=13.68 (s, 1H), 10.89 (s, 1H), 7.71-7.82 (m, 4H), 6.82-6.96 (m, 2H), 4.47-4.56 (q, 1H), 3.18-3.25 (m, 2H), 2.42-2.45 (ds, 6H), 2.27-2.39 (m, 1H), 1.92-2.00 (q, 1H). LC/MS: 383.0 [M+H]⁺.

Example 26

Preparation of 5-[5-Fluoro-2-oxo-1,2-dihydro-indol-(3Z)-ylidenemethyl]-2,4-dimethyl-1H-pyrrole-3-carboxylic acid (1-benzyl-4-hydroxy-pyrrolidin-3-yl)-amide

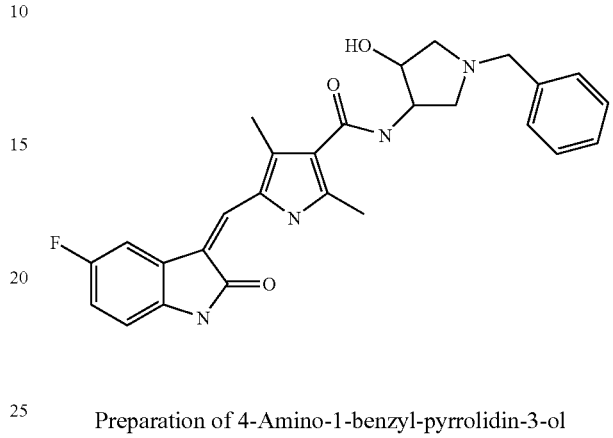

Preparation of 4-Amino-1-benzyl-pyrrolidin-3-ol

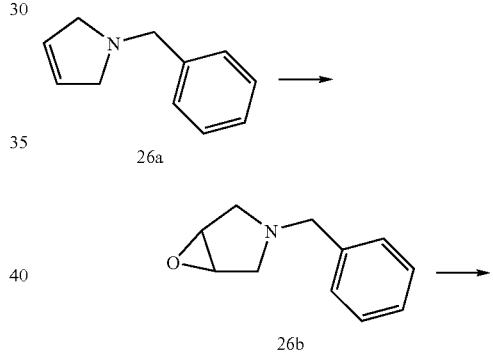

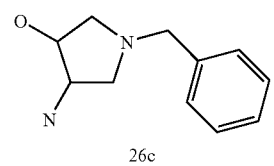

Step 1: To an ice-cooled solution of 26a (4.77 g, 30 mmol), 98% H2SO4 (1.95 mL), H2O (4.5 mL) and acetone (30 mL) was added 85% mCPBA (7.91 g, 39 mmol) with stirring. The mixture was allowed to react for 48 hrs at r.t. Acetone was evaporated and the mixture was neutralized with 1N aq. NaOH and extracted with toluene. The organic phase was dried over anhy. MgSO4 and evaporated. The residue was purified by column chromatography (EA:PE=1:4) to provide 26b (2.0 g, 38%).

Step 2: A mixture of 26b (618 mg, 3.53 mmol) in 10 mL of 26% ammonium hydroxide was heated in a sealed tube at 110° C. for 24 hrs. A small amount of solid was filtered off and the filtrate was evaporated to give the crude 26c (630 mg, 93% yield).

Step 3: To the solution of A4 (493 mg, 1.18 mmol) in 50 mL of DMF was added compound 26c (0.455 mg, 2.37 mmol), the reaction mixture was stirred at room temperature for several hours. LC/MS was applied to determine completion of the reaction. DMF was evaporated under reduced pressure and the residue was precipitated with 5% diethylamine/methanol. The precipitate was collected by filtration, washed with ethanol and dried in vacuo to give title compound (517 mg, 92.5% yield) an orange solid. $^1$H NMR (300 MHz, DMSO-d6): δ=13.66 (s, 1H), 10.87 (s, 1H), 7.71-7.17 (m, 3H), 7.22-7.32 (m, 5H), 6.82-6.95 (m, 2H), 5.03-5.05 (d, 1H), 4.06-4.15 (m, 2H), 3.50-3.64 (q, 2H), 2.82-2.89 (m, 2H), 2.35-2.41 (m, 8H). LC/MS: 475.2 [M+H]$^+$.

Example 27

Preparation of 5-[5-Fluoro-2-oxo-1,2-dihydro-indol-(3Z)-ylidenemethyl]-2,4-dimethyl-1H-pyrrole-3-carboxylic acid (1-acetyl-4-hydroxy-pyrrolidin-3-yl)-amide

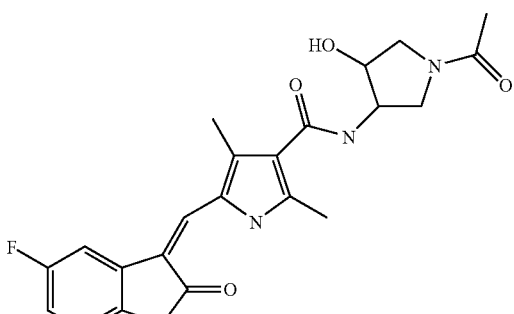

A mixture of Example 26 (283.7 mg, 0.59 mmol), 10% Pd/C (282 mg) and acetic acid (3 drops) in 30 mL of [DMF:MeOH=1:1] was stirred at r.t. under H2 atmosphere. After the reaction was complete as detected by LC/MS, the catalyst was filtered off and the filtrate was evaporated to dryness. The residue was triturated with ethanol to provide 5-[5-Fluoro-2-oxo-1,2-dihydro-indol-(3Z)-ylidenemethyl]-2,4-dimethyl-1H-pyrrole-3-carboxylic acid (4-hydroxy-pyrrolidin-3-yl)-amide (178 mg, 67%).

To the solution of 5-[5-Fluoro-2-oxo-1,2-dihydro-indol-(3Z)-ylidenemethyl]-2,4-dimethyl-1H-pyrrole-3-carboxylic acid (4-hydroxy-pyrrolidin-3-yl)-amide (150 mg, 0.39 mmol) and DIEA (89 mg, 0.69 mmol) was added CH3COCl (33.7 mg, 0.43 mmol) on an ice bath. The mixture was stirred at r.t. for 3 hrs. After the reaction was complete, DMF was evaporated under reduced pressure and the residue was triturated with methanol and the solid was collected by filtration, washed with ethanol and dried in vacuum to give title compound (82 mg, 57% yield) as an orange solid. $^1$H NMR (300 MHz, DMSO-d6): δ=13.67 (s, 1H), 10.87 (s, 1H), 8.07-8.10 (d, 1H), 7.71-7.85 (m, 3H), 6.82-6.92 (m, 2H), 5.34-5.44 (dd, 1H), 4.13-4.18 (d, 2H), 3.67-3.81 (m, 4H), 2.38-2.40 (ds, 6H), 1.92-1.93 (d, 3H). LC/MS: 427.0 [M+H]$^+$.

Example 28

Preparation of 5-[5-Fluoro-2-oxo-1,2-dihydro-indol-(3Z)-ylidenemethyl]-2,4-dimethyl-1H-pyrrole-3-carboxylic acid (1-dimethylaminooxalyl-piperidin-4-yl)-amide

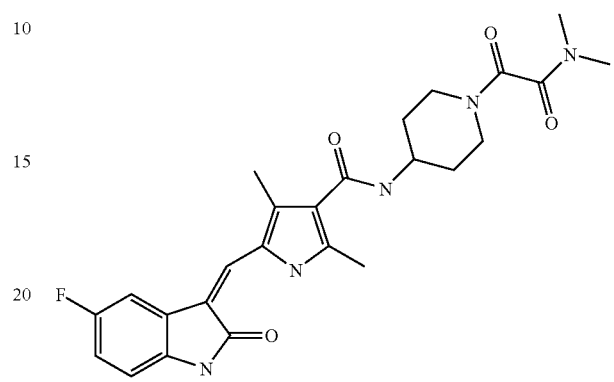

Preparation of 2-(4-Amino-piperidin-1-yl)-N,N-dimethyl-2-oxo-acetamide

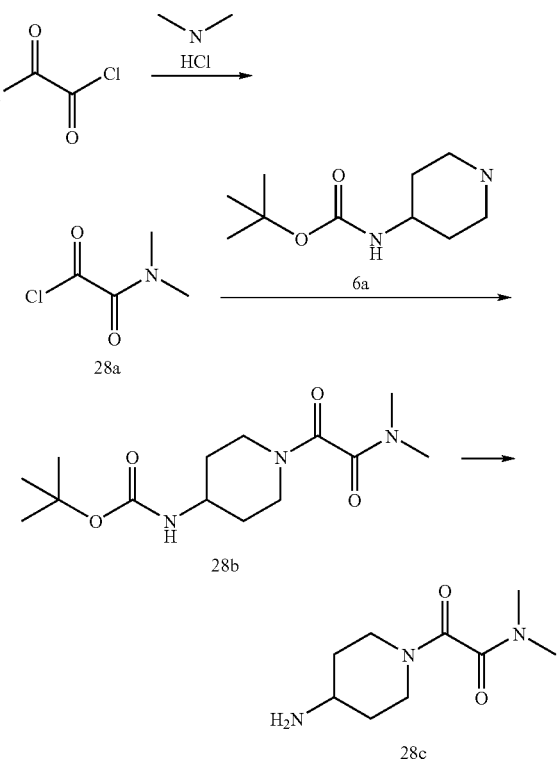

Step 1: DIEA (0.87 mL, 5 mmol) was added to an ice-cooled solution of oxalyl chloride (0.22 mL, 2.5 mmol) and dimethylamine (0.204 g, 2.5 mmol) in 30 mL of THF. The mixture was stirred at r.t. for 1 h which was used for the next step directly.

Step 2: Compound 6a (0.5 g, 2.5 mmol) was added to the above solution, followed by DIEA (0.87 ml, 5 mmol). The resulting mixture was stirred at r.t. overnight and evaporated. The residue was purified by column chromatography to provide 28b (307 mg, 41%).

Step 3: To a solution of compound 28b (172 mg, 0.57 mmol) in 5 mL of DCM was added TFA (0.66 mL, 8.6 mmol). The resulting mixture was stirred at r.t. for ca. 1 h and evaporated. The residue was added to a solution of A4 (159 mg, 0.38 mmol) and DIEA (1 mL) in 20 mL of DMF. The reaction mixture was stirred at room temperature for several hours. LC/MS was applied to determine completion of the reaction. DMF was evaporated under reduced pressure and the residue was precipitated with 5% diethylamine/methanol (10 mL). The precipitate was collected by filtration, washed with methanol and dried in vacuum to give an orange solid (169 mg, 92.5% yield): $^1$H NMR (300 MHz, DMSO-d6): δ=13.68 (s, 1H), 10.89 (s, 1H), 7.64-7.78 (m, 3H), 6.82-6.96 (m, 2H), 4.03-4.23 (m, 2H), 3.38-3.49 (m, 1H), 3.16-3.29 (m, 1H), 2.87-2.99 (m, 7H), 2.39-2.42 (ds, 6H), 1.87-1.90 (m, 2H), 1.40-1.49 (m, 2H). LC/MS: 482.1 [M+H]$^+$.

Example 29

Preparation of 5-[5-Fluoro-2-oxo-1,2-dihydro-indol-(3Z)-ylidenemethyl]-2,4-dimethyl-1H-pyrrole-3-carboxylic acid ((S)-1-dimethylaminooxalyl-pyrrolidin-3-yl)-amide

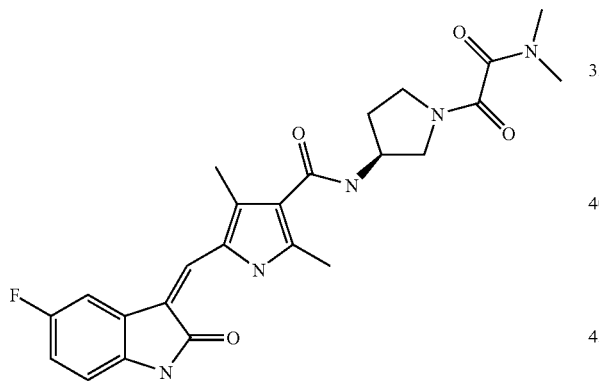

Preparation of 2-((S)-3-Amino-pyrrolidin-1-yl)-N,N-dimethyl-2-oxo-acetamide (29b) is similar to that of 28c

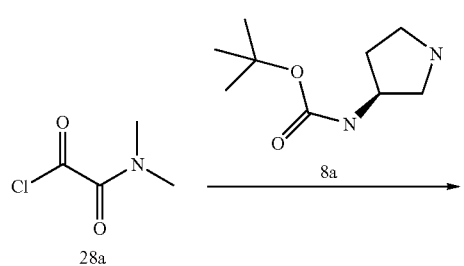

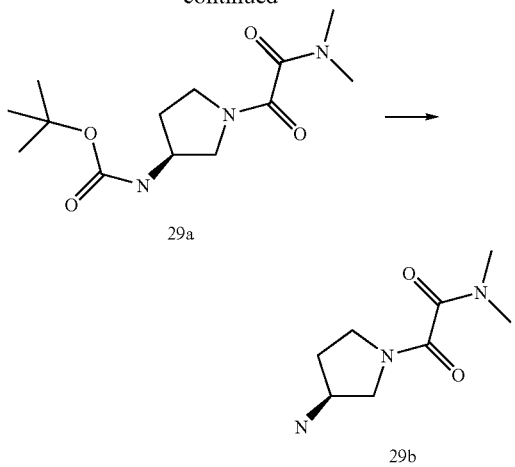

The synthesis of the title compound is similar to that of Example 28 (32 mg, 53.9% yield). $^1$H NMR (300 MHz, DMSO-d6): δ=13.67-13.68 (d, 1H), 10.87 (s, 1H), 7.71-7.92 (m, 3H), 6.82-6.93 (m, 2H), 4.40-4.47 (m, 1H), 3.39-3.62 (m, 4H), 2.86-2.92 (dd, 6H), 2.39-2.41 (dd, 6H), 2.15-2.18 (m, 1H), 1.94-2.13 (m, 1H). LC/MS: 466.4 [M−H]$^+$.

Example 30

Preparation of 5-[5-Fluoro-2-oxo-1,2-dihydro-indol-(3Z)-ylidenemethyl]-2,4-dimethyl-1H-pyrrole-3-carboxylic acid [4-(morpholine-4-carbonyl)-cyclohexyl]-amide

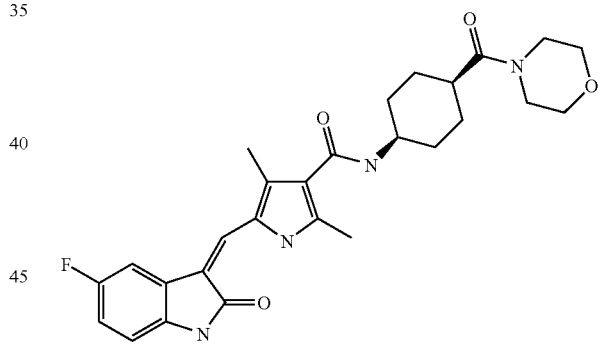

Step 1: 4-Amino-cyclohexanecarboxylic acid (84 mg, 0.573 mmol) was added to a solution of A4 (200 mg, 0.478 mmol) and DIEA (0.125 mL, 0.717 mmol) in 15 mL of DMF. The mixture was stirred at r.t. LC-MS was used to determine completion of the reaction. DMF was evaporated under reduced pressure and the residue was triturated with ACN for several times to provide 4-({5-[5-Fluoro-2-oxo-1,2-dihydro-indol-(3Z)-ylidenemethyl]-2,4-dimethyl-1H-pyrrole-3-carbonyl}-amino)-cyclohexanecarboxylic acid (180 mg, 88.5%).

Step 2: To the solution of 4-({5-[5-Fluoro-2-oxo-1,2-dihydro-indol-(3Z)-ylidenemethyl]-2,4-dimethyl-1H-pyrrole-3-carbonyl}-amino)-cyclohexanecarboxylic acid in 20 mL of DMF were added HATU (0.161 g, 0.424 mmol), DIEA (0.072 mL, 0.424 mmol) and morpholine (0.0737 g, 0.847 mmol). The reaction mixture was stirred at r.t. overnight. LC-MS was used to determine completion of the reaction. DMF was evaporated under reduced pressure and the residue was precipitated with 5% diethyl amine/methanol (5 mL). The precipitate was collected by filtration, washed with methanol and dried in vacuum to give title compound (69 mg, 32.9% yield) as an orange solid. $^1$H NMR (300 MHz, DMSO-d6): δ=13.66 (s, 1H), 10.87 (s, 1H), 7.71-7.77 (m, 2H), 7.53-7.55 (d, 1H), 6.81-6.92 (m, 2H), 3.95-3.96 (m, 1H), 3.29-3.54 (m, 8H), 2.64-2.67 (m, 1H), 2.39-2.41 (ds, 6H), 1.47-1.88 (m, 8H). LC/MS: 495.1 [M+H]$^+$.

Example 31

Preparation of 5-[5-Fluoro-2-oxo-1,2-dihydro-indol-(3Z)-ylidenemethyl]-2,4-dimethyl-1H-pyrrole-3-carboxylic acid [4-(pyrrolidine-1-carbonyl)-cyclohexyl]-amide

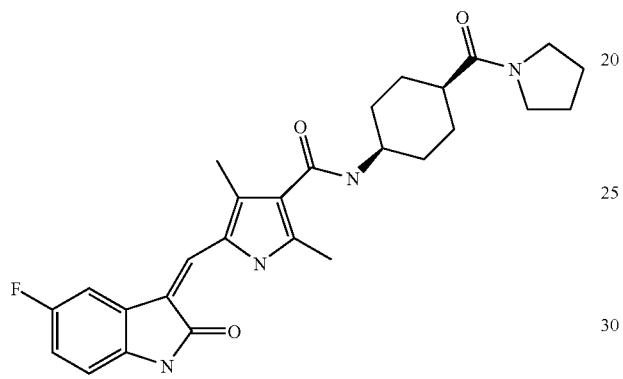

The synthesis of the title compound is similar to that of Example 30 (92 mg, 67.8% yield): 1H NMR (300 MHz, DMSO-d6): δ=13.64 (s, 1H), 10.86 (s, 1H), 7.70-7.76 (m, 2H), 7.52-7.55 (d, 1H), 6.80-6.94 (m, 2H), 3.93-3.95 (m, 1H), 3.41-3.46 (m, 2H), 3.22-3.28 (m, 3H), 2.40-2.42 (ds, 6H), 1.68-1.90 (m, 8H), 1.45-1.60 (m, 4H). LC/MS: 479.1 [M+H]$^+$.

Example 32

Preparation of 5-[5-Fluoro-2-oxo-1,2-dihydro-indol-(3Z)-ylidenemethyl]-2,4-dimethyl-1H-pyrrole-3-carboxylic acid [4-(aziridine-1-carbonyl)-cyclohexyl]-amide

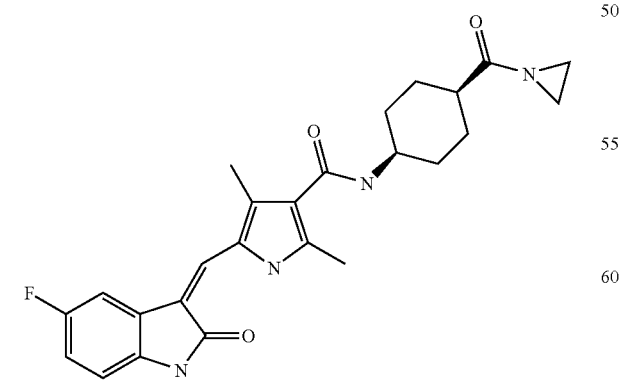

The synthesis of the title compound is similar to that of Example 30: LC/MS: 449.3 [M−H]$^+$.

Example 33

Preparation of 5-[5-Fluoro-2-oxo-1,2-dihydro-indol-(3Z)-ylidenemethyl]-2,4-dimethyl-1H-pyrrole-3-carboxylic acid [(1R,3S)-3-(pyrrolidine-1-carbonyl)-cyclopentyl]-amide

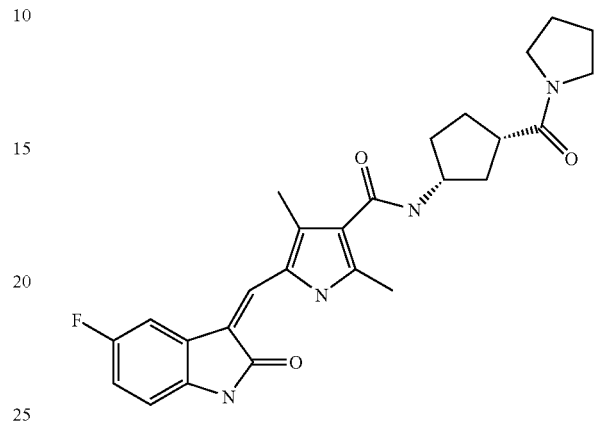

The synthesis of the title compound is similar to that of Example 30: $^1$H NMR (300 MHz, DMSO-d6): δ=13.68 (s, 1H), 10.88 (s, 1H), 7.71-7.80 (m, 3H), 6.81-6.95 (m, 2H), 4.29-4.31 (m, 1H), 3.38-3.0 (m, 2H), 3.17-3.30 (m, 2H), 3.01-3.06 (m, 1H), 2.42-2.43 (ds, 6H), 1.65-2.08 (m, 10H). LC/MS: 465.2 [M+H]$^+$.

Example 34

Preparation of 5-[5-Fluoro-2-oxo-1,2-dihydro-indol-(3Z)-ylidenemethyl]-2,4-dimethyl-1H-pyrrole-3-carboxylic acid [(1R,3S)-3-(morpholine-4-carbonyl)-cyclopentyl]-amide

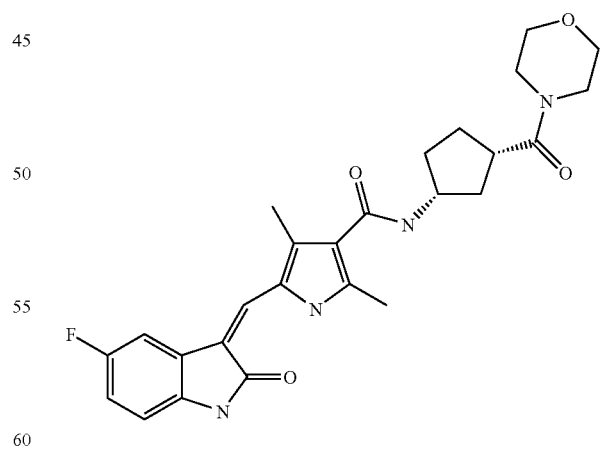

The synthesis of the title compound is similar to that of Example 30: $^1$H NMR (300 MHz, DMSO-d6): δ=13.68 (s, 1H), 10.88 (s, 1H), 7.64-7.78 (m, 3H), 6.81-6.95 (m, 2H), 4.25-4.31 (m, 1H), 3.38-3.55 (m, 8H), 3.14-3.19 (m, 1H), 2.41-2.42 (ds, 6H), 1.62-2.08 (m, 10H). LC/MS: 481.2 [M+H]$^+$.

Example 35

Preparation of 5-[5-Fluoro-2-oxo-1,2-dihydro-indol-(3Z)-ylidenemethyl]-2,4-dimethyl-1H-pyrrole-3-carboxylic acid [(1R,3S)-3-(aziridine-1-carbonyl)-cyclopentyl]-amide The synthesis of the title compound is similar to that of Example 30: LC/MS: 435.2 [M–H]+.

Example 36

Preparation of 5-[5-Fluoro-2-oxo-1,2-dihydro-indol-(3Z)-ylidenemethyl]-2,4-dimethyl-1H-pyrrole-3-carboxylic acid [(1R,2S)-2-(pyrrolidine-1-carbonyl)-cyclopentyl]-amide

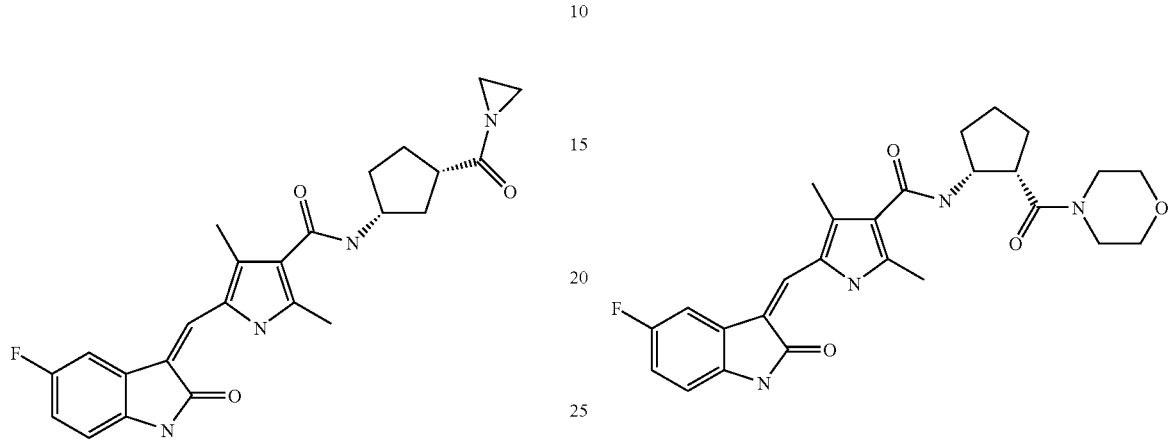

The synthesis of the title compound is similar to that of Example 30: $^1$H NMR (300 MHz, DMSO-d6): δ=13.67 (s, 1H), 10.88 (s, 1H), 7.70-7.77 (m, 2H), 7.40-7.42 (d, 2H), 6.82-6.93 (m, 2H), 4.52-4.61 (m, 1H), 3.62-3.70 (m, 2H), 3.42-3.51 (m, 1H), 3.09-3.30 (m, 3H), 2.38-2.41 (ds, 6H), 1.49-1.98 (m, 10H). LC/MS: 465.1 [M+H]+.

Example 37

Preparation of 5-[5-Fluoro-2-oxo-1,2-dihydro-indol-(3Z)-ylidenemethyl]-2,4-dimethyl-1H-pyrrole-3-carboxylic acid [(1R,2S)-2-(morpholine-4-carbonyl)-cyclopentyl]-amide The synthesis of the title compound is similar to that of Example 30: $^1$H NMR (300 MHz, DMSO-d6): δ=13.67 (s, 1H), 10.88 (s, 1H), 7.70-7.77 (m, 2H), 7.30-7.33 (d, 1H), 6.81-6.93 (m, 2H), 4.56-4.63 (m, 1H), 3.37-3.60 (m, 8H), 3.21-3.27 (m, 1H), 2.38-2.42 (ds, 6H), 1.45-2.06 (m, 6H). LC/MS: 481.1 [M+H]+.

Example 38

Preparation of 5-[5-Fluoro-2-oxo-1,2-dihydro-indol-(3Z)-ylidenemethyl]-2,4-dimethyl-1H-pyrrole-3-carboxylic acid [(1R,2S)-2-(aziridine-1-carbonyl)-cyclopentyl]-amide

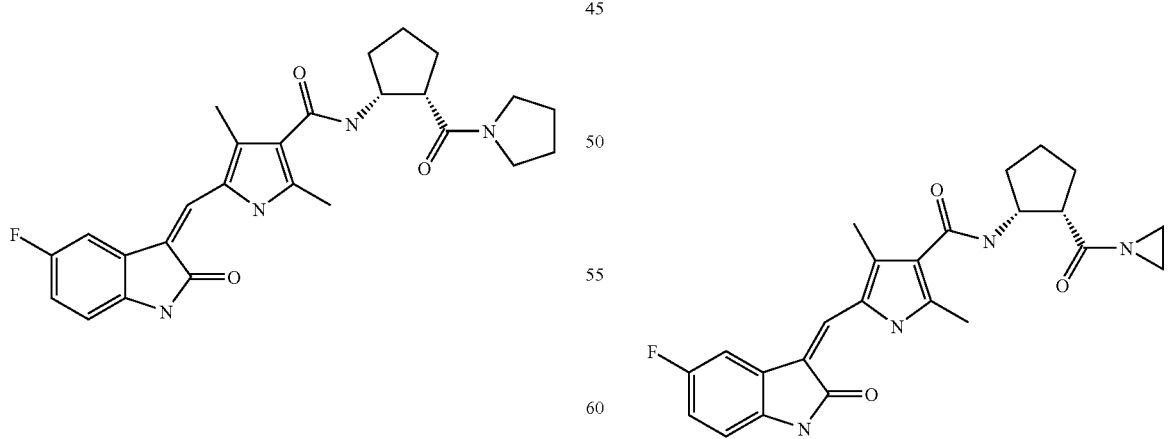

The synthesis of the title compound is similar to that of Example 30: LC/MS: 435.3 [M–H]+.

Example 39

Preparation of 5-[5-Fluoro-2-oxo-1,2-dihydro-indol-(3Z)-ylidenemethyl]-2,4-dimethyl-1H-pyrrole-3-carboxylic acid ((2S,3S,4R,5S)-3,4-dihydroxy-5-hydroxymethyl-tetrahydro-furan-2-yl)-amide

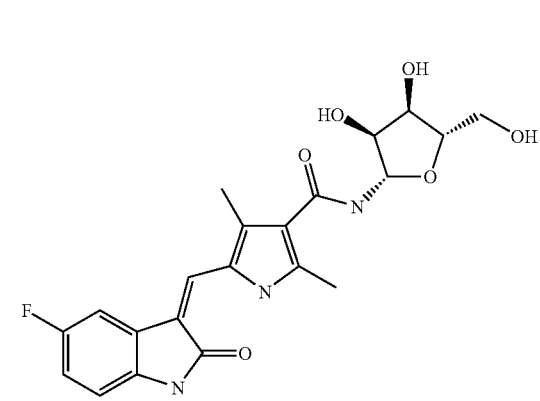

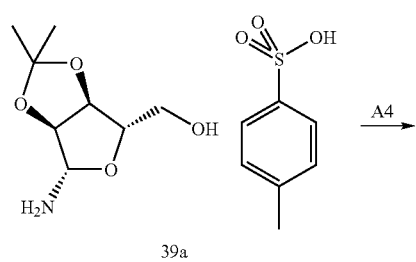

39a

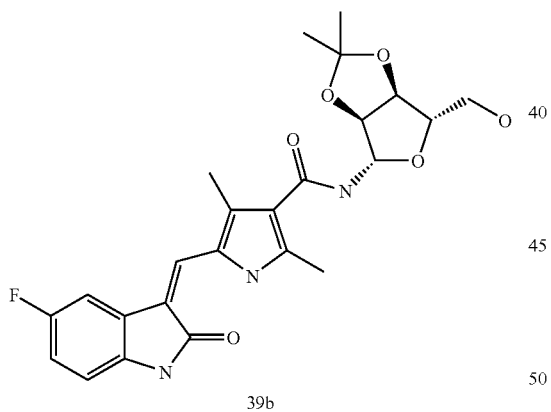

39b

To the solution of A4 (200 mg, 0.478 mmol) and DIEA (1 mL) in 20 mL of DMF was added compound 39a (225 mg, 0.623 mmol), the reaction mixture was stirred at room temperature for several hours. LC/MS detection was applied to determine completion of the reaction. DMF was evaporated under reduced pressure and the residue was precipitated with 5% diethylamine/methanol (10 mL). The precipitate was collected by filtration, washed with Methanol and dried in vacuum to give crude 39b which was dissolved in 5 ml 95% TFA at r.t. for 0.5 h. The mixture was then evaporated to dryness and the residue was triturated with methanol for several times to provide title compound (89 mg, 43% yield). LC/MS: 432.2[M+H]$^+$.

Example 40

Preparation of 5-[5-Fluoro-2-oxo-1,2-dihydro-indol-(3Z)-ylidenemethyl]-2,4-dimethyl-1H-pyrrole-3-carboxylic acid ((S)-1-carbamoylmethyl-2-oxo-pyrrolidin-3-yl)-amide

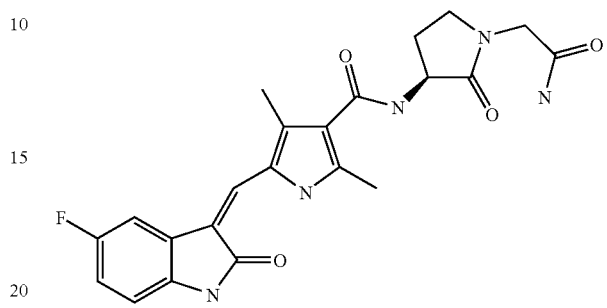

Preparation of 2-((S)-3-Amino-2-oxo-pyrrolidin-1-yl)-acetamide

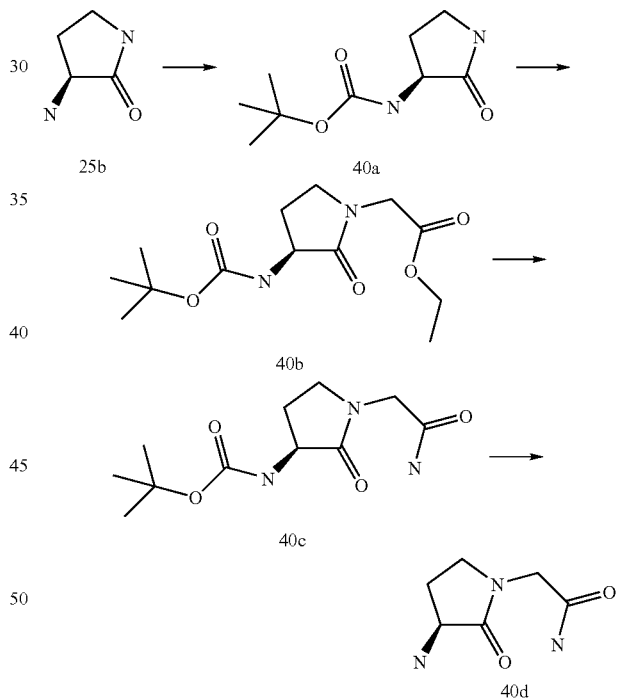

Step 1: To a solution of 25b (3.1 g, 32 mmol) in methanol (130 mL) was added TEA (16 mL) and (Boc)2O (7.7 g, 35.2 mmol) at room temperature. The mixture was stirred overnight at room temperature, followed by refluxing for 2 h. Solvent was removed and the residue was purified by column chromatography (EA) to provide 40a (5.0 g, 78%) as white solid.

Step 2: To a solution of 40a (700 mg, 3.5 mmol) in THF (50 mL) was added 60% NaH (560 mg, 14 mmol) at 0° C. After stirring for 1 h at 0° C., ethyl bromoacetate (700 mg, 4.2 mmol) was added and the mixture was stirred at room temperature overnight. After the reaction was complete, the mixture was diluted by EA (50 mL) and quenched by brine (50 mL). The organic and aqueous layers were separated. The aqueous layer was extracted by EA (50 mL*3). The combined EA phase was dried by anhydrous Na2SO4 and evaporated to provide the crude 40b (1.0 g, 99%).

Step 3: Gas NH3 was bubbled for 1 h into a solution of 40b (0.27 g, 0.94 mmol) in MeOH (20 mL). The solution was kept under stirring at r.t. for 24 hs. The solvent was evaporated and the residue was purified by column chromatography to provide 40c (170 mg, 70.3%). To a solution of compound 40c (160 mg, 0.62 mmol) in 5 mL of DCM, was added TFA (0.66 mL, 8.6 mmol). The resulting mixture was stirred at r.t. for about 1 h and evaporated. The residue was added to a solution of A4 (172 mg, 0.41 mmol) and DIEA (0.22 mL, 1.23 mmol) in 20 mL of DMF. The reaction mixture was stirred at room temperature for several hours. LC/MS was applied to determine completion of the reaction. DMF was evaporated under reduced pressure and the residue was precipitated with 5% diethylamine/methanol (10 mL). The precipitate was collected by filtration, washed with ethanol and dried in vacuum to give title compound as an orange solid (136 mg, 75.3% yield). $^1$H NMR (300 MHz, DMSO-d6): δ=13.71 (s, 1H), 10.92 (s, 1H), 7.95-8.00 (t, 1H), 7.73-7.79 (m, 2H), 7.22-7.42 (ds, 2H), 6.82-6.97 (m, 2H), 4.53-4.62 (q, 1H), 3.73-3.87 (q, 2H), 3.37-3.46 (m, 2H), 2.39-2.40 (ds, 6H), 1.95-2.02 (m, 1H). LC/MS: 440.0 [M+H]$^+$.

Example 41

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-ethyl)-2-oxo-pyrrolidin-3-yl]-amide

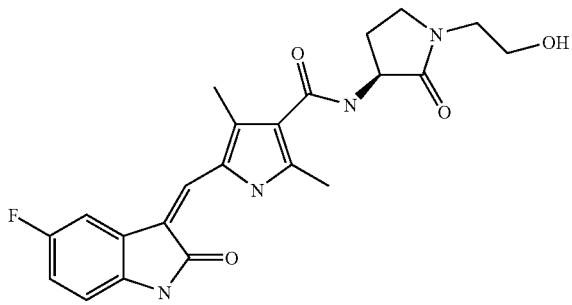

Preparation of (S)-3-Amino-1-(2-hydroxy-ethyl)-pyrrolidin-2-one

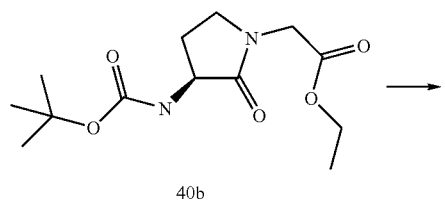

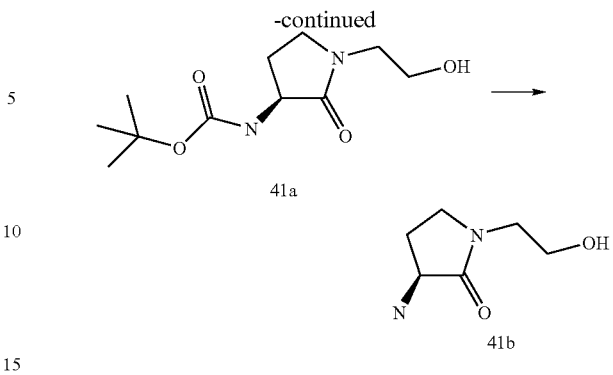

NaBH4 (85 mg, 2.24 mmol) was added to a solution of 40b (160 mg, 0.56 mmol) in tert-butyl alcohol (5 mL). The temperature was brought to 80° C., and MeOH (0.6 mL) was added slowly. The resulting mixture was kept under reflux for 2 h. After cooling under an ice bath, H2O (20 mL) was added and the alcohols were evaporated under vacuum. The aqueous phase was extracted with EA for several times. The organic layer was dried over anhydrous MgSO4 and concentrated. The residue was purified by Prep TLC to provide 41a (38 mg). To a solution of compound 41a (38 mg, 0.156 mmol) in 5 mL of DCM, was added TFA (0.18 mL, 2.34 mmol). The resulting mixture was stirred at r.t. for about 1 h and evaporated. The residue was added to a solution of A4 (36 mg, 0.086 mmol) and DIEA (0.08 mL, 0.43 mmol) in 20 mL of DMF. The reaction mixture was stirred at room temperature for several hours. LC/MS detection was applied to determine completion of the reaction. DMF was evaporated under reduced pressure and the residue was precipitated with 5% diethylamine/methanol (5 mL). The precipitate was collected by filtration, washed with ethanol and dried in vacuo to give an orange solid (29 mg, 79.2% yield): $^1$H NMR (300 MHz, DMSO-d6): δ=13.69 (s, 1H), 10.91 (s, 1H), 7.72-7.85 (m, 3H), 6.82-6.96 (m, 2H), 4.58-4.74 (m, 2H), 3.37-3.54 (m, 4H), 3.12-3.20 (m, 1H), 1.87-2.45 (m, 8H), 1.23-1.97 (m, 1H). LC/MS: 427.0 [M+H]$^+$.

Example 42

Preparation of 5-[5-Fluoro-2-oxo-1,2-dihydro-indol-(3Z)-ylidenemethyl]-2,4-dimethyl-1H-pyrrole-3-carboxylic acid [(R)-2-(2-hydroxy-ethyl)-3-oxo-isoxazolidin-4-yl]-amide

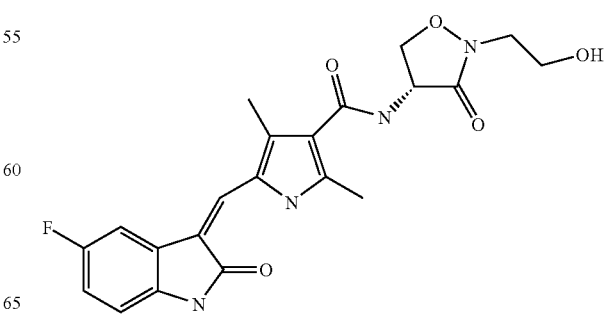

Preparation of 5-[5-Fluoro-2-oxo-1,2-dihydro-indol-(3Z)-ylidenemethyl]-2,4-dimethyl-1H-pyrrole-3-carboxylic acid ((R)-3-oxo-isoxazolidin-4-yl)-amide (42b)

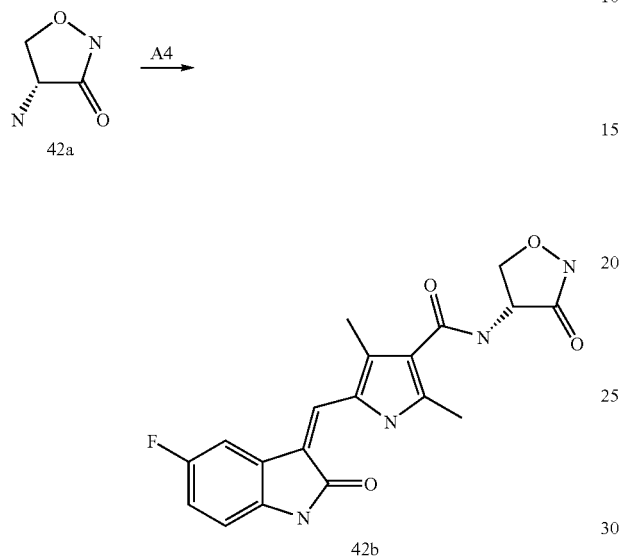

To the solution of A4 (1.75 g, 4.2 mmol) and DIEA (2.5 g, 17 mmol) in 150 mL of DMF, was added compound 42a (800 mg, 5.1 mmol). The reaction mixture was stirred at room temperature for several hours. LC/MS was applied to determine completion of the reaction. DMF was evaporated under reduced pressure and the residue was precipitated with 5% diethylamine/methanol (500 mL) under sonication. The solid was collected by filtration and washed with methanol, dried under vacuum to provide to provide 42b (1.41 g, 87.6% yield): $^1$H NMR (300 MHz, DMSO-d6): δ=13.68 (s, 1H), 10.88 (s, 1H), 7.71-7.77 (m, 3H), 7.41 (s, 1H), 6.82-6.96 (m, 2H), 4.08-4.13 (m, 1H), 3.06-3.13 (m, 1H), 2.41-2.45 (ds, 6H), 2.25-2.31 (m, 2H), 1.79-1.98 (m, 3H). LC/MS: 395.3 [M−H]$^+$.

To the solution of 42b (1.0 eq.) cooled on ice bath was added NaH (4.0 or 1.5 eq.). The resulting mixture was stirred for an hour and was then added 2-bromoethanol (3 eq.), the reaction mixture was stirred at room temperature for several hours. LC/MS detection was applied to determine completion of the reaction. DMF was evaporated under reduced pressure and the residue was precipitated with 5% diethylamine/methanol under sonication. The solid was collected by filtration, washed with methanol twice, and further purified by Prep-LC to obtain the title compound (18 mg, 11% yield) as orange solids: $^1$H NMR (300 MHz, DMSO-d6): δ=13.70 (s, 1H), 10.91 (s, 1H), 8.08-8.10 (d, 1H), 7.72-7.79 (m, 2H), 6.82-6.97 (m, 2H), 5.01-5.10 (q, 1H), 4.79-4.81 (t, 1H), 4.56-4.62 (t, 1H), 4.02-4.08 (q, 1H), 3.49-3.63 (m, 4H), 2.41-2.43 (ds, 6H). LC/MS: 428.9 [M+H]$^+$.

Example 43

Preparation of 5-[5-Fluoro-2-oxo-1,2-dihydro-indol-(3Z)-ylidenemethyl]-2,4-dimethyl-1H-pyrrole-3-carboxylic acid ((R)-2-dimethylcarbamoylmethyl-3-oxo-isoxazolidin-4-yl)-amide

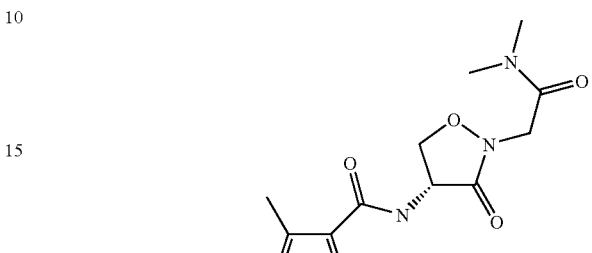

To the solution of 42b (1.0 eq.) cooled on ice bath was added NaH (4.0 or 1.5 eq.). The resulting mixture was stirred for an hour and was then added 2-bromo-N,N-dimethylacetamide (1.0 eq.), the reaction mixture was stirred at room temperature for several hours. LC/MS detection was applied to determine completion of the reaction. DMF was evaporated under reduced pressure and the residue was precipitated with 5% diethylamine/methanol under sonication. The solid was collected by filtration, washed with methanol twice, and further purified by column chromatography to obtain title compound (30 mg, 13.6% yield) as orange solids: $^1$H NMR (300 MHz, DMSO-d6): δ=13.73 (s, 1H), 10.93 (s, 1H), 8.05-8.08 (d, 1H), 7.74-7.80 (m, 2H), 6.82-6.97 (m, 2H), 5.06-5.15 (q, 1H), 4.39-4.58 (m, 3H), 4.05-4.11 (q, 1H), 2.97 (s, 3H), 2.84 (s, 3H), 2.44-2.47 (ds, 6H). LC/MS: 468.2 [M−H]$^+$.

Example 44

Preparation of 5-[5-Fluoro-2-oxo-1,2-dihydro-indol-(3Z)-ylidenemethyl]-2,4-dimethyl-1H-pyrrole-3-carboxylic acid ((R)-2-ethyl-3-oxo-isoxazolidin-4-yl)-amide

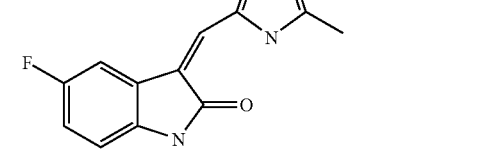

Preparation of (R)-4-Amino-2-ethyl-isoxazolidin-3-one

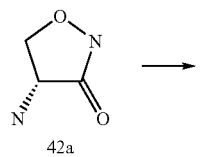

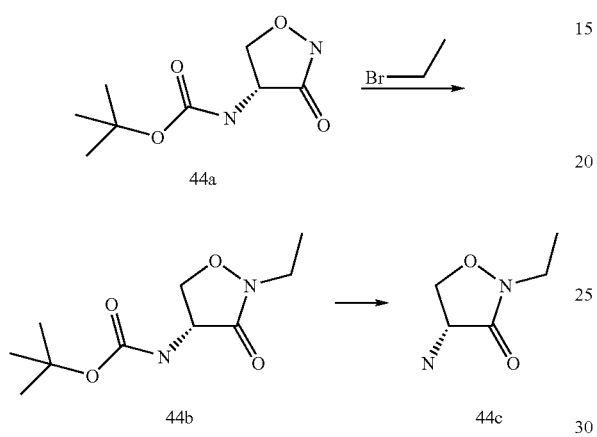

Step 1: Compound 42a (500 mg, 4.9 mmol) and TEA (976 mg, 9.64 mmol) were dissolved in a mixture of THF/water (85 mL, V/V 10:7). (Boc)2O (1.17 g, 5.4 mmol) was added dropwise under ice cooling. After the addition was complete, the mixture was warmed to r.t. and stirred for 5 h. The mixture was evaporated to dryness and the residue was purified by column chromatography (EA:PE=3:1) to provide compound 44a (600 mg, 61%) as white solid.

Step 2: To the solution of compound 44a (100 mg, 0.5 mmol), was added 60% NaH (24 mg, 0.6 mmol) under ice cooling. The resulting mixture was stirred for 1 h and was added bromoethane (60 mg, 0.55 mmol). The mixture was warmed to r.t. and stirred overnight and evaporated to dryness. The residue was purified by column chromatography (EA:PE=10:1) to provide compound 44b (109 mg, 94.7%).

Step 3: To a solution of compound 44b (109 mg, 0.47 mmol) in 5 mL of DCM, was added TFA (810 mg, 7.1 mmol). The resulting mixture was stirred at r.t. for about 1 h and evaporated which was then added to the solution of A4 (160 mg, 0.38 mmol) and DIEA (196 mg, 1.52 mmol) in 18 mL of DMF. The reaction mixture was stirred at room temperature for several hours. LC/MS detection was applied to determine completion of the reaction. DMF was evaporated under reduced pressure and the residue was precipitated with 5% diethylamine/methanol (10 mL) under sonication. The solid was collected by filtration and washed with methanol, dried under vacuum to provide title compound (123 mg, 77.8% yield). $^1$H NMR (300 MHz, DMSO-d6): δ=13.71 (s, 1H), 10.39 (s, 1H), 8.07-8.10 (d, 1H), 7.72-7.78 (m, 2H), 6.82-6.96 (m, 2H), 4.97-5.06 (q, 1H), 4.57-4.62 (t, 1H), 4.02-4.08 (q, 1H), 3.50-3.58 (m, 2H), 2.43-2.45 (ds, 6H), 1.13-1.18 (t, 3H). LC/MS: 412.9 [M+H]$^+$.

Example 45

Preparation of 5-[5-Fluoro-2-oxo-1,2-dihydro-indol-(3Z)-ylidenemethyl]-2,4-dimethyl-1H-pyrrole-3-carboxylic acid ((R)-2-carbamoylmethyl-3-oxo-isoxazolidin-4-yl)-amide

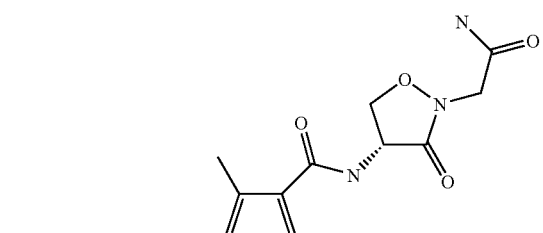

The synthesis of the title compound is similar to that of Example 44 (71% yield): $^1$H NMR (300 MHz, DMSO-d6): δ=13.73 (s, 1H), 10.91 (s, 1H), 8.09-8.11 (d, 1H), 7.73-7.79 (m, 2H), 7.33-7.53 (ds, 2H), 6.82-6.97 (m, 2H), 5.02-5.07 (q, 1H), 4.55-4.60 (t, 1H), 4.01-4.17 (m, 3H), 2.44-2.46 (ds, 6H). LC/MS: 441.9 [M+H]$^+$.

Example 46

Preparation of 5-[5-Fluoro-2-oxo-1,2-dihydro-indol-(3Z)-ylidenemethyl]-2,4-dimethyl-1H-pyrrole-3-carboxylic acid [(R)-2-(2-methoxy-ethyl)-3-oxo-isoxazolidin-4-yl]-amide

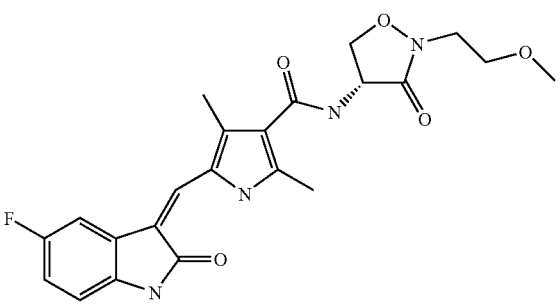

The synthesis of the title compound is similar to that of Example 44 (89.3% yield): $^1$H NMR (300 MHz, DMSO-d6): δ=13.75 (s, 1H), 10.91 (s, 1H), 8.09-8.12 (d, 1H), 7.72-7.79 (m, 2H), 6.82-6.97 (m, 2H), 4.99-5.08 (q, 1H), 4.57-4.63 (t, 1H), 4.01-4.07 (q, 1H), 3.37-3.74 (m, 4H), 3.22 (s, 3H), 2.35-2.37 (ds, 6H). LC/MS: 443.0 [M+H]$^+$.

Example 47

Preparation of 5-[5-Fluoro-2-oxo-1,2-dihydro-indol-(3Z)-ylidenemethyl]-2,4-dimethyl-1H-pyrrole-3-carboxylic acid ((R)-3-oxo-2-pyridin-3-ylmethyl-isoxazolidin-4-yl)-amide

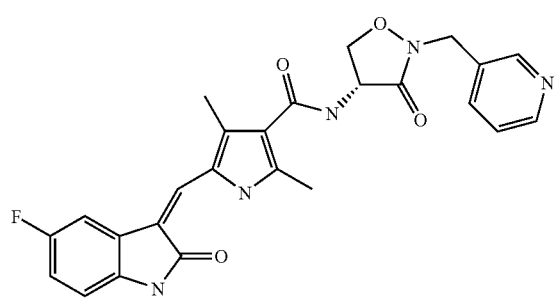

The synthesis of the title compound is similar to that of Example 44 (73.8% yield): $^1$H NMR (300 MHz, DMSO-d6): δ=13.73 (s, 1H), 10.91 (s, 1H), 8.52-8.57 (m, 2H), 8.17-8.19 (d, 1H), 7.73-7.79 (m, 3H), 7.39-7.43 (m, 1H), 6.82-6.97 (m, 2H), 5.05-5.14 (q, 1H), 4.63-4.85 (q, 2H), 4.57-4.63 (t, 1H), 4.06-4.13 (q, 1H), 2.43-2.46 (ds, 6H). LC/MS: 476.1 [M+H]$^+$.

Example 48

Preparation of 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-yl)-isoxazolidin-4-yl]-amide

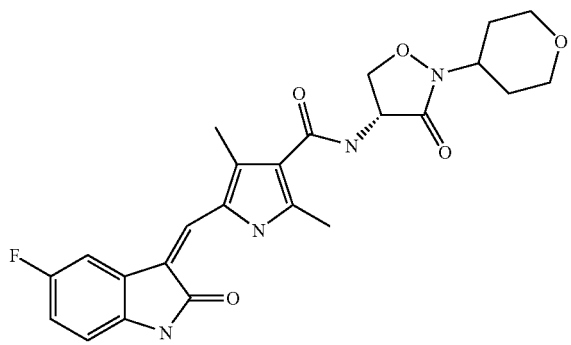

Preparation of (R)-4-Amino-2-(tetrahydro-pyran-4-yl)-isoxazolidin-3-one (48c)

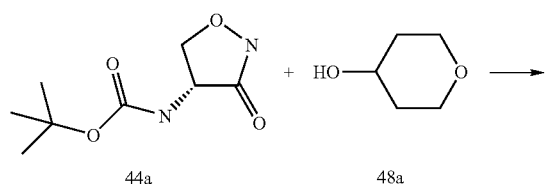

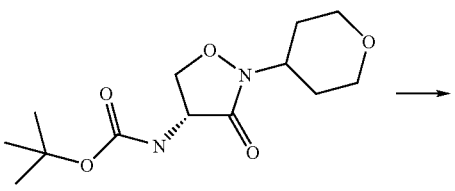

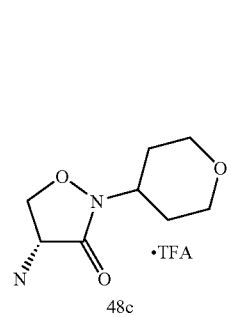

Step 1: To a solution of 44a (150 mg, 0.74 mmol), 48a (83 mg, 0.82 mmol) and PPh3 (290 mg, 1.1 mmol) in THF (20 mL) was added DEAD (206 mg, 1.2 mmol) in THF (2 mL) dropwise at −60° C. After the addition was complete, the reaction mixture was warmed to room temperature gradually and stirred for 2 days. The mixture was then evaporated and the residue was purified by column chromatography (EA: PE=4:1) to provide a clear oil which still contained small amount of 44a. The obtained oil was purified again by Prep-TLC to provide a mixture of 48b and POPh3 (131 mg).

Step 2: To a solution of the obtained mixture of 48b and POPh3 (131 mg) in DCM (4 mL) was added TFA (1 mL) at room temperature. The mixture was stirred for 3 h and evaporated to provide crude 48c which was used for the next step directly.

Step 3: To a solution of A4 (84 mg, 2 mmol) in 10 mL of DMF, were added the crude 48c from last step and DIEA (2 mL), the reaction mixture was stirred at room temperature overnight. LC/MS was applied to determine completion of the reaction. The reaction mixture was evaporated under reduced pressure and the residue was triturated with 5% diethylamine/methanol (25 mL). The solid was collected by filtration and washed with methanol, dried under vacuum to provide the title compound (58 mg, 62%) as orange solid. $^1$H NMR (300 MHz, DMSO-d6): δ=13.73 (s, 1H), 10.94 (s, 1H), 8.12-8.15 (d, 1H), 7.73-7.80 (m, 2H), 6.82-6.87 (m, 2H), 5.02-5.05 (q, 1H), 4.58-4.64 (t, 1H), 3.86-4.14 (m, 4H), 3.38-3.44 (m, 2H), 2.42-2.50 (ds, 6H), 1.65-1.88 (m, 4H). LC/MS: 469.0 [M+H]$^+$.

Example 49

Preparation of 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-3-yl)-isoxazolidin-4-yl]-amide

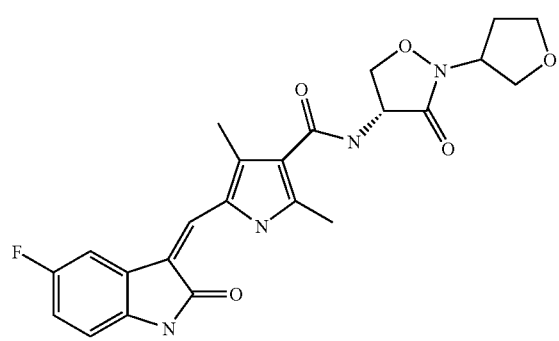

Preparation of (R)-4-Amino-2-(tetrahydro-furan-3-yl)-isoxazolidin-3-one (49c)

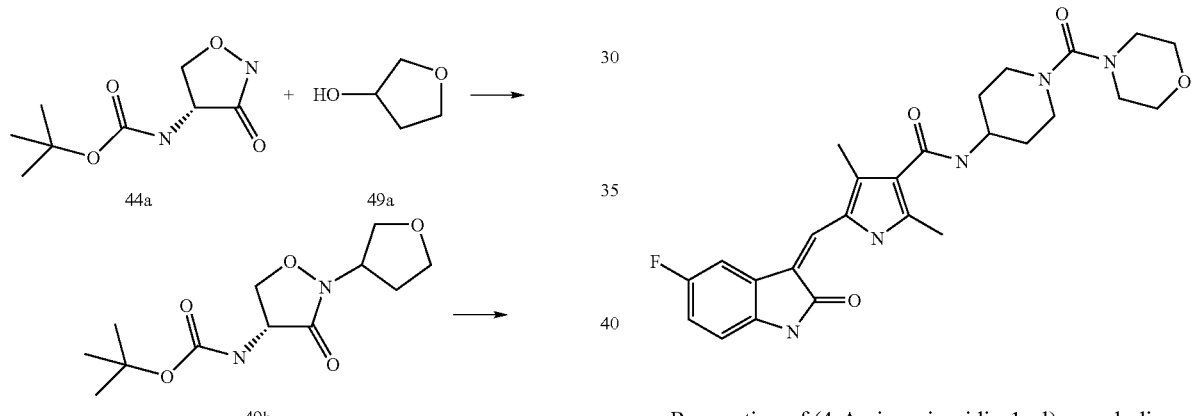

-continued

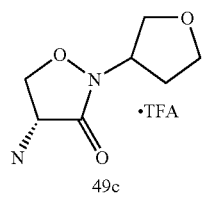

The synthesis was similar to that of Example 48 except that compound 49a was used. The title compound (59 mg, 65%) was obtained as orange solid. $^1$H NMR (300 MHz, DMSO-d6): δ=13.72 (s, 1H), 10.94 (s, 1H), 8.12-8.15 (d, 1H), 7.73-7.80 (m, 2H), 6.82-6.97 (m, 2H), 4.99-5.05 (q, 1H), 4.58-4.78 (m, 2H), 4.03-4.10 (m, 1H), 3.69-3.88 (m, 4H), 2.13-2.40 (ds, 6H), 2.03-2.13 (m, 4H). LC/MS: 454.9 [M+H]$^+$.

Example 50

Preparation of 5-[5-Fluoro-2-oxo-1,2-dihydro-indol-(3Z)-ylidenemethyl]-2,4-dimethyl-1H-pyrrole-3-carboxylic acid [1-(morpholine-4-carbonyl)-piperidin-4-yl]-amide Preparation of (4-Amino-piperidin-1-yl)-morpholin-4-yl-methanone (50d)

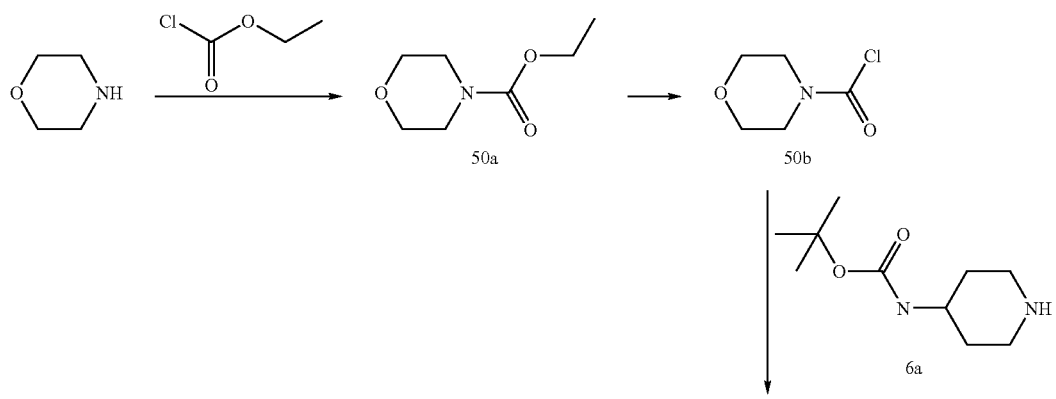

-continued

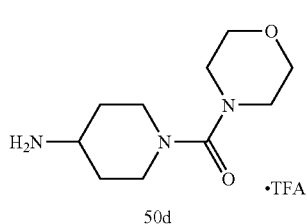

50d

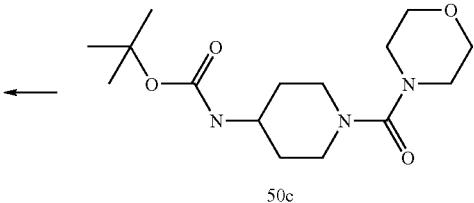

50c

Step 1: To a solution of morpholine (20 g, 0.23 mol), pyridine (31 mL, 0.38 mol) in DCM (100 mL), was added ethyl chlorooate (27.4 g, 0.253 mol) drop-wise at 0° C. The obtained mixture was stirred at room temperature overnight and washed with saturated aqueous NaHCO3 and brine. The organic phase was dried over anhydrous Na2SO4 and evaporated to provide crude 50a (36 g, 96%) as yellow solid.

Step 2: A mixture of 50a (20 g, 0.126 mol) and POCl3 (97 g, 0.63 mol) in dry ACN (200 mL) was refluxed for 18 h with stirring. After being cooled, the reaction mixture was diluted by DCM (80 mL) and poured into crushed ice. The organic layer was separated and the aqueous layer was extracted by DCM (200 mL*3). The combined DCM phase was washed with saturated aqueous NaHCO3 and brine, dried over anhydrous Na2SO4 and evaporated. The residue was purified by distillation. Compound 50b was obtained by collecting the distillate of 82-84° C. (1 mmHg) (13 g, 69%).

Step 3: To a solution of 6a (20 g, 0.23 mol), TEA (31 mL, 0.38 mol) in DCM (100 mL), was added 50b (277.4 g, 0.253 mol) in DCM drop-wise at 0° C. The obtained mixture was stirred at room temperature overnight and washed with saturated aqueous NaHCO3 and brine. The organic phase was dried over anhydrous Na2SO4 and evaporated to provide crude 50c (77 mg, 95%) as yellow solid.

The de-Boc step and final coupling to A4 were similar to that of example 48 to obtain the title compound (45 mg, 60%) as orange solid. $^1$H NMR (300 MHz, DMSO-d6): δ=13.68 (s, 1H), 10.90 (s, 1H), 7.59-7.78 (m, 3H), 6.81-6.93 (m, 2H), 3.91-3.94 (m, 1H), 3.56-3.60 (m, 6H), 3.11-3.13 (m, 4H), 2.83-2.91 (t, 2H), 2.39-2.41 (ds, 6H), 1.79-1.1.83 (m, 2H), 1.44-1.51 (m, 2H). LC/MS: 496.0 [M+H]$^+$.

Example 51

Preparation of 5-[5-Fluoro-2-oxo-1,2-dihydro-indol-(3Z)-ylidenemethyl]-2,4-dimethyl-1H-pyrrole-3-carboxylic acid [(S)-1-(morpholine-4-carbonyl)-pyrrolidin-3-yl]-amide Preparation of ((R)-3-Amino-pyrrolidin-1-yl)-morpholin-4-yl-methanone (51c)

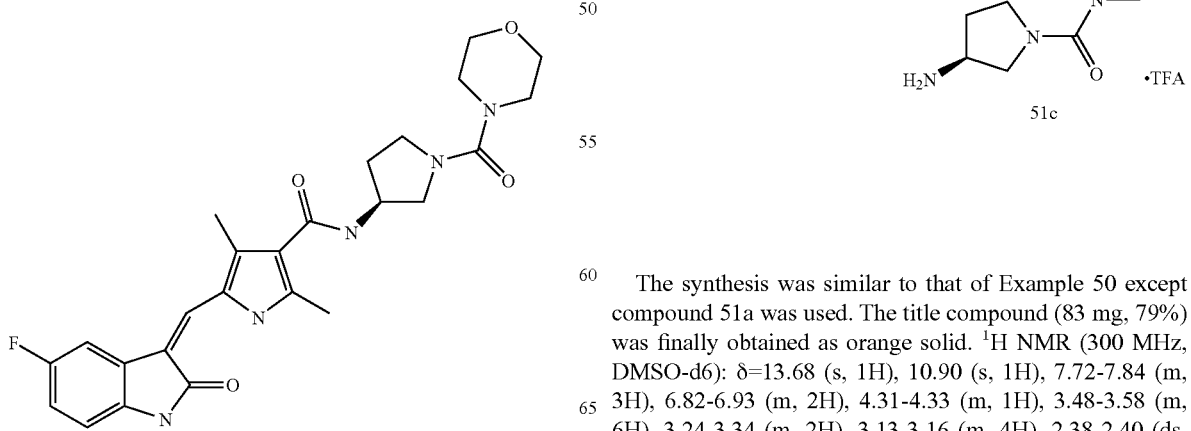

The synthesis was similar to that of Example 50 except compound 51a was used. The title compound (83 mg, 79%) was finally obtained as orange solid. $^1$H NMR (300 MHz, DMSO-d6): δ=13.68 (s, 1H), 10.90 (s, 1H), 7.72-7.84 (m, 3H), 6.82-6.93 (m, 2H), 4.31-4.33 (m, 1H), 3.48-3.58 (m, 6H), 3.24-3.34 (m, 2H), 3.13-3.16 (m, 4H), 2.38-2.40 (ds, 6H), 1.87-2.03 (m, 2H). LC/MS: 480.3 [M−H]$^+$.

Example 52

Preparation of 4-({5-[5-Fluoro-2-oxo-1,2-dihydro-indol-(3Z)-ylidenemethyl]-2,4-dimethyl-1H-pyrrole-3-carbonyl}-amino)-piperidine-1-carboxylic acid dimethylamide

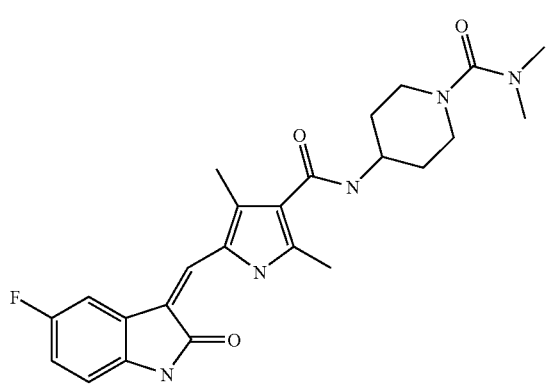

The title compound (35 mg, 56%) was obtained as orange solid following the procedure for Example 50. ¹H NMR (300 MHz, DMSO-d6): δ=13.68 (s, 1H), 10.91 (s, 1H), 7.60-7.79 (m, 3H), 6.81-6.96 (m, 2H), 3.90-3.92 (m, 1H), 3.50-3.54 (d, 2H), 2.77-2.84 (t, 2H), 3.13-3.16 (m, 4H), 2.73 (s, 6H), 2.39-2.41 (ds, 6H), 1.78-1.82 (m, 2H), 1.45-1.52 (m, 2H). LC/MS: 452.3 [M−H]⁺.

Example 53

Preparation of 5-[5-Fluoro-2-oxo-1,2-dihydro-indol-(3Z)-ylidenemethyl]-2,4-dimethyl-1H-pyrrole-3-carboxylic acid ((S)-1-dimethylcarbamoyl-pyrrolidin-3-yl)-amide

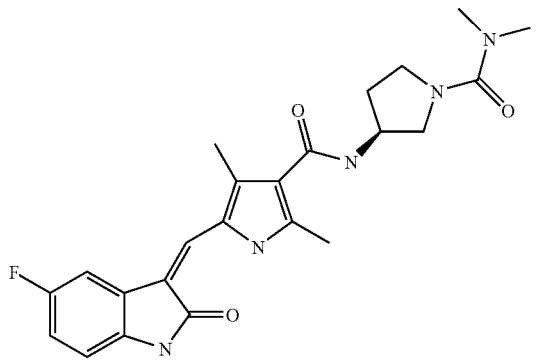

The title compound (20 mg, 55%) was obtained as orange solid following the procedure for Example 51. ¹H NMR (300 MHz, DMSO-d6): δ=13.68 (s, 1H), 10.91 (s, 1H), 7.72-7.83 (m, 3H), 6.82-6.96 (m, 2H), 4.28-4.36 (m, 1H), 3.21-3.53 (m, 4H), 2.73 (s, 6H), 2.38-2.40 (ds, 6H), 1.85-2.04 (m, 2H). LC/MS: 438.3 [M−H]⁺.

Example 54

Preparation of 5-[5-Fluoro-2-oxo-1,2-dihydro-indol-(3Z)-ylidenemethyl]-2,4-dimethyl-1H-pyrrole-3-carboxylic acid [1-(2-methoxy-acetyl)-piperidin-4-yl]-amide

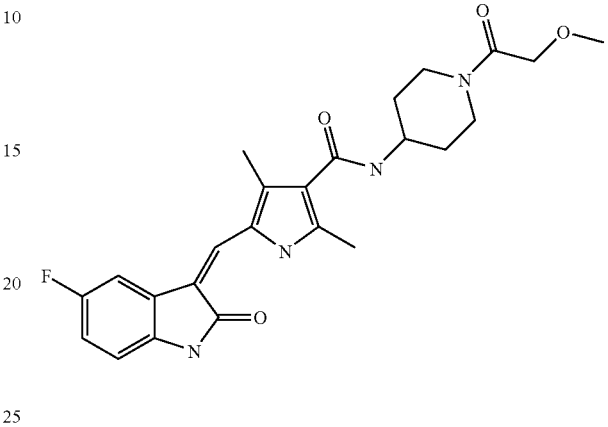

Preparation of 1-(4-Amino-piperidin-1-yl)-2-methoxy-ethanone (54d)

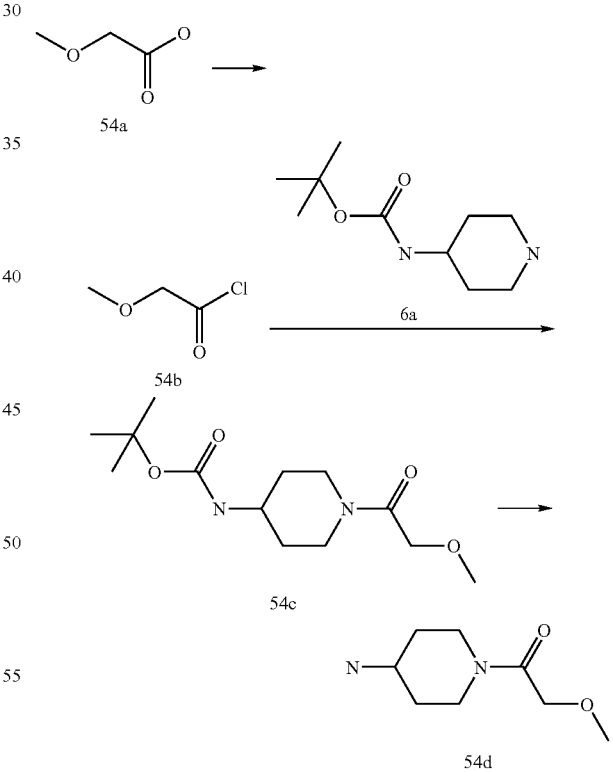

Step 1: To a solution of compound 54a (20 mL, 0.26 mol) in DCM (170 mL) at 0° C., was added oxalyl chloride (30 mL, 0.34 mol) drop-wise and a few drops of DMF. The mixture was stirred at room temperature overnight and evaporated. The residue was distilled to provide 54b (25.4 g, 90%).

Step 2: To a solution of 6a (100 mg, 0.5 mmol) and TEA (0.16 mL, 2 mmol) in DCM (10 mL) was added 54b (60 mg, 0.55 mmol) in DCM (2 mL) drop-wise at 0° C. The obtained mixture was stirred at room temperature overnight and washed with saturated aqueous NaHCO3 and brine. The organic phase was dried over anhydrous Na2SO4 and evaporated to provide crude 54c (129 mg, 95%) as yellow solid.

The de-Boc step and final coupling to A4 were similar to that of Example 48. The title compound (65 mg, 41%) was obtained as orange solid. ¹H NMR (300 MHz, DMSO-d6): δ=13.65 (s, 1H), 10.87 (s, 1H), 7.59-7.76 (m, 3H), 6.80-7.94 (m, 2H), 3.96-4.23 (m, 4H), 3.70-3.76 (m, 2H), 3.26 (s, 3H), 3.08-3.16 (m, 1H), 2.71-2.87 (m, 1H), 2.37-2.40 (ds, 6H), 1.83-1.85 (m, 2H), 1.33-1.45 (m, 2H). LC/MS: 454.9 [M+H]⁺.

Example 55

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-methoxy-acetyl)-pyrrolidin-3-yl]-amide

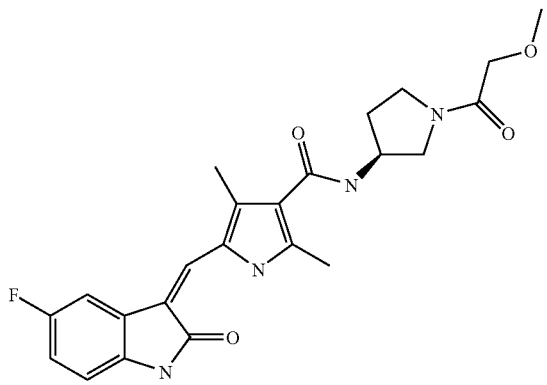

The title compound (51 mg, 31%) was obtained as orange solid following the procedure for Example 54. ¹H NMR (300 MHz, DMSO-d6): δ=13.67 (s, 1H), 10.88 (s, 1H), 7.70-7.89 (m, 3H), 6.80-6.94 (m, 2H), 4.35-4.43 (m, 1H), 3.97-3.99 (d, 2H), 3.33-3.67 (m, 4H), 3.23 (s, 3H), 2.37-2.39 (ds, 6H), 1.85-2.15 (m, 2H). LC/MS: 440.9 [M+H]⁺.

Example 56

Preparation of N-((3R)oxolan-3-yl){5-[(5-fluoro-2-oxo(1H-benzo[d]azolin-3-ylidene))methyl]-2,4-dimethylpyrrol-3-yl}carboxamide

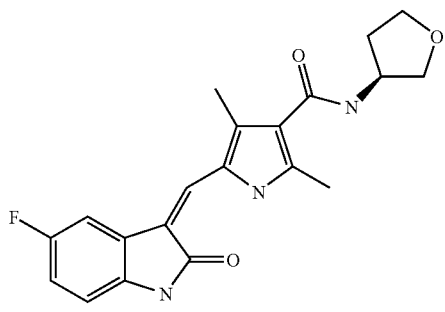

The synthesis was similar to the final step of Example 48 using (S)-(Tetrahydro-furan-3-yl)amine as starting material. The title compound (82 mg, 93%) was obtained as orange solid. ¹H NMR (300 MHz, DMSO-d6): δ=13.68 (s, 1H), 10.91 (s, 1H), 7.72-7.88 (m, 3H), 6.83-6.93 (m, 2H), 4.21-4.25 (m, 1H), 3.53-3.87 (m, 4H), 2.39-2.41 (ds, 6H), 2.39-2.41 (m, 1H), 2.09-2.12 (m, 1H). LC/MS: 370.1 [M+H]⁺.

Example 57

Preparation of 5-[5-Fluoro-2-oxo-1,2-dihydro-indol-(3Z)-ylidenemethyl]-2,4-dimethyl-1H-pyrrole-3-carboxylic acid [(R)-2-(2-morpholin-4-yl-ethyl)-3-oxo-isoxazolidin-4-yl]-amide

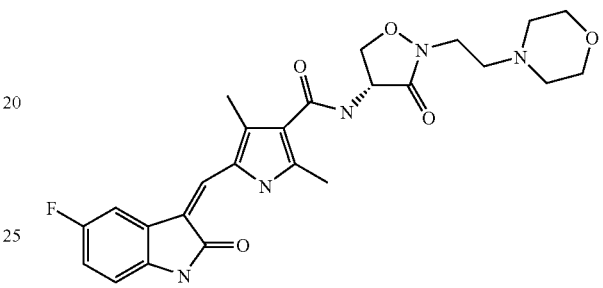

To a solution of 42b (200 mg, 0.52 mmol), NaI (78 mg, 0.52 mmol) and DIEA (134 mg, 1.04 mmol) in DMF (25 mL) was added 60% NaH (125 mg, 3.13 mmol) at 0° C. After stirring at room temperature for 1 h, the mixture was added 4-(2-Chloro-ethyl)-morpholine chloride (194 mg, 1.05 mmol). The obtained mixture was stirred 48 h at room temperature. LC-MS was used to detect completion of the reaction. The mixture was evaporated under reduced pressure and the residue was triturated with 5% diethylamine/methanol (25 mL). The solid was collected by filtration which was purified again by column chromatography (CH2Cl2:MeOH=20:1) to provide the title compound (60 mg, 23%) as orange solid. ¹H NMR (300 MHz, DMSO-d6): δ=13.59 (s, 1H), 11.53 (s, 1H), 7.79-8.13 (m, 3H), 7.04-7.12 (m, 2H), 5.00-5.06 (q, 1H), 4.57-4.62 (t, 1H), 3.97-4.10 (m, 3H), 3.44-3.58 (m, 4H), 2.78-2.94 (m, 1H), 2.47-2.50 (ds, 6H). LC/MS: 498.2 [M+H]⁺.

Example 58

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-2-oxo-pyrrolidin-3-yl]-amide

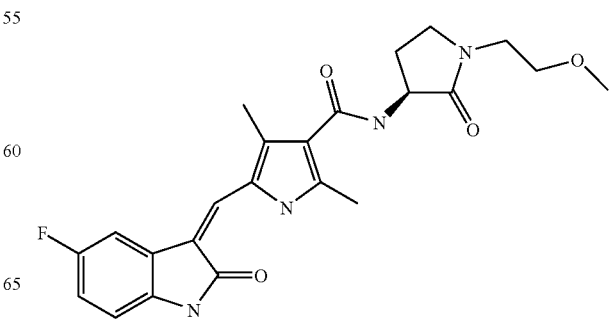

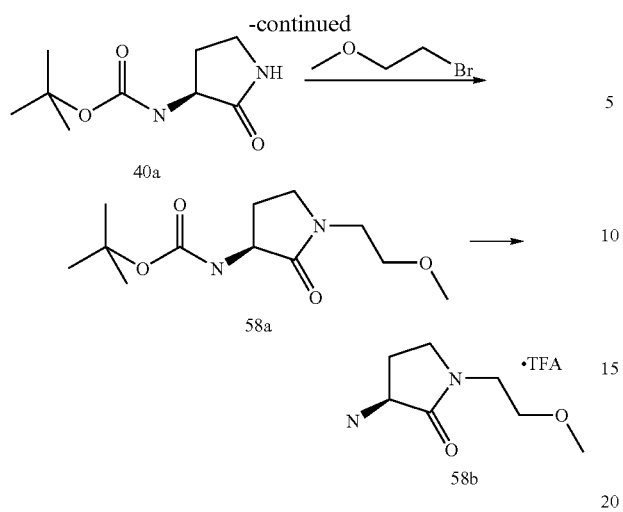

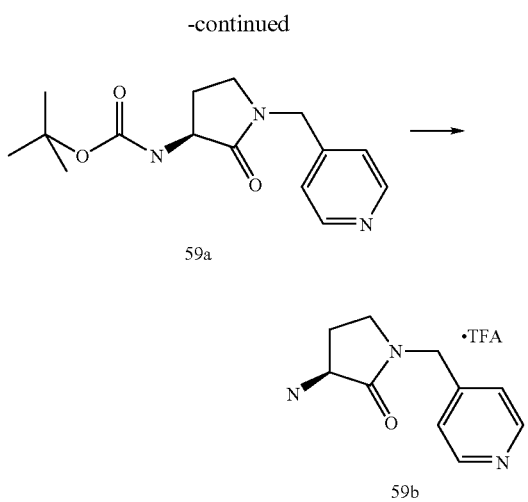

Step 1: To a solution of 40a (100 mg, 0.5 mmol) in DMF (5 mL) was added 60% NaH (21 mg, 0.53 mmol) at 0° C. After stirring at room temperature for 1 h, the mixture was added compound 1-Bromo-2-methoxy-ethane (67.5 mg, 0.49 mmol). The obtained mixture was stirred overnight at room temperature, evaporated. The residue was purified by column chromatography (EA:PE=1:1) to provide 58a (68 mg, 54%).

Step 2: The de-Boc step and final coupling to A4 were similar to that of Example 48. The title compound (54 mg, 77%) was obtained as orange solid. $^1$H NMR (300 MHz, DMSO-d6): δ=13.68 (s, 1H), 10.91 (s, 1H), 7.72-7.87 (m, 3H), 6.82-6.93 (m, 2H), 4.59-4.62 (q, 2H), 3.38-3.49 (m, 6H), 3.30 (s, 3H), 2.42-2.45 (ds, 6H), 2.15-2.20 (m, 1H), 1.90-2.00 (m, 1H). LC/MS: 439.3 [M−H]$^+$.

Example 59

Preparation of 5-[5-Fluoro-2-oxo-1,2-dihydro-indol-(3Z)-ylidenemethyl]-2,4-dimethyl-1H-pyrrole-3-carboxylic acid ((S)-2-oxo-1-pyridin-4-ylmethyl-pyrrolidin-3-yl)-amide The synthesis was similar to that of Example 58. The title compound (24 mg, 66%) was obtained as orange solid. $^1$H NMR (300 MHz, DMSO-d6): δ=13.71 (s, 1H), 10.93 (s, 1H), 8.53-8.55 (m, 1H), 8.00-8.02 (d, 1H), 7.73-7.80 (m, 2H), 7.30-7.32 (d, 2H), 6.82-6.95 (m, 2H), 4.40-4.69 (m, 3H), 3.28-3.34 (m, 2H), 2.44-2.47 (ds, 6H). LC/MS: 472.2 [M−H]$^+$.

Example 60

Preparation of 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-ylmethyl)-isoxazolidin-4-yl]-amide

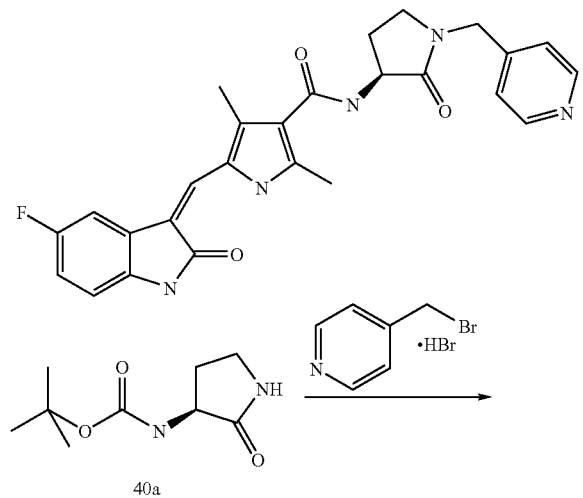

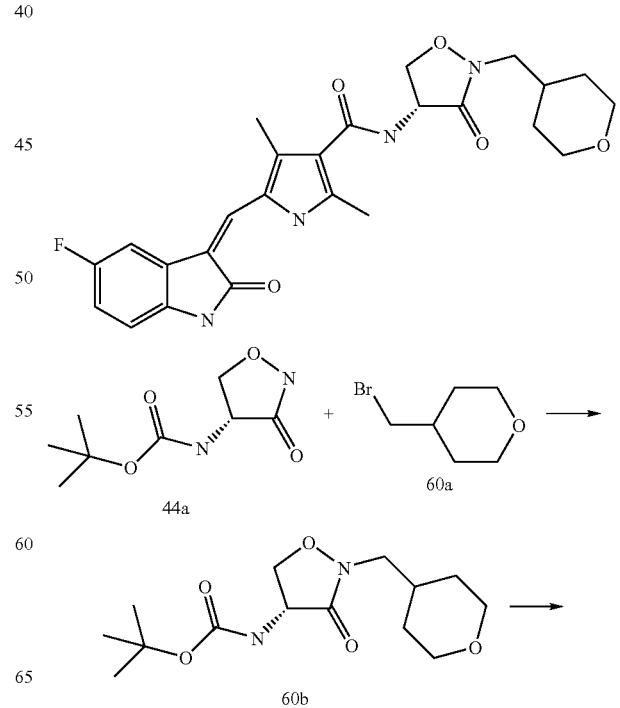

-continued

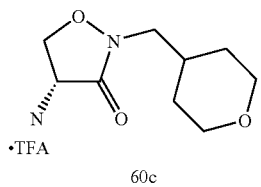

60c

The synthesis was similar to that of Example 58. The title compound (51 mg, 79%) was obtained as orange solid. $^1$H NMR (300 MHz, DMSO-d6): δ=13.72 (s, 1H), 10.94 (s, 1H), 8.14-8.16 (d, 1H), 7.73-7.80 (m, 2H), 6.82-6.94 (m, 2H), 5.06-5.10 (q, 1H), 4.57-4.63 (t, 1H), 4.03-4.12 (m, 2H), 3.82-3.87 (m, 2H), 3.40-3.42 (m, 1H), 3.15-3.42 (m, 4H), 2.42-2.45 (ds, 6H), 1.80-1.95 (m, 1H), 1.53-1.64 (m, 2H), 1.18-1.26 (m, 2H). LC/MS: 481.2 [M–H]$^+$.

Example 61

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-pyrrolidin-3-yl]-amide mmol) and K2CO3 (370 mg, 2.69 mmol) in 15 mL of acetonitrile were stirred under reflux for 48 h. After being cooled, the mixture was filtered and the filtrate was evaporated to dryness. The residue was purified by column chromatography (EA:MeOH=10:1) to give 61a (102 mg, 78%) as yellow oil.

Step 2: The de-Boc step and final coupling to A4 were similar to that of Example 48. The title compound (73 mg, 84%) was obtained as orange solid. $^1$H NMR (300 MHz, DMSO-d6): δ=13.65 (s, 1H), 10.91 (s, 1H), 7.71-7.79 (m, 3H), 6.82-6.96 (m, 2H), 4.31-4.33 (m, 1H), 3.40-3.44 (t, 2H), 3.24 (s, 3H), 2.82-2.88 (m, 1H), 2.53-2.60 (m, 5H), 3.39-3.41 (ds, 6H), 2.09-2.12 (m, 1H), 1.67-1.71 (m, 1H). LC/MS: 427.1 [M+H]$^+$.

Example 62

Preparation of 5-[5-Fluoro-2-oxo-1,2-dihydro-indol-(3Z)-ylidenemethyl]-2,4-dimethyl-1H-pyrrole-3-carboxylic acid [1-(2-methoxy-ethyl)-piperidin-4-yl]-amide

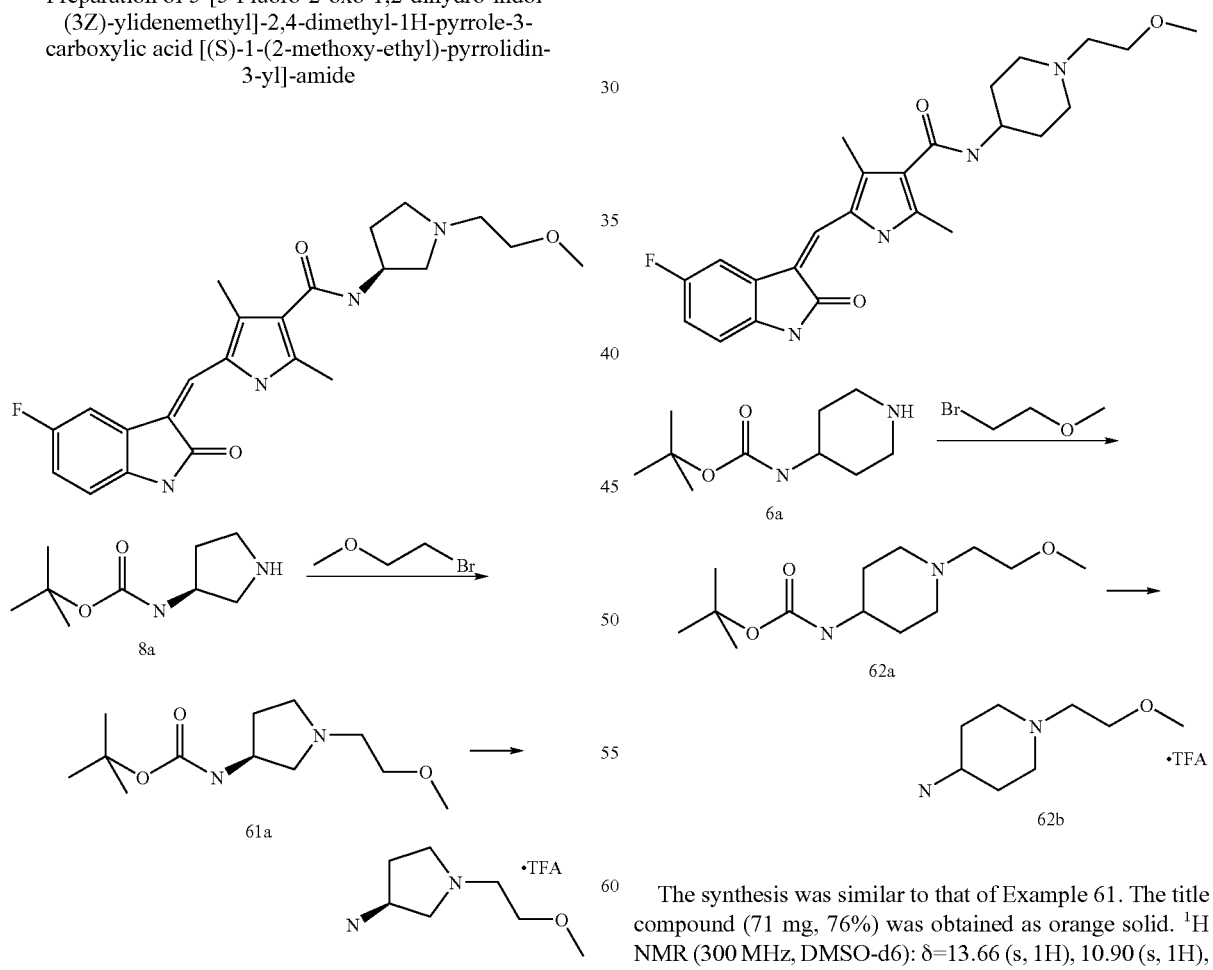

Step 1: A solution of 8a (100 mg, 0.54 mmol), 1-bromo-2-methoxy-ethane (89.5 mg, 0.64 mmol), KI (94 mg, 0.56

The synthesis was similar to that of Example 61. The title compound (71 mg, 76%) was obtained as orange solid. $^1$H NMR (300 MHz, DMSO-d6): δ=13.66 (s, 1H), 10.90 (s, 1H), 7.54-7.78 (m, 3H), 6.81-6.96 (m, 2H), 3.68-3.72 (m, 1H), 3.40-3.44 (t, 2H), 3.23 (s, 3H), 2.83-2.92 (m, 2H), 2.45-2.50 (m, 2H), 2.39-2.41 (ds, 6H), 2.04-2.11 (t, 2H), 1.76-1.79 (m, 2H), 1.46-1.57 (m, 2H). LC/MS: 441.1 [M+H]$^+$.

Example 63

Preparation of 5-[5-Fluoro-2-oxo-1,2-dihydro-indol-(3Z)-ylidenemethyl]-2,4-dimethyl-1H-pyrrole-3-carboxylic acid [1-(2-dimethylamino-acetyl)-piperidin-4-yl]-amide

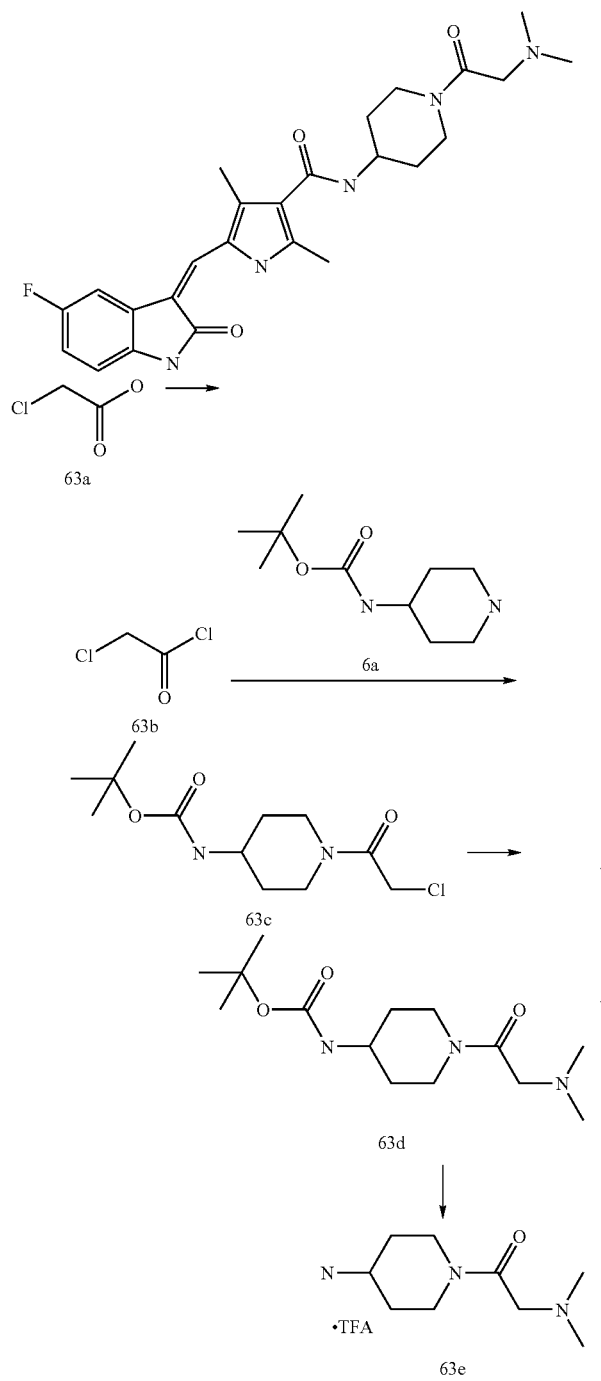

Step 1: Compound 63c (125 mg, 60%) was synthesized following procedure in making 54c in Example 54.

Step 2: To a solution of 63c (125 mg, 0.45 mmol) in 15 mL of acetonitrile were added NH(CH3)2.HCl (110 mg, 1.36 mmol) and DIEA (232 mg, 1.8 mmol) at room temperature. The obtained mixture was stirred overnight and evaporated. The residue was re-dissolved in DCM and washed with brine. The DCM phase was separated, dried over anhydrous Na2SO4 and evaporated to provide crude 63d which was directly used for the next step synthesis (118 mg, 92%).

Step 3: The de-Boc step and final coupling to A4 were similar to that of Example 48. The title compound (49 mg, 51%) was obtained as orange solid. $^1$H NMR (300 MHz, DMSO-d6): δ=13.66 (s, 1H), 10.89 (s, 1H), 7.61-7.77 (m, 3H), 6.80-6.91 (m, 2H), 4.21-4.25 (d, 1H), 3.95-3.99 (d, 2H), 3.07-3.18 (m, 4H), 2.70-2.79 (m, 2H), 2.38-2.40 (ds, 6H), 2.15 (s, 6H), 1.79-1.83 (m, 2H). LC/MS: 466.3 [M–H]$^+$.

Example 64

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-dimethylamino-acetyl)-pyrrolidin-3-yl]-amide

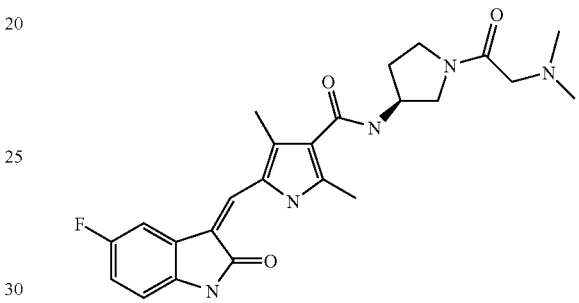

The title compound (44 mg, 47%) was synthesized as orange solid following the procedure of Example 63. $^1$H NMR (300 MHz, DMSO-d6): δ=13.72 (s, 1H), 10.91 (s, 1H), 7.71-7.89 (m, 3H), 6.81-6.95 (m, 2H), 4.35-4.44 (m, 1H), 3.57-3.78 (m, 4H), 2.99-3.01 (d, 2H), 2.38-2.40 (ds, 6H), 2.08-2.13 (ds, 6H), 1.85-2.04 (m, 2H). LC/MS: 452.3 [M–H]$^+$.

Example 65

Preparation of 5-[5-Fluoro-2-oxo-1,2-dihydro-indol-(3Z)-ylidenemethyl]-2,4-dimethyl-1H-pyrrole-3-carboxylic acid [1-(2-hydroxy-ethyl)-piperidin-4-yl]-amide

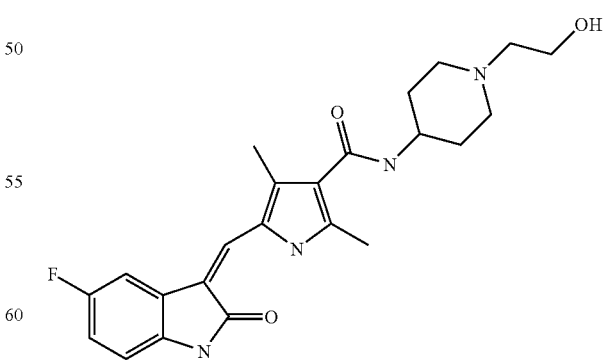

The title compound (31 mg, 39%) was synthesized as orange solid following the procedure of Example 62. $^1$H NMR (300 MHz, DMSO-d6): δ=13.66 (s, 1H), 10.90 (s, 1H), 7.56-7.78 (m, 3H), 6.81-6.95 (m, 2H), 4.40-4.46 (m, 1H), 3.69-3.73 (m, 1H), 3.45-3.50 (m, 2H), 2.72-2.84 (d, 2H), 2.38-2.40 (m, 8H), 1:90-2.20 (m, 2H), 1.76-1.80 (m, 2H), 1.24-1.44 (m, 2H). LC/MS: 427.2 [M+H]+.

Example 66

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-ethyl)-pyrrolidin-3-yl]-amide

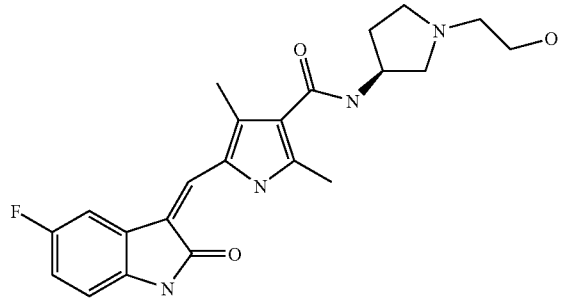

The title compound (29 mg, 35%) was synthesized as orange solid following the procedure of Example 61. ¹H NMR (300 MHz, DMSO-d6): δ=13.66 (s, 1H), 10.87 (s, 1H), 7.70-7.77 (m, 3H), 6.81-6.95 (m, 2H), 4.32-4.40 (m, 2H), 3.44-3.50 (q, 2H), 2.77-2.83 (t, 1H), 2.52-2.66 (m, 2H), 2.39-2.46 (m, 8H), 2.07-2.13 (m, 1H), 1.62-1.69 (m, 2H), 0.88-0.97-1.44 (m, 1H). LC/MS: 413.2 [M+H]+.

Example 67

Preparation of 5-[5-Fluoro-2-oxo-1,2-dihydro-indol-(3Z)-ylidenemethyl]-2,4-dimethyl-1H-pyrrole-3-carboxylic acid (6'-methyl-3,4,5,6-tetrahydro-2H-[1,3']bipyridinyl-4-yl)-amide

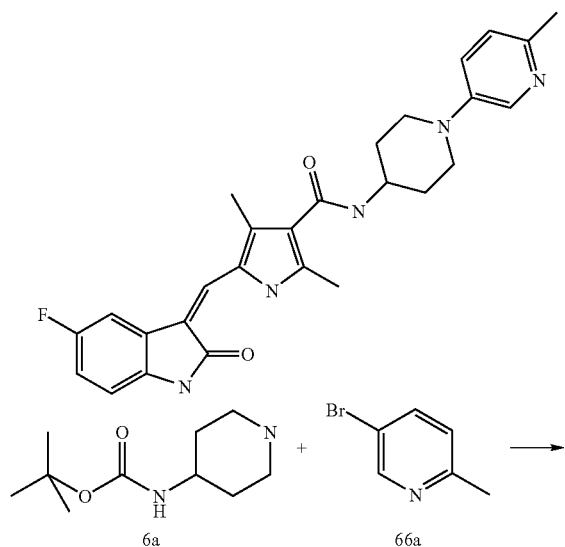

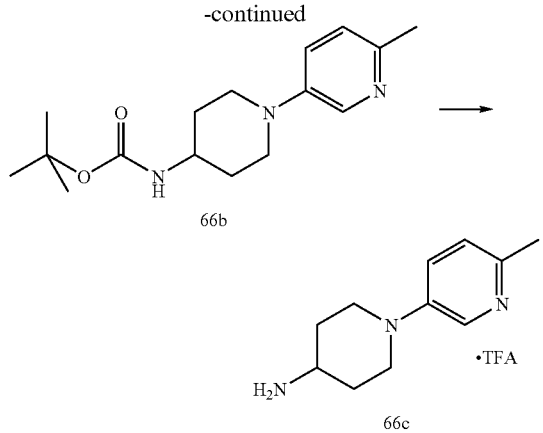

Step 1: Pd(dba)3 (18.3 mg, 0.02 mmol), Xantphos (35 mg, 0.06 mmol) and Cs₂CO₃ (456 g, 1.4 mmol) were added to 10 mL of 1,4-dioxane under the protection of N₂, compounds 6a (200 mg, 1 mmol) and 66a (224 mg, 1.3 mmol) were added to this mixture. The resulting mixture was heated to 100° C. for 24 h, cooled to room temperature which was taken up in EA (50 mL), washed with brine and water. The organic phase was dried with anhydrous MgSO₄ and concentrated under reduced pressure to give a residue which was purified by column chromatography (PE:EA=1:1) to provide compound 66b (159 mg, 55%).

Step 2: The following de-Boc and final coupling steps were similar to that of Example 48. The title compound (61 mg, 71%) was obtained as orange solid. ¹H NMR (300 MHz, DMSO-d6): δ=13.67 (s, 1H), 10.89 (s, 1H), 8.16-8.17 (d, 1H), 7.62-7.78 (m, 3H), 7.24-7.28 (dd, 1H), 7.05-7.07 (d, 1H), 6.81-6.95 (m, 2H), 3.88-3.93 (m, 1H), 3.65-3.69 (d, 2H), 3.17-3.26 (m, 2H), 2.79-2.88 (m, 2H), 2.40-2.42 (ds, 6H), 2.34 (s, 3H), 1.84-1.92 (m, 2H), 1.56-1.67 (m, 2H). LC/MS: 474.2 [M+H]+.

Example 68

Preparation of 5-[5-Fluoro-2-oxo-1,2-dihydro-indol-(3Z)-ylidenemethyl]-2,4-dimethyl-1H-pyrrole-3-carboxylic acid [(S)-1-(6-methyl-pyridin-3-yl)-pyrrolidin-3-yl]-amide

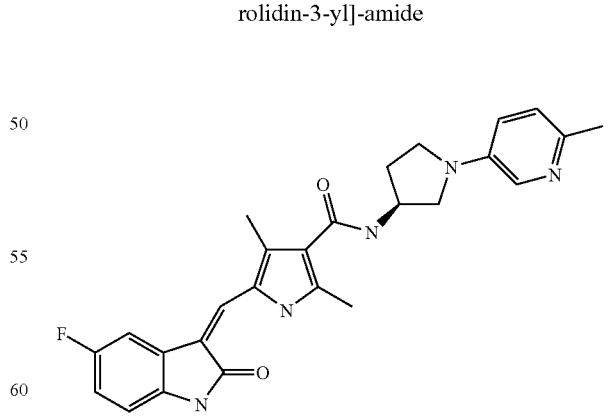

The title compound (64 mg, 65%) was synthesized as orange solid following the procedure of Example 67. ¹H NMR (300 MHz, DMSO-d6): δ=13.67 (s, 1H), 10.89 (s, 1H), 7.92-7.95 (d, 1H), 7.71-7.82 (m, 3H), 7.00-7.03 (d, 1H), 6.81-6.95 (m, 3H), 4.54-4.58 (m, 1H), 3.54-3.59 (m, 1H), 3.37-3.42 (m, 1H), 3.28-3.30 (m, 3H), 3.15-3.20 (q, 1H), 2.38-2.40 (ds, 6H), 2.29 (s, 3H), 2.22-2.27 (m, 1H), 1.99-2.05 (m, 1H). LC/MS: 460.2 [M+H]+.

Example 69

Preparation of 5-[5-Fluoro-2-oxo-1,2-dihydro-indol-(3Z)-ylidenemethyl]-2,4-dimethyl-1H-pyrrole-3-carboxylic acid [(S)-2-oxo-1-(tetrahydro-pyran-4-ylmethyl)-pyrrolidin-3-yl]-amide

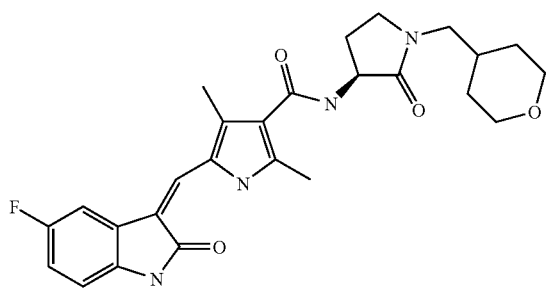

The title compound (30 mg, 50%) was synthesized as orange solid following the procedure of Example 60. $^1$H NMR (300 MHz, DMSO-d6): δ=13.67 (s, 1H), 10.91 (s, 1H), 7.71-7.88 (m, 3H), 6.82-6.96 (m, 2H), 4.60-4.62 (q, 1H), 3.82-3.85 (d, 2H), 2.29-3.31 (m, 6H), 2.42-2.44 (ds, 6H), 2.31-2.35 (m, 1H), 1.84-1.98 (m, 2H), 1.49-1.58 (m, 2H), 1.05-1.19 (m, 2H). LC/MS: 481.0 [M+H]+.

Example 70

Preparation of 5-[5-Fluoro-2-oxo-1,2-dihydro-indol-(3Z)-ylidenemethyl]-2,4-dimethyl-1H-pyrrole-3-carboxylic acid [1-(2-methanesulfonyl-ethyl)-piperidin-4-yl]-amide

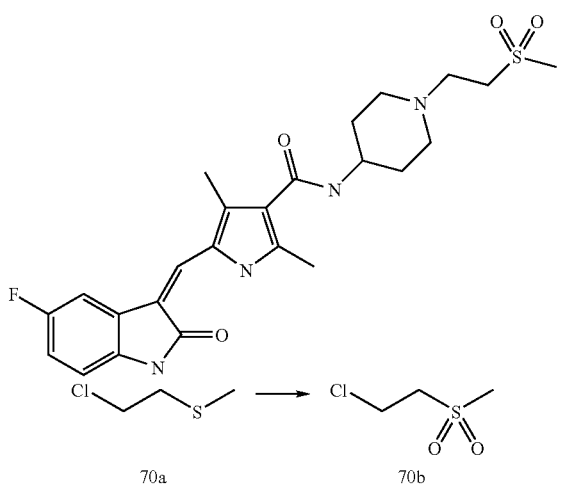

Step 1: 30% H2O2 aqueous solution (5 mL) was added to a solution of 70a (900 mg, 8.2 mmol) in acetic acid (5 mL) at room temperature. During the addition, heat was giving off. The resulting mixture was stirred overnight at room temperature and evaporated. The residue was purified by column chromatography (EA:PE=1:4) to provide 70b (538 mg, 46%) as colorless oil.

Subsequent steps are similar to that in Example 62. The title compound (97 mg, 84%) was obtained as orange solid. $^1$H NMR (300 MHz, DMSO-d6): δ=13.66 (s, 1H), 10.90 (s, 1H), 7.55-7.79 (m, 3H), 6.81-6.96 (m, 2H), 3.71-3.74 (m, 1H), 3.26-3.31 (m, 2H), 3.04 (s, 3H), 2.85-2.89 (m, 2H), 2.68-2.72 (t, 2H), 2.39-2.41 (ds, 6H), 2.04-2.12 (t, 2H), 1.76-1.82 (m, 2H), 1.49-1.56 (m, 2H). LC/MS: 487.2 [M−H]+.

Example 71

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-methanesulfonyl-ethyl)-pyrrolidin-3-yl]-amide

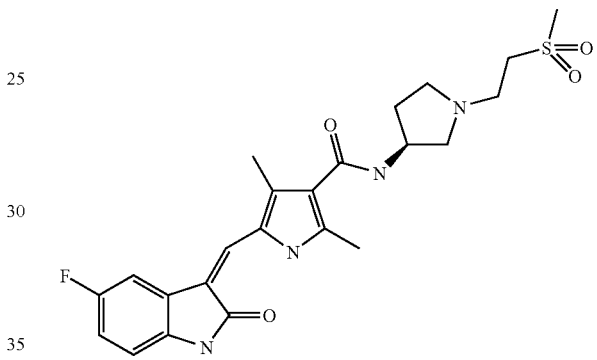

The title compound (96 mg, 84%) was synthesized as orange solid following the procedure of Example 70. $^1$H NMR (300 MHz, DMSO-d6): δ=13.67 (s, 1H), 10.90 (s, 1H), 7.71-7.80 (m, 3H), 6.81-6.96 (m, 2H), 4.35-4.37 (m, 1H), 3.27-3.34 (m, 4H), 3.04 (s, 3H), 2.68-2.81 (m, 4H), 2.39-2.41 (ds, 6H), 2.11-2.18 (m, 1H), 1.68-1.74 (m, 1H). LC/MS: 473.2 [M−H]+.

Example 72

Preparation of 5-[5-Fluoro-2-oxo-1,2-dihydro-indol-(3Z)-ylidenemethyl]-2,4-dimethyl-1H-pyrrole-3-carboxylic acid [(R)-2-(2-methanesulfonyl-ethyl)-3-oxo-isoxazolidin-4-yl]-amide

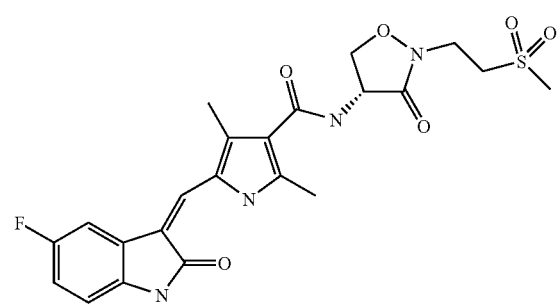

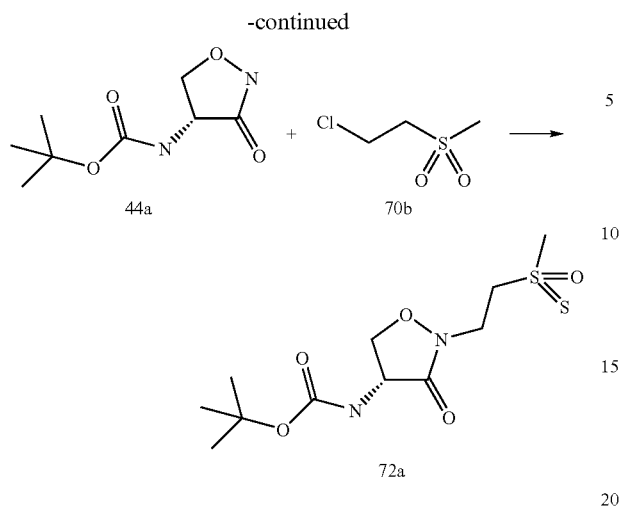

Step 1: Compound 44a (100 mg, 0.5 mmol), 70b (86 mg, 0.61 mmol), KI (86 mg, 0.52 mmol), K2CO3 (342 mg, 2.48 mmol) and acetonitrile (20 mL) were mixed in a microwave vial. The resulting mixture was reacted under microwave condition at 140° C. for 1 h. After being cooled, the mixture was filtered. The filtrate was evaporated and the residue was purified by column chromatography (EA) to provide 72a (82 mg, 49%).

Subsequent steps are similar to that of Example 48. The title compound (71 mg, 81%) was obtained as orange solid. $^1$H NMR (300 MHz, DMSO-d6): δ=13.73 (s, 1H), 10.93 (s, 1H), 8.13-8.16 (d, 1H), 7.73-7.80 (m, 2H), 6.82-6.97 (m, 2H), 4.96-5.05 (q, 1H), 4.59-4.64 (t, 1H), 4.08-4.14 (t, 1H), 3.91-3.96 (t, 2H), 3.44-3.49 (t, 2H), 3.06 (s, 3H), 2.43-2.45 (ds, 6H). LC/MS: 491.0 [M+H]$^+$.

Example 73

Preparation of 5-[5-Fluoro-2-oxo-1,2-dihydro-indol-(3Z)-ylidenemethyl]-2,4-dimethyl-1H-pyrrole-3-carboxylic acid [(S)-2-(2-methoxy-ethyl)-3-oxo-isoxazolidin-4-yl]-amide

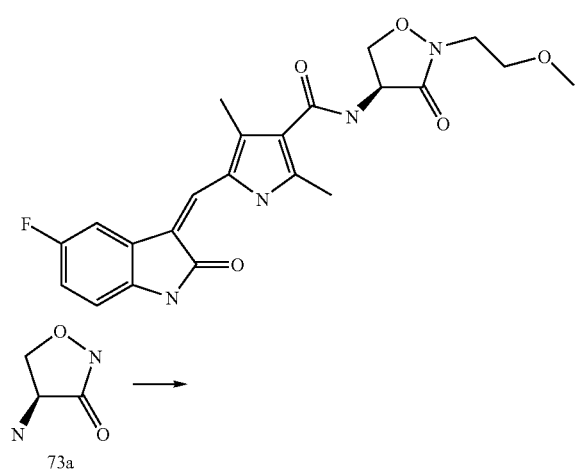

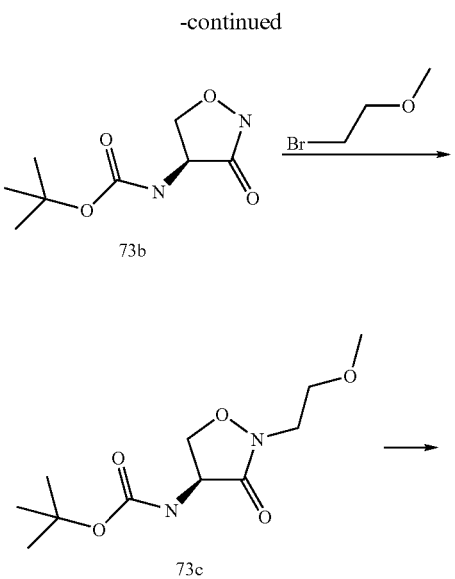

Step 1: Compound 73a (500 mg, 4.9 mmol) and TEA (990 mg, 9.8 mmol) were dissolved in a mixture of THF/water (75 mL, V/V 2:1). (Boc)2O (1.18 g, 5.4 mmol) was added dropwise under ice cooling. After the addition was complete, the mixture was warmed to room temperature and stirred overnight. The mixture was evaporated to dryness and the residue was purified by column chromatography (EA:PE=1:3) to provide compound 73b (406 mg, 41%) as white solid.

Step 2: Compound 73b (200 mg, 0.935 mmol), 1-bromo-2-methoxy-ethane (156 mg, 1.12 mmol), KI (163 mg, 0.98 mmol), K2CO3 (645 mg, 4.68 mmol) and acetonitrile (20 mL) were mixed in a microwave vial. The resulting mixture was reacted under microwave condition at 140° C. for 1 h. After being cooled, the mixture was filtered. The filtrate was evaporated and the residue was purified by column chromatography (EA::PE=1:3) to provide 73c (138 mg, 54%).

Step 3: The following de-Boc and final coupling steps were similar to that of Example 48. The title compound (83 mg, 83%) was obtained as orange solid. $^1$H NMR (300 MHz, DMSO-d6): δ=13.72 (s, 1H), 10.94 (s, 1H), 8.12-8.15 (d, 1H), 7.73-7.80 (m, 2H), 6.82-6.97 (m, 2H), 5.00-5.06 (q, 1H), 4.57-4.63 (t, 1H), 4.01-4.07 (m, 1H), 3.45-3.71 (m, 4H), 3.27 (s, 3H), 2.43-2.45 (ds, 6H). LC/MS: 442.9 [M+H]$^+$.

Example 74

Preparation of 5-[5-Fluoro-2-oxo-1,2-dihydro-indol-(3Z)-ylidenemethyl]-2,4-dimethyl-1H-pyrrole-3-carboxylic acid [(R)-2-(2-ethoxy-ethyl)-3-oxo-isoxazolidin-4-yl]-amide

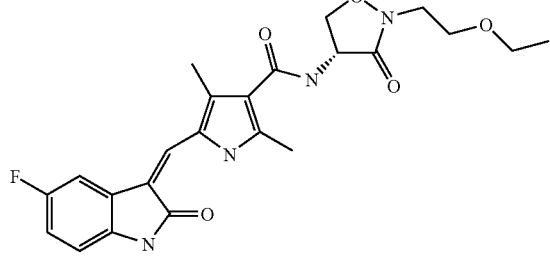

Following the procedure of Example 44, the title compound (42 mg, 91%) was obtained as orange solid. $^1$H NMR (300 MHz, DMSO-d6): δ=13.73 (s, 1H), 10.94 (s, 1H), 8.11-8.14 (d, 1H), 7.73-7.80 (m, 2H), 6.82-6.97 (m, 2H), 5.02-5.05 (q, 1H), 4.37-4.63 (t, 1H), 4.01-4.07 (m, 1H), 3.40-3.70 (m, 6H), 2.43-2.45 (ds, 6H), 1.03-1.17 (m, 3H). LC/MS: 457.2 [M+H]$^+$.

Example 75

Preparation of 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-2,5-dioxo-pyrrolidin-3-yl]-amide

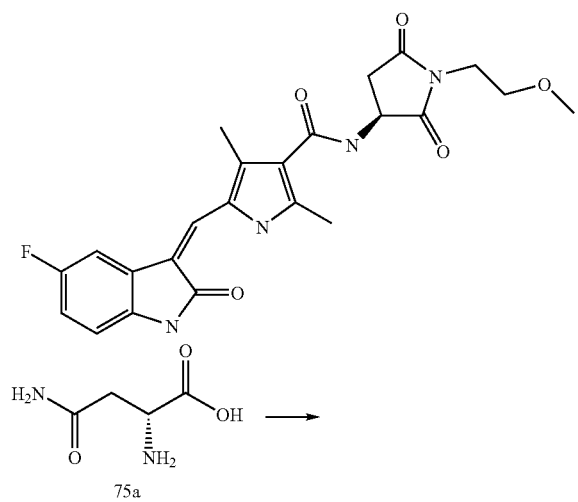

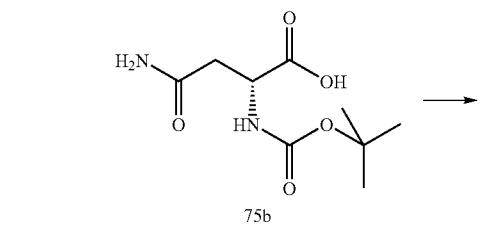

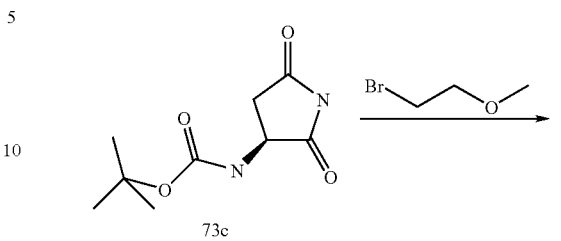

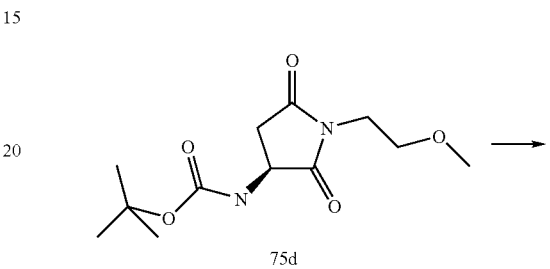

Step 1: To a solution of 75a (2.0 g 15 mmol), Na2CO3 (1.6 g, 15 mmol) in H2O/1,4-dioxane (30 mL/30 mL) was added (Boc)2O (3.96 g, 18.2 mmol) dropwise at room temperature. The mixture was stirred overnight and evaporated to remove 1,4-dioxane. The obtained aqueous solution was adjusted to pH=2 with 37% HCl. The formed precipitate was filtered, washed with water and dried to provide 75b (2.97 g, 84%) as white solid.

Step 2: To a stirred solution of 75b (2.0 g, 8.62 mmol) in DMF (15 mL) was added DCC (1.775 g, 8.62 mmol) and HOSu (0.99 g, 8.62 mmol). The mixture was heated to 80° C. with stirring for 6 h. DMF was evaporated and the residue was dissolved in EA (25 mL) and filtered. The filtrate was washed with water, brine and dried by Na2SO4. After evaporation, the residue was purified by column chromatography (EA:PE=1:1) to provide a pale yellow solid which was re-crystallized from EA to give 75c (0.83 g, 45%) as white solid.

Step 3: Subsequent steps are similar to that in Example 73 to obtain the title compound (83 mg, 90%) as orange solid. $^1$H NMR (300 MHz, DMSO-d6): δ=13.73 (s, 1H), 10.92 (s, 1H), 8.17-8.19 (d, 1H), 7.72-7.79 (m, 2H), 6.82-6.97 (m, 2H), 4.63-4.71 (m, 1H), 3.58-3.63 (q, 2H), 3.43-3.47 (t, 2H), 3.30 (s, 3H), 3.00-3.09 (q, 1H), 2.63-2.70 (dd, 1H), 2.43-2.44 (ds, 6H). LC/MS: 455.0 [M+H]$^+$.

Example 76

Preparation of 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-3-ylmethyl)-isoxazolidin-4-yl]-amide

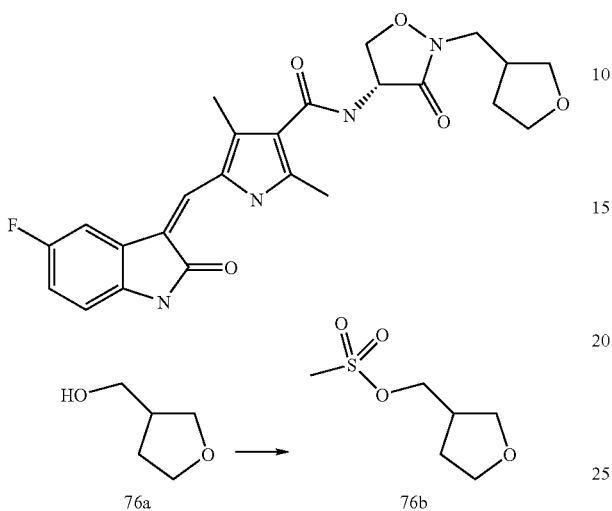

Step 1: To a solution of 76a (250 mg 2.45 mmol), TEA (273 mg, 2.7 mmol) in DCM (20 mL) was added methane sulfonyl chloride (298 mg, 2.6 mmol) drop-wise at 0° C. The mixture was stirred overnight at room temperature. After the reaction was complete, the mixture was washed with Na2CO3 solution. The organic phase was separated and the aqueous phase was extracted by DCM (20 mL*3). The organic phase was combined, dried over anhydrous Na2SO4 and evaporated to provide 76b (387 mg, 88%) as an oil.

Subsequent steps are similar to that in Example 72 to obtain the title compound (33 mg, 78%) obtained as orange solid. $^1$H NMR (300 MHz, DMSO-d6): δ=13.72 (s, 1H), 10.92 (s, 1H), 8.13-8.16 (d, 1H), 7.73-7.79 (m, 2H), 6.82-6.97 (m, 2H), 5.01-5.10 (q, 1H), 4.58-4.63 (t, 2H), 4.04-4.11 (m, 1H), 3.40-3.76 (m, 6H), 2.72-2.88 (m, 1H), 2.43-2.45 (ds, 6H), 1.95-2.01 (m, 1H), 1.59-1.63 (m, 1H). LC/MS: 469.2 [M+H]$^+$.

Example 77

Preparation of 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-2-ylmethyl)-isoxazolidin-4-yl]-amide

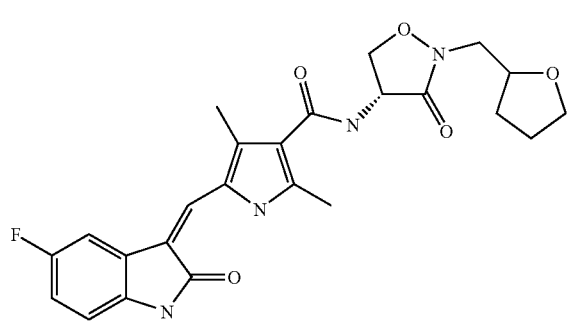

Following the procedure of Example 76, the title compound (20 mg, 72%) was obtained as orange solid. $^1$H NMR (300 MHz, DMSO-d6): δ=13.72 (s, 1H), 10.92 (s, 1H), 8.10-8.14 (m, 1H), 7.73-7.79 (m, 2H), 6.82-6.94 (m, 2H), 5.00-5.10 (m, 1H), 4.57-4.62 (t, 1H), 4.02-4.08 (m, 2H), 3.57-3.77 (m, 3H), 2.42-2.48 (m, 1H), 2.40-2.49 (ds, 6H), 1.60-1.93 (m, 4H). LC/MS: 468.9 [M+H]$^+$.

Example 78

Preparation of 5-[5-Fluoro-2-oxo-1,2-dihydro-indol-(3Z)-ylidenemethyl]-2,4-dimethyl-1H-pyrrole-3-carboxylic acid [(S)-2,5-dioxo-1-(tetrahydro-pyran-4-ylmethyl)-pyrrolidin-3-yl]-amide

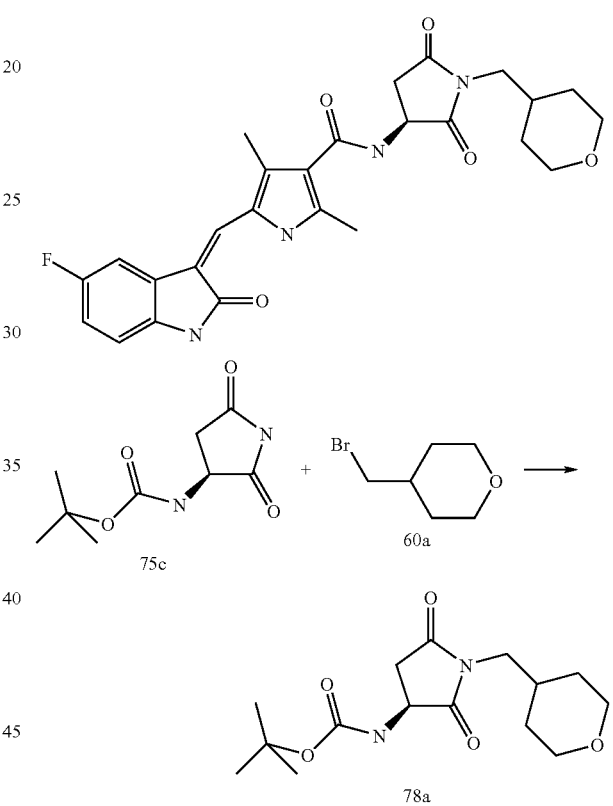

Step 1: Compound 75c (200 mg, 0.93 mmol), 60a (201 mg, 1.12 mmol), KI (163 mg, 0.98 mmol), K2CO3 (644 mg, 4.67 mmol) and acetonitrile (20 mL) were mixed in a microwave vial. The resulting mixture was reacted under microwave condition at 140° C. for 1 h. After being cooled, the mixture was filtered. The filtrate was evaporated and the residue was purified by column chromatography (EA::PE=1:3) to provide 78a (224 mg, 77%).

Subsequent steps are similar to that in Example 48 to obtain the title compound (60 mg, 72%) as orange solid. $^1$H NMR (300 MHz, DMSO-d6): δ=13.72 (s, 1H), 10.93 (s, 1H), 8.22-8.24 (d, 1H), 7.72-7.79 (m, 2H), 6.82-6.97 (m, 2H), 4.58-4.65 (m, 1H), 3.81-3.85 (m, 1H), 3.20-3.32 (m, 4H), 2.97-3.06 (q, 1H), 2.65-2.72 (dd, 1H), 2.42-2.43 (ds, 6H), 1.84-1.89 (m, 1H), 1.58-1.64 (m, 2H), 1.15-1.23 (m, 2H). LC/MS: 495.2 [M+H]$^+$.

Example 79

Preparation of 5-[5-Fluoro-2-oxo-1,2-dihydro-indol-(3Z)-ylidenemethyl]-2,4-dimethyl-1H-pyrrole-3-carboxylic acid [(S)-2,5-dioxo-1-(tetrahydro-pyran-4-yl)-pyrrolidin-3-yl]-amide

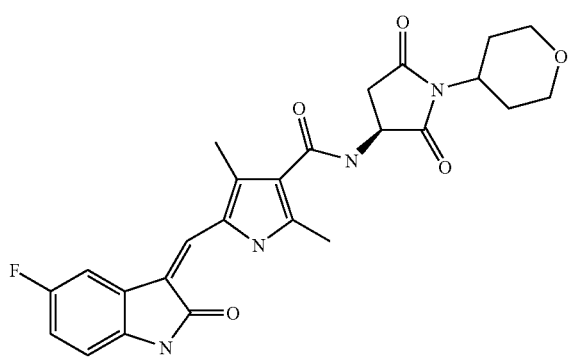

Following the procedure of Example 48, the title compound (71 mg, 62%) was obtained as orange solid. $^1$H NMR (300 MHz, DMSO-d6): δ=13.73 (s, 1H), 10.92 (s, 1H), 8.17-8.20 (d, 1H), 7.73-7.79 (m, 2H), 6.82-6.97 (m, 2H), 4.55-4.62 (m, 1H), 4.10-4.18 (m, 1H), 3.90-3.95 (dd, 2H), 3.32-3.39 (m, 2H), 2.93-3.02 (q, 1H), 2.59-2.67 (dd, 1H), 2.38-2.43 (ds, 6H), 2.26-2.37 (m, 2H), 1.48-1.51 (d, 2H). LC/MS: 481.2 [M+H]$^+$.

Example 80

Preparation of 5-[5-Fluoro-2-oxo-1,2-dihydro-indol-(3Z)-ylidenemethyl]-2,4-dimethyl-1H-pyrrole-3-carboxylic acid ((S)-1-dimethylcarbamoyl-2-oxo-pyrrolidin-3-yl)-amide

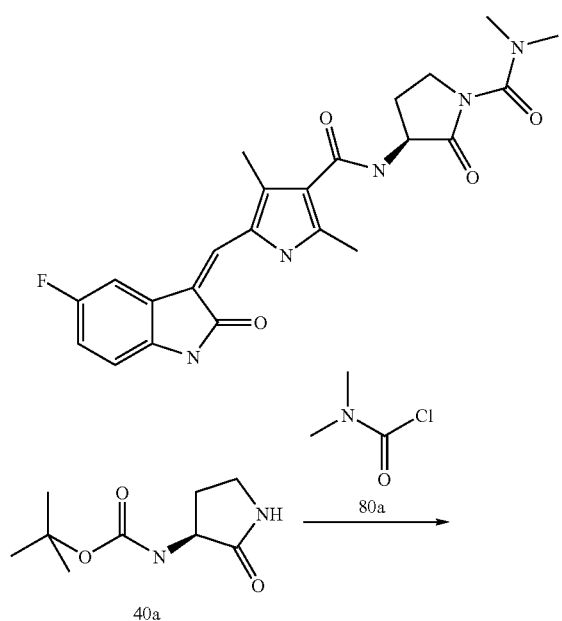

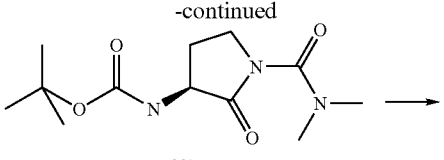

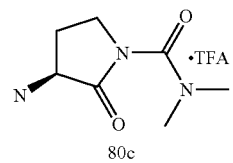

To a solution of 40a (200 mg, 1.0 mmol) in DMF (10 mL) was added 60% NaH (80 mg, 2.0 mmol) at 0° C. After stirring for another 1 h at room temperature, the mixture was added compound 80a (118 mg, 1.1 mmol). The resulted mixture was stirred at room temperature overnight and evaporated. The residue was purified by column chromatography (EA:PE=1:1) to provide 80b (98 mg, 36%).

Subsequent steps are similar to that in Example 48 to obtain the title compound (83 mg, 76%) as orange solid. $^1$H NMR (300 MHz, DMSO-d6): δ=13.70 (s, 1H), 10.90 (s, 1H), 8.04-8.07 (m, 1H), 7.72-7.78 (m, 2H), 6.82-6.96 (m, 2H), 4.36-4.53 (m, 1H), 3.57-3.62 (m, 2H), 2.92 (s, 6H), 2.42-2.45 (ds, 6H), 2.30-2.34 (m, 2H), 2.12-2.19 (m, 2H). LC/MS: 453.8 [M+H]$^+$.

Compounds in the tables herein are prepared in a manner similar as described above and in the general schemes.

Example 81

Biological Activity Assessment

VEGFR$_2$ (KDR) Biochemical Assay

The compounds are assayed for biochemical activity essentially according to the following procedure. In a final reaction volume of 25 μl, KDR (h) (5-10 mU) is incubated with 8 mM MOPS pH 7.0, 0.2 mM EDTA, 0.33 mg/ml myelin basic protein, 10 mM MgAcetate and [(γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filter mat and washed three times for 5 minutes in 75 mM phosphoric acid and once in methanol prior to drying and scintillation counting.

PDGFRβ Biochemical Assay

The compounds are assayed for biochemical activity essentially according to the following procedure. In a final reaction volume of 25 μl, PDGFRβ (h) (5-10 mU) is incubated with 8 mM MOPS pH 7.0, 0.2 mM EDTA, 0.1 mg/ml poly(Glu, Tyr) 4:1, 10 mM MgCl2, 10 mM MgAcetate and [(γ-33P-ATP) (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a filtermat A and washed three times for 5 minutes in 75 mM phosphoric acid and once in methanol prior to drying and scintillation counting.

AMPK Biochemical Assay

The compounds are assayed for biochemical activity essentially according to the following procedure. In a final reaction volume of 25 µl, AMPK (r) (5-10 mU) is incubated with 32 mM HEPES pH7.4, 0.65 mM DTT, 0.012% Brij-35, 200 µM AMP, 200 µM AMARAASAAALARRR, 10 mM MgAcetate and [(γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Some compounds exhibited significantly less AMPK inhibitory activities than sunitinib. They include, but are not limited to Examples 17, 22, 25, 29, 30, 31, 36, and 48.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A compound of formula (I) or pharmaceutical salt thereof:

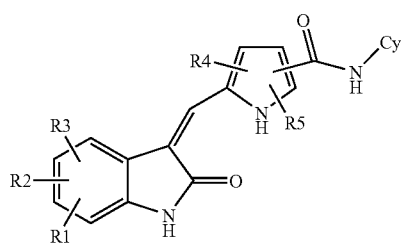

I wherein Cy is a cyclic structure that can be cycloalkyl or heterocyclic, each optionally substituted with $Z_1$, $Z_2$ and $Z_3$;

$R_1$, $R_2$, $R_3$, $R_4$, and $R_5$ are each independently:
(1) hydrogen or $R_6$, where $R_6$, is alkyl, alkenyl, alkynyl, cycloalkyl, cycloalkylalkyl, cycloalkenyl, cycloalkenylalkyl, heteroaryl, aralkyl, heteroarylalkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_6$;
(4) —$C(O)_2H$, —$C(O)_qR_6$, —$C(O)NR_7R_8$, —$C(O)C(O)NR_7R_8$, or —O—$C(O)_qR_6$, where q is 1 or 2;
(5) —$SO_3H$, or —$S(O)_qNR_7R_8$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$P(O)(OR_6)_2$;

$R_7$, $R_8$, $R_9$, $R_{10}$, $R_{11}$ and $R_{12}$ are each independently:

(1) hydrogen or $R_6$;
(2) $R_7$ and $R_8$ together with the nitrogen atom to which they are attached may be a heterocycle which is unsubstituted or substituted with $Z_1$, $Z_2$ and $Z_3$; or
(3) any two of $R_9$, $R_{10}$ and $R_{11}$ together with the nitrogen atoms to which they are attached may be a 3- to 12-membered saturated or unsaturated mono-, bi-, or tri-heterocyclic ring which is unsubstituted or substituted with $Z_1$, $Z_2$ and $Z_3$;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (13);
(2) —OH or —$OZ_{16}$;
(3) —SH or —$SZ_{16}$;
(4) —$C(O)_2H$, $C(O)_qZ_{16}$, —$C(O)NZ_{17}Z_{18}$, —$C(O)C(O)NZ_{17}Z_{18}$, or —O—$C(O)_qZ_{16}$, where q is 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—$C(O)$—$Z_{16}$;
(13) any two of $Z_1$, $Z_2$, and $Z_3$ may together be alkylene, alkenylene, aryl, heteroacyl, or heterocyclo completing a 3- to 8-membered saturated or unsaturated ring together with the atoms to which they are attached;

$Z_4$ and $Z_5$ are each independently
(1) a single bond;
(2) —$Z_{11}$—$S(O)_q$—$Z_{12}$—;
(3) —$Z_{11}$—$C(O)$—$Z_{12}$—;
(4) —$Z_{11}$—O—$Z_{12}$—;
(5) —$Z_{11}$—S—$Z_{12}$—;
(6) —$Z_{11}$—O—$C(O)$—$Z_{12}$—; or
(7) —$Z_1$—$C(O)$—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —$C(O)C(O)NZ_{17}Z_{18}$, or —O—$C(O)_qZ_{21}$, where q is 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—$C(O)$—$Z_{21}$;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl alkylaryl, cycloalkylaryl, heterocyclo, a heterocycloalkyl;

each $Z_{22}$ is independently is, (2) —OH or —$OZ_{21}$;

(3) —SH or —$SZ_{21}$;

(4) —$C(O)_2H$, $C(O)_qZ_{21}$, —$C(O)NZ_{21}Z_{21}$, —$C(O)C(O)NZ_{21}Z_{21}$, or —O—$C(O)_qZ_{21}$, where q is 1 or 2;

(5) —$SO_3H$, —$S(O)_qZ_{21}$, or —$S(O)_qNZ_{21}Z_{21}$;

(6) halo;

(7) cyano;

(8) nitro;

(9) —$Z_4$—$NZ_{21}Z_{21}$;

(10) —$Z_4$—$N(Z_{21})$—$Z_5$—$NZ_{21}Z_{21}$;

(11) oxo;

(12) —O—C(O)—$Z_{21}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$;

provided said compound is other than a compound of formula IIa or IIb;

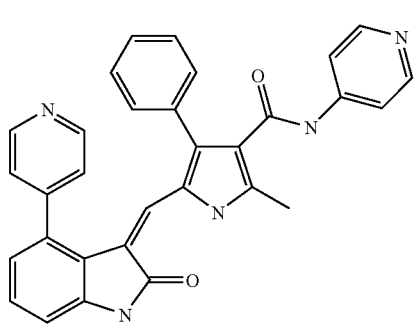

IIa

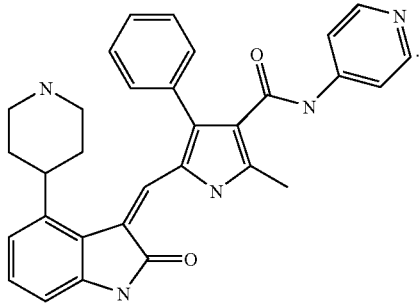

IIb

2. The compound of claim 1 wherein Cy is a non-aromatic cycloalkyl or heterocyclic structure that is optionally substituted with $Z_1$, $Z_2$ and $Z_3$.

3. The compound of claim 1 wherein Cy is a heterocyclic structure that is optionally substituted with $Z_1$, $Z_2$ and $Z_3$.

4. A compound of claim 1 wherein any $R_1$, $R_2$ or $R_3$ in the 4-indolinone position is not a heterocycle or heteroaryl group.

5. The compound of claim 1 that is selected from:

5-[5-fluoro-2-oxo-1,2-dihydro-indol-(3Z)-ylidenemethyl]-2,4-dimethyl-1H-pyrrole-3-carboxylic acid (1-acetyl-piperidin-4-yl)-amide, 5-[5-fluoro-2-oxo-1,2-dihydro-indol-(3Z)-ylidenemethyl]-2,4-dimethyl-1H-pyrrole-3-carboxylic acid (1-methanesulfonyl-piperidin-4-yl)-amide, N-(2H-3,4,5,6-tetrahydropyran-4-yl){5-[(5-fluoro-2-oxo (1H-benzo[d]azolin-3-ylidene))methyl]-2,4-dimethylpyrrol-3-yl}carboxamide, 5-[5-Fluoro-2-oxo-1,2-dihydro-indol-(3Z)-ylidenemethyl]-2,4-dimethyl-1H-pyrrole-3-carboxylic acid piperidin-4-ylamide, 5-[5-Fluoro-2-oxo-1,2-dihydro-indol-(3Z)-ylidenemethyl]-2,4-dimethyl-1H-pyrrole-3-carboxylic acid ((S)-1-acetyl-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid ((S)-1-methanesulfonyl-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid (1,1-dioxo-tetrahydro-thiophen-3-yl)-amide, 5-[5-Fluoro-2-oxo-1,2-dihydro-indol-(3Z)-ylidenemethyl]-2,4-dimethyl-1H-pyrrole-3-carboxylic acid (1-pyrimidin-2-yl-piperidin-4-yl)-amide, 5-[5-Fluoro-2-oxo-1,2-dihydro-indol-(3Z)-ylidenemethyl]-2,4-dimethyl-1H-pyrrole-3-carboxylic acid (3,4,5,6-tetrahydro-2H-[1,3']bipyridinyl-4-yl)-amide, 5-[5-Fluoro-2-oxo-1,2-dihydro-indol-(3Z)-ylidenemethyl]-2,4-dimethyl-1H-pyrrole-3-carboxylic acid (4-hydroxy-1,1-dioxo-tetrahydro-thiophen-3-yl)-amide, 5-[5-Fluoro-2-oxo-1,2-dihydro-indol-(3Z)-ylidenemethyl]-2,4-dimethyl-1H-pyrrole-3-carboxylic acid (1,1-dioxo-hexahydro-thiopyran-4-yl)-amide, 5-[5-fluoro-2-oxo-1,2-dihydro-indol-(3Z)-ylidenemethyl]-2,4-dimethyl-1H-pyrrole-3-carboxylic acid ((S)-6-oxo-piperidin-3-yl)-amide, 5-[5-Fluoro-2-oxo-1,2-dihydro-indol-(3Z)-ylidenemethyl]-2,4-dimethyl-1H-pyrrole-3-carboxylic acid ((2S, 3S,4R,5S,6S)-3,4,5-trihydroxy-6-hydroxymethyl-tetrahydro-pyran-2-yl)-amide, 5-[5-Fluoro-2-oxo-1,2-dihydro-indol-(3Z)-ylidenemethyl]-2,4-dimethyl-1H-pyrrole-3-carboxylic acid [1-(2-hydroxy-acetyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-acetyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid (4-hydroxy-tetrahydro-furan-3-yl)-amide, 5-[5-Fluoro-2-oxo-1,2-dihydro-indol-(37)-ylidenemethyl]-2,4-dimethyl-1H-pyrrolo-3-carboxylic acid ((S)-2-oxo-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid (1-benzyl-4-hydroxy-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid (1-acetyl-4-hydroxy-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid (1-dimethylaminooxalyl-piperidin-4-yl)-amide, 5-[5-Fluoro-2-oxo-1,2-dihydro-indol-(3Z)-ylidenemethyl]-2,4-dimethyl-1H-pyrrole-3-carboxylic acid ((S)-1-dimethylaminooxalyl-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid ((2S,3S,4R,5S)-3,4-dihydroxy-5-hydroxymethyl-tetrahydro-furan-2-yl)-amide, 5-[5-Fluoro-2-oxo-1,2-dihydro-indol-(3Z)-ylidenemethyl]-2,4-dimethyl-1H-pyrrole-3-carboxylic acid ((S)-1-carbamoylmethyl-2-oxo-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid [(S)-1-(2-hydroxy-ethyl)-2-oxo-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(R)-2-(2-hydroxy-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid ((R)-2-dimethylcarbamoylmethyl-3-oxo-isoxazolidin-4-yl)-amide, 5-[5-Fluoro-2-oxo-1,2-dihydro-indol-(3Z)-ylidenemethyl]-2,4-dimethyl-1H-pyrrole-3-carboxylic acid ((R)-2-ethyl-3-oxo-isoxazolidin-4-yl)-amide, 5-[5-Fluoro-2-oxo-1,2-dihydro-indol-(3Z)-ylidenemethyl]-2,4-dimethyl-1H-pyrrole-3-carboxylic acid ((R)-2-carbamoylmethyl-3-oxo-isoxazolidin-4-yl)-amide, 5-[5-Fluoro-2-oxo-1,2-dihydro-indol-(3Z)-ylidenemethyl]-2,4-dimethyl-1H-pyrrole-3-carboxylic acid [(R)-2-(2-methoxy-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid ((R)-3-oxo-2-pyridin-3-ylmethyl-isoxazolidin-4-yl)-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-yl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-furan-3-yl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [1-(morpholine-4-carbonyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(morpholine-4-carbonyl)-pyrrolidin-3-yl]-amide, 4-({5-[5-Fluoro-2-oxo-1,2-dihydro-indol-(3Z)-ylidenemethyl]-2,4-dimethyl-1H-pyrrole-3-carbonyl}-amino)-piperidine-1-carboxylic acid dimethylamide, 5-[5-Fluoro-2-oxo-1,2-dihydro-indol-(3Z)-ylidenemethyl]-2,4-dimethyl-1H-pyrrole-3-carboxylic acid ((S)-1-dimethylcarbamoyl-pyrrolidin-3-yl)-amide, 5-[5-fluoro-2-oxo-1,2-dihydro-indol-(3Z)-ylidenemethyl]-2,4-dimethyl-1H-pyrrole-3-carboxylic acid [1-(2-methoxy-acetyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-acetyl)-pyrrolidin-3-yl]-amide, N-((3R)oxolan-3-yl){5-[(5-fluoro-2-oxo(1H-benzo[d]azolin-3-ylidene))methyl]-2,4-dimethylpyrrol-3-yl}carboxamide, 5-[5-Fluoro-2-oxo-1,2-dihydro-indol-(3Z)-ylidenemethyl]-2,4-dimethyl-1H-pyrrole-3-carboxylic acid [(R)-2-(2-morpholin-4-yl-ethyl)-3-oxo-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methoxy-ethyl)-2-oxo-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid ((S)-2-oxo-1-pyridin-4-ylmethyl-pyrrolidin-3-yl)-amide, 5-[5-Fluoro-2-oxo-1,2-dihydro-indol-(3Z)-ylidenemethyl]-2,4-dimethyl-1H-pyrrole-3-carboxylic acid [(R)-3-oxo-2-(tetrahydro-pyran-4-ylmethyl)-isoxazolidin-4-yl]-amide, 5-[5-Fluoro-2-oxo-1,2-dihydro-indol-(3Z)-ylidenemethyl]-2,4-dimethyl-1H-pyrrole-3-carboxylic acid [(5)-1-(2-methoxy-ethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-methoxy-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [1-(2-dimethylamino-acetyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-dimethylamino-acetyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-hydroxy-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(5)-1-(2-hydroxy-ethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid (6'-methyl-3,4,5,6-tetrahydro-2H-[1,3']pyridinyl-4-yl)-amide, 5-[5-Fluoro-2-oxo-1,2-dihydro-indol-(3Z)-ylidenemethyl]-2,4-dimethyl-1H-pyrrole-3-carboxylic acid [(S)-1-(6-methyl-pyridin-3-yl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [(S)-2-oxo-1-(tetrahydro-pyran-4-ylmethyl)-pyrrolidin-3-yl]-amide, 5-[5-Fluoro-2-oxo-1,2-dihydro-indol-(3Z)-ylidenemethyl]-2,4-dimethyl-1H-pyrrole-3-carboxylic acid [1-(2-methanesulfonyl-ethyl)-piperidin-4-yl]-amide, 5-[5-Fluoro-2-oxo-1,2-dihydro-indol-(3Z)-ylidenemethyl]-2,4-dimethyl-1H-pyrrole-3-carboxylic acid [(S)-1-(2-methanesulfonyl-ethyl)-pyrrolidin-3-yl]-amide, 5-[5-Fluoro-2-oxo-1,2-dihydro-indol-(3Z)-ylidenem-ethyl]-2,4-dimethyl-1H-pyrrole-3-carboxylic acid [(R)-2-(2-methanesulfonyl-ethyl)-3-oxo-isoxazolidin-4-yl]-amide, 5-[5-Fluoro-2-oxo-1,2-dihydro-indol-(3Z)-ylidenem-ethyl]-2,4-dimethyl-1H-pyrrole-3-carboxylic acid [(S)-2-(2-methoxy-ethyl)-3-oxo-isoxazolidin-4-yl]-amide, 5-[5-Fluoro-2-oxo-1,2-dihydro-indol-(3Z)-ylidenem-ethyl]-2,4-dimethyl-1H-pyrrole-3-carboxylic acid [(R)-2-(2-ethoxy-ethyl)-3-oxo-isoxazolidin-4-yl]-amide, 5-[5-Fluoro-2-oxo-1,2-dihydro-indol-(3Z)-ylidenem-ethyl]-2,4-dimethyl-1H-pyrrole-3-carboxylic acid [(S)-1-(2-methoxy-ethyl)-2,5-dioxo-pyrrolidin-3-yl]-amide, 5-[5-Fluoro-2-oxo-1,2-dihydro-indol-(3Z)-ylidenem-ethyl]-2,4-dimethyl-1H-pyrrole-3-carboxylic acid [(R)-3-oxo-2-(tetrahydro-furan-3-ylmethyl)-isoxazolidin-4-yl]-amide, 5-[5-Fluoro-2-oxo-1,2-dihydro-indol-(3Z)-ylidenem-ethyl]-2,4-dimethyl-1H-pyrrole-3-carboxylic acid [(R)-3-oxo-2-(tetrahydro-furan-2-ylmethyl)-isoxazolidin-4-yl]-amide, 5-[5-Fluoro-2-oxo-1,2-dihydro-indol-(3Z)-ylidenem-ethyl]-2,4-dimethyl-1H-pyrrole-3-carboxylic acid [(S)-2,5-dioxo-1-(tetrahydro-pyran-4-ylmethyl)-pyrrolidin-3-yl]-amide, 5-[5-Fluoro-2-oxo-1,2-dihydro-indol-(3Z)-ylidenem-ethyl]-2,4-dimethyl-1H-pyrrole-3-carboxylic acid [(S)-2,5-dioxo-1-(tetrahydro-pyran-4-yl)-pyrrolidin-3-yl]-amide, and 5-[5-Fluoro-2-oxo-1,2-dihydro-indol-(3Z)-ylidenem-ethyl]-2,4-dimethyl-1H-pyrrole-3-carboxylic acid ((S)-1-dimethylcarbamoyl-2-oxo-pyrrolidin-3-yl)-amide.

6. The compound of claim 1 that is selected from:

5-[5-fluoro-2-oxo-1,2-dihydro-indol-(3Z)-ylidenem-ethyl]-2,4-dimethyl-1H-pyrrole-3-carboxylic acid (4-hydroxy-cyclohexyl)-amide, 5-[5-Fluoro-2-oxo-1,2-dihydro-indol-(3Z)-ylidenem-ethyl]-2,4-dimethyl-1H-pyrrole-3-carboxylic acid (4-amino-cyclohexyl)-amide, 5-[5-Fluoro-2-oxo-1,2-dihydro-indol-(3Z)-ylidenem-ethyl]-2,4-dimethyl-1H-pyrrole-3-carboxylic acid (4-oxo-cyclohexyl)-amide, 5-[5-Fluoro-2-oxo-1,2-dihydro-indol-(3Z)-ylidenem-ethyl]-2,4-dimethyl-1H-pyrrole-3-carboxylic acid ((1S,2S)-2-hydroxy-cyclopentyl)-amide, 5-[5-Fluoro-2-oxo-1,2-dihydro-indol-(3Z)-ylidenem-ethyl]-2,4-dimethyl-1H-pyrrole-3-carboxylic acid ((1S,2R)-2-hydroxy-cyclopentyl)-amide, 5-[5-Fluoro-2-oxo-1,2-dihydro-indol-(3Z)-ylidenem-ethyl]-2,4-dimethyl-1H-pyrrole-3-carboxylic acid (4-acetylamino-cyclohexyl)-amide, 5-[5-Fluoro-2-oxo-1,2-dihydro-indol-(3Z)-ylidenem-ethyl]-2,4-dimethyl-1H-pyrrole-3-carboxylic acid (4-methanesulfonylamino-cyclohexyl)-amide, 5-[5-Fluoro-2-oxo-1,2-dihydro-indol-(3Z)-ylidenem-ethyl]-2,4-dimethyl-1H-pyrrole-3-carboxylic acid ((1S,2S)-2-hydroxy-cyclohexyl)-amide, 5-[5-Fluoro-2-oxo-1,2-dihydro-indol-(3Z)-ylidenem-ethyl]-2,4-dimethyl-1H-pyrrole-3-carboxylic acid [4-(morpholine-4-carbonyl)-cyclohexyl]-amide, 5-[5-Fluoro-2-oxo-1,2-dihydro-indol-(3Z)-ylidenem-ethyl]-2,4-dimethyl-1H-pyrrole-3-carboxylic acid [4-(pyrrolidine-1-carbonyl)-cyclohexyl]-amide, 5-[5-Fluoro-2-oxo-1,2-dihydro-indol-(3Z)-ylidenem-ethyl]-2,4-dimethyl-1H-pyrrole-3-carboxylic acid [4-(aziridine-1-carbonyl)-cyclohexyl]-amide, 5-[5-Fluoro-2-oxo-1,2-dihydro-indol-(3Z)-ylidenem-ethyl]-2,4-dimethyl-1H-pyrrole-3-carboxylic acid [(1R,3S)-3-pyrrolidine-1-carbonyl)-cyclopentyl]-amide, 5-[5-Fluoro-2-oxo-1,2-dihydro-indol-(3Z)-ylidenem-ethyl]-2,4-dimethyl-1H-pyrrole-3-carboxylic acid [(1R,3S)-3-(morpholine-4-carbonyl)-cyclopentyl]-amide, 5-[5-Fluoro-2-oxo-1,2-dihydro-indol-(3Z)-ylidenem-ethyl]-2,4-dimethyl-1H-pyrrole-3-carboxylic acid [(1R,3S)-3-(aziridine-1-carbonyl)-cyclopentyl]-amide, 5-[5-Fluoro-2-oxo-1,2-dihydro-indol-(3Z)-ylidenem-ethyl]-2,4-dimethyl-1H-pyrrole-3-carboxylic acid [(1R,2S)-2-(pyrrolidine-1-carbonyl)-cyclopentyl]-amide, 5-[5-Fluoro-2-oxo-1,2-dihydro-indol-(3Z)-ylidenem-ethyl]-2,4-dimethyl-1H-pyrrole-3-carboxylic acid [(1R,2S)-2-(morpholine-4-carbonyl)-cyclopentyl]-amide, and 5-[5-Fluoro-2-oxo-1,2-dihydro-indol-(3Z)-ylidenem-ethyl]-2,4-dimethyl-1H-pyrrole-3-carboxylic acid [(1R,2S)-2-(aziridine-1-carbonyl)-cyclopentyl]-amide.

7. The compound of claim 1, wherein the Cy is optionally substituted cycloalkyl.

8. The compound of claim 1, wherein the compound of formula I is selected from the following,

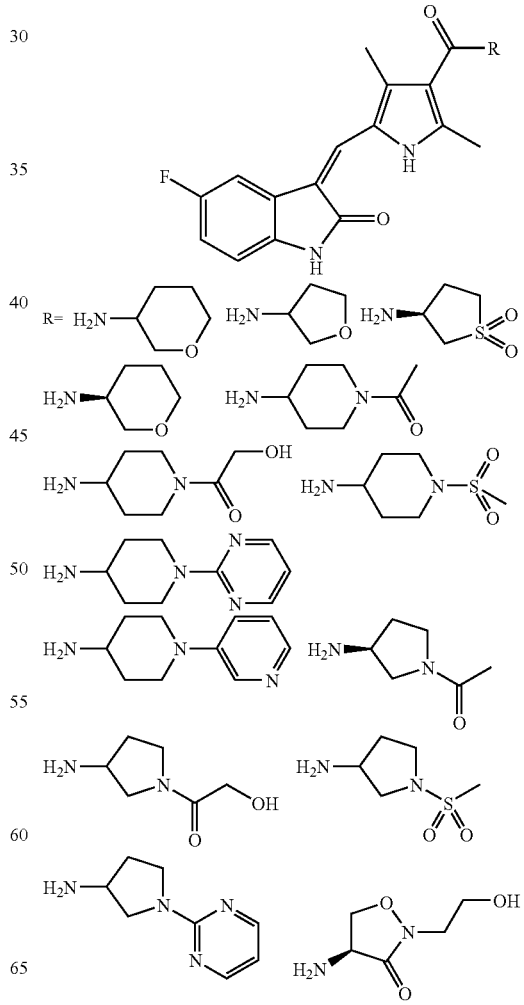

-continued

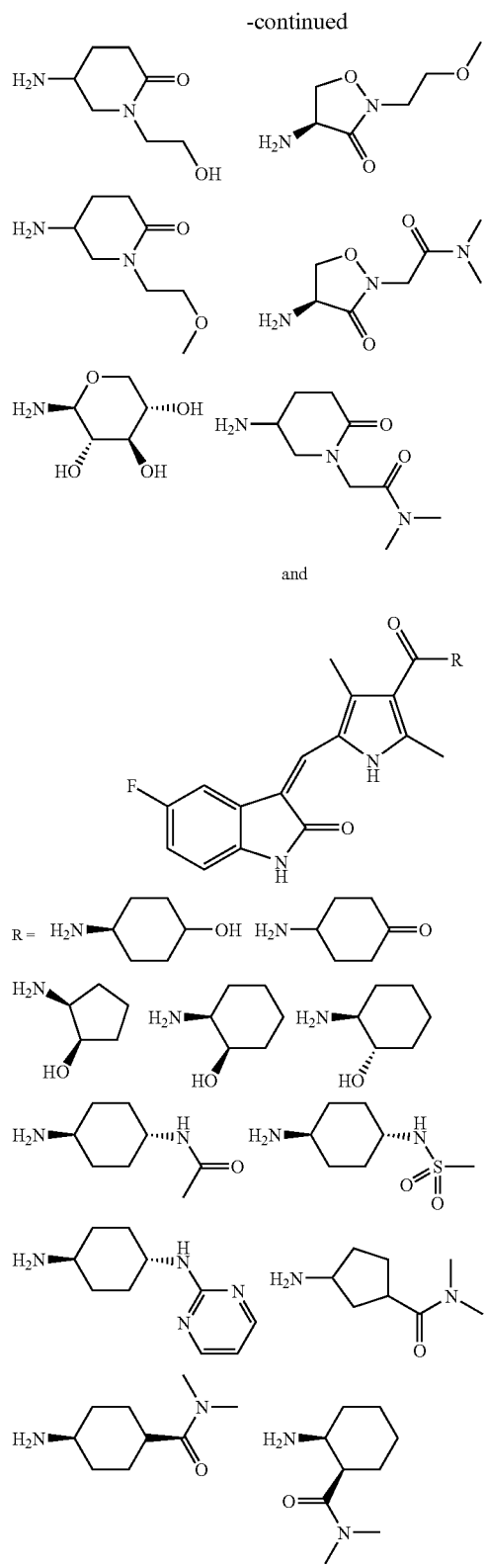

and or pharmaceutical salt thereof.

9. A method of modulating the activity of a kinase enzyme comprising contacting a kinase enzyme with a compound of formula I in claim 1.

10. A composition comprising a compound of formula I, or pharmaceutically acceptable salt thereof, according to any of claims 1-8 and a pharmaceutically acceptable carrier.

11. The composition of claim 10, further comprising an additional therapeutic agent.

12. The composition of claim 11, wherein the additional therapeutic agent is an anticancer agent.

13. A method of modulating kinase activity in a subject in need thereof comprising administering to the subject an effective amount of a compound of formula (I) in claim 1, or pharmaceutical salt thereof.

14. The method of claim 13, wherein the compound selectively inhibits a kinase target preferentially over inhibition of AMPK.

15. The method of claim 14, wherein the compound selectively inhibits a kinase target preferentially over inhibition of AMPK with greater selectivity than 5-[5-Fluoro-2-oxo-1,2-dihydro-indol-(3Z)-ylidenemethyl]-2,4-dimethyl-1H-pyrrole-3-carboxylic acid (2-diethylaminoethyl)-amide.

16. The method of claim 13, wherein the subject experiences little or no fatigue side effect.

17. The compound of claim 1, wherein the Cy is optionally substituted 5-membered ring heterocyclic.

18. The compound of claim 1, wherein the Cy is optionally substituted 6-membered ring heterocyclic.

19. The compound of claim 1, having the structure of formula III:

(III)

20. The compound of claim 19, wherein $R_3$ is halo.
21. The compound of claim 20, wherein $R_3$ is fluoro.
22. The compound of claim 19, wherein $R_1$ and $R_2$ are H, and $R_3$ is fluoro.

* * * * *

UNITED STATES PATENT AND TRADEMARK OFFICE
CERTIFICATE OF CORRECTION

PATENT NO. : 7,683,057 B2  Page 1 of 1
APPLICATION NO. : 12/005872
DATED : March 23, 2010
INVENTOR(S) : C. Liang et al.

It is certified that error appears in the above-identified patent and that said Letters Patent is hereby corrected as shown below:

On the Title Pg, after Item (65) Prior Publication Data, and before Item (51), please insert the following Item (60):

--Related U.S. Application Data

(60) Provisional application No. 60/844,902, filed September 15, 2006.--

Signed and Sealed this

Thirteenth Day of July, 2010

David J. Kappos
*Director of the United States Patent and Trademark Office*